(12) United States Patent
Uneme et al.

(10) Patent No.: US 9,730,449 B2
(45) Date of Patent: Aug. 15, 2017

(54) THIAZOLE COMPOUND AND ITS USE IN PEST CONTROL

(71) Applicant: Sumitomo Chemical Company, Limited, Tokyo (JP)

(72) Inventors: Hideki Uneme, Hyogo (JP); Yasser Samir Abdelhalek Sokeirik, Runcorn (AU)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/108,657

(22) PCT Filed: Dec. 25, 2014

(86) PCT No.: PCT/JP2014/084754
§ 371 (c)(1),
(2) Date: Jun. 28, 2016

(87) PCT Pub. No.: WO2015/102104
PCT Pub. Date: Jul. 9, 2015

(65) Prior Publication Data
US 2016/0324155 A1 Nov. 10, 2016

(30) Foreign Application Priority Data
Jan. 6, 2014 (JP) .................. 2014-000111

(51) Int. Cl.
| | |
|---|---|
| *A01N 43/78* | (2006.01) |
| *C07D 277/34* | (2006.01) |
| *C07D 277/36* | (2006.01) |
| *C07D 401/12* | (2006.01) |
| *C07D 417/12* | (2006.01) |
| *C07D 277/20* | (2006.01) |

(52) U.S. Cl.
CPC ............ *A01N 43/78* (2013.01); *C07D 277/20* (2013.01); *C07D 277/36* (2013.01); *C07D 417/12* (2013.01)

(58) Field of Classification Search
CPC .... A01N 43/78; C07D 277/34; C07D 277/36; C07D 401/12

USPC ............ 514/314, 342, 369; 546/176, 269.7; 548/183
See application file for complete search history.

(56) References Cited

U.S. PATENT DOCUMENTS

2005/0215578 A1   9/2005   Ihara et al.

FOREIGN PATENT DOCUMENTS

| | | |
|---|---|---|
| CN | 1617863 A | 5/2005 |
| DE | 102007012168 A1 | 9/2008 |
| JP | H09176141 A | 7/1997 |
| JP | 2000239264 A | 9/2000 |
| WO | 9928305 A1 | 6/1999 |
| WO | 9940076 A1 | 8/1999 |
| WO | 0003974 A1 | 1/2000 |
| WO | 03059897 A1 | 7/2003 |

OTHER PUBLICATIONS

Int'l Search Report issued Mar. 24, 2015 in Int'l Application No. PCT/JP2014/084754.
Int'l Preliminary Report on Patentabitlity issued Jul. 12, 2016 in Int'l Application No. PCT/JP2014/084754.
Office Action issued Mar. 13, 2017 in CN Application No. 2014800719342.

*Primary Examiner* — Brenda Coleman
(74) *Attorney, Agent, or Firm* — Panitch Schwarze Belisario & Nadel LLP

(57) ABSTRACT

A thiazole compound represented by Formula (1):

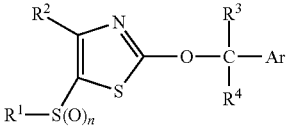

(1)

wherein $R^1$ represents a C1-C4 alkyl group optionally having one or more fluorine atoms, $R^2$ represents a hydrogen atom etc., $R^3$ and $R^4$ are the same or different and each represents a hydrogen atom etc., Ar represents a phenyl group optionally having one or more atoms or groups selected from the group A etc., and n represents 1 or 2 has excellent control activity against pests.

9 Claims, No Drawings

THIAZOLE COMPOUND AND ITS USE IN PEST CONTROL

CROSS-REFERENCE TO RELATED APPLICATION

This application is a Section 371 of International Application No. PCT/JP2014/084754, filed Dec. 25, 2014, which was published in the Japanese language on Jul. 9, 2015, under International Publication No. WO 2015/102104 A1, and the disclosure of which is incorporated herein by reference in its entirety.

TECHNICAL FIELD

The present invention relates to a thiazole compound and its use in pest control.

BACKGROUND ART

Heretofore, compounds having a control activity against pests were found as active ingredients of a pest control agent, and have been developed.

In addition, as active ingredients of a pest control agent, thiazole compounds represented by the following Formulas (A-1) to (A-3) are known (refer to Patent Citation 1).

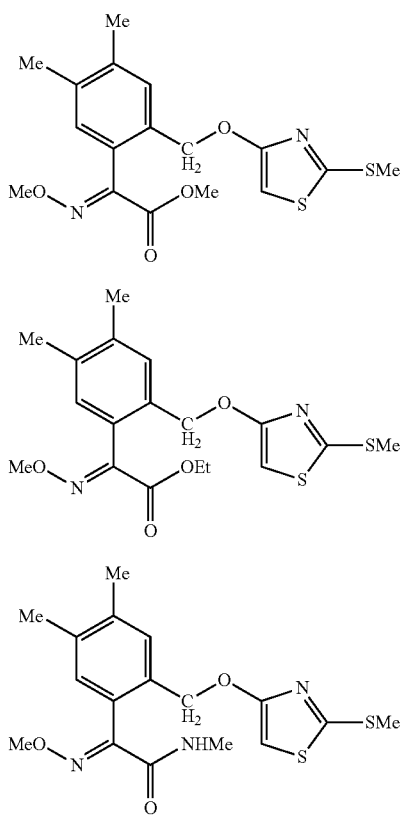

[Patent Citation 1] WO 2000/003974 pamphlet

DISCLOSURE OF INVENTION

An object of the present invention is to provide a novel compound having control activity against pests.

The present inventors have studied to find a compound having control activity against pests, and as a result, has found that a thiazole compound represented by the following Formula (1) has controlling efficacy against pests, and completed the present invention.

That is, the invention is as follows.

[1] A thiazole compound represented by Formula (1):

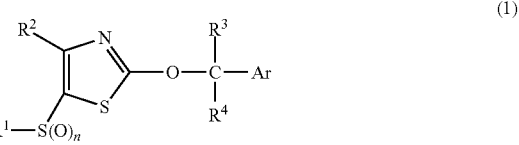

wherein $R^1$ represents a C1-C4 alkyl group optionally having one or more fluorine atoms, $R^2$ represents a C1-C4 alkyl group optionally having one or more fluorine atoms or a hydrogen atom, $R^3$ and $R^4$ are the same or different and each represents a hydrogen atom, a C3-C6 cycloalkyl group, or a C1-C4 alkyl group optionally having one or more fluorine atoms, Ar represents a phenyl group optionally having one or more atoms or groups selected from the group A, a naphthyl group optionally having one or more atoms or groups selected from the group A, or a 5- or 6-membered heteroaryl group optionally having one or more atoms or groups selected from the group A, and n represents 0, 1, or 2, Group A is a group consisting of a C1-C4 alkyl group optionally having one or more fluorine atoms, a C2-C4 alkenyl group, a C2-C4 alkynyl group, a C1-C4 alkoxy group optionally having one or more fluorine atoms, a C2-C4 alkenyloxy group, a C2-C4 alkynyloxy group, a C1-C4 alkylthio group optionally having one or more fluorine atoms, a C1-C4 alkylsulfinyl group optionally having one or more fluorine atoms, a C1-C4 alkylsulfonyl group optionally having one or more fluorine atoms, a phenyl group optionally having one or more atoms or groups selected from the group B, a phenoxy group optionally having one or more atoms or groups selected from the group B, a formyl group, a (C1-C3 alkyl) carbonyl group, a benzoyl group, a (C1-C3 alkoxy) C1-C3 alkyl group, a (C1-C3 alkoxy) carbonyl group, a hydroxy group, a cyano group, a nitro group, a di(C1-C3 alkyl) amino group, and a halogen atom, Group B is a group consisting of a halogen atom, a methyl group, a trifluoromethyl group, a methoxy group, and a trifluoromethoxy group.

[2] The thiazole compound according to [1], wherein, in Formula (1), $R^1$ is a C1-C3 alkyl group, $R^2$ is a hydrogen atom or a C1-C3 alkyl group, $R^3$ and $R^4$ are the same or different and each represents a hydrogen atom or a C1-C3 alkyl group, and Ar is a phenyl group optionally having one or more atoms or groups selected from the group A, a naphthyl group optionally having one or more atoms or groups selected from the group A, a pyridyl group optionally having one or more atoms or groups selected from the group A, a thienyl group optionally having one or more atoms or groups selected from the group A, a furyl group optionally having one or more atoms or groups selected from the group A, or a pyrrolyl group optionally having one or more atoms or groups selected from the group A.

[3] The thiazole compound according to [1], wherein, in Formula (1), $R^1$ represents a methyl group or an ethyl group, $R^2$ represents a hydrogen atom, $R^3$ represents a hydrogen atom, R⁴ represents a hydrogen atom or a methyl group, Ar is a phenyl group optionally having one or more atoms or groups selected from the group C, a naphthyl group optionally having one or more atoms or groups selected from the group C, a pyridyl group optionally having one or more atoms or groups selected from the group C, a thienyl group optionally having one or more atoms or groups selected from the group C, or a furyl group optionally having one or more atoms or groups selected from the group C, n is 0 or 1, and the group C is the group consisting of a halogen atom, a methyl group, an ethyl group, a methoxy group, and an ethoxy group.

[4] A pest control agent comprising the thiazole compound according to any one of [1] to [3] and an inert carrier.

[5] A method for controlling pests comprising applying an effective amount of the thiazole compound according to any one of [1] to [3] to pests or a habitat of the pests.

EFFECT OF INVENTION

The compound of the present invention has a control activity against pests and is effective as active ingredients of a pest control agent.

MODE FOR CARRYING OUT THE INVENTION

In the present specification, examples of the halogen atom include a fluorine atom, a chlorine atom, a bromine atom, and an iodine atom.

In the present specification, examples of the C1-C4 alkyl group optionally having one or more fluorine atoms include a methyl group, an ethyl group, a propyl group, an isopropyl group, a butyl group, an isobutyl group, an s-butyl group, a t-butyl group, a fluoromethyl group, a difluoromethyl group, a trifluoromethyl group, a 1-fluoroethyl group, a 1,1-difluoroethyl group, a 2,2,2-trifluoroethyl group, a pentafluoroethyl group, a heptafluoropropyl group, a 1-trifluoromethylethyl group, a 1,2,2,2-tetrafluoro-1-trifluoromethylethyl group, a 4,4,4-trifluorobutyl group, a 3,3,3-trifluoro-2-trifluoromethylpropyl group, and a nonafluorobutyl group.

In the present specification, examples of the C3-C6 cycloalkyl group include a cyclopropyl group, a cyclobutyl group, a cyclopentyl group, and a cyclohexyl group.

In the present specification, the 5- or 6-membered heteroaryl group in the 5- or 6-membered heteroaryl group optionally having one or more atoms or groups selected from the group A represents a 5- or 6-membered aromatic heterocyclic group including one or more oxygen atoms, nitrogen atoms, and/or sulfur atoms, as a ring constituent element, and examples thereof include a pyrrolyl group, an imidazolyl group, a pyrazolyl group, a triazolyl group, a tetrazolyl group, an oxazolyl group, an isoxazolyl group, an oxadiazolyl group, a thiazolyl group, an isothiazolyl group, a thiadiazolyl group, a furyl group, a thienyl group, a pyridyl group, a pyrimidinyl group, a pyrazinyl group, a pyridazinyl group, and a triazinyl group.

In the present specification, examples of the 5- or 6-membered heteroaryl group optionally having one or more atoms or groups selected from the group A include a 5-imidazolyl group, a 3-pyrazolyl group, a 3-(4H-1,2,4-triazolyl) group, a 5-(1H-1,2,3-triazolyl) group, a 4-(2H-1,2,3-triazolyl) group, a 1H-tetrazolyl group, a 2H-tetrazolyl group, a 4-oxazolyl group, a 5-isoxazolyl group, a 3-(1,2,4-oxadiazolyl) group, a 2-(1,3,4-oxadiazolyl) group, a 3-(1,2,5-oxadiazolyl) group, a 4-thiazolyl group, a 3-isothiazolyl group, a 4-(1,2,3-thiadiazolyl) group, a 5-(1,2,4-thiadiazolyl) group, a 2-(1,3,4-thiadiazolyl) group), a 4-(1,2,5-thiadiazolyl) group, a 2-pyrimidinyl group, a 4-pyrimidinyl group, a 5-pyrimidinyl group, a 3-pyrazinyl group, a 5-pyridazinyl group, a 4-(1,3,5-triazinyl) group, a 3-(1,2,4-triazinyl) group, a 2-pyridyl group, a 3-pyridyl group, a 4-pyridyl group, a 5-chloro-2-pyridyl group, a 6-chloro-2-pyridyl group, a 2-methyl-3-pyridyl group, a 4-methyl-3-pyridyl group, a 3-methyl-2-pyridyl group, a 5-methyl-2-pyridyl group, a 5-methoxy-2-pyridyl group, a 4-trifluoromethyl-3-pyridyl group, a 6-ethyl-3-pyridyl group, a 2-methoxy-3-pyridyl group, a 2-ethoxy-3-pyridyl group, a 6-methoxy-3-pyridyl group, a 6-trifluoromethoxy-3-pyridyl group, a 5-vinyl-2-pyridyl group, a 3-methyl-4-pyridyl group, a 3-(2-butynyl)-4-pyridyl group, a 2-formyl-3-pyridyl group, a 6-(2-butenyloxy)-2-pyridyl group, a 5-(3-butynyloxy)-3-pyridyl group, a 3-ethylthio-4-pyridyl group, a 4-isopropylsulfinyl-2-pyridyl group, a 4-ethylsulfonyl-3-pyridyl group, a 3-phenyl-2-pyridyl group, a 6-phenoxy-4-pyridyl group, a 1-isopropoxymethyl-2-pyridyl group, a 5-methoxycarbonyl-2-pyridyl group, a 5-hydroxy-4-pyridyl group, a 6-cyano-3-pyridyl group, a 4-nitro-2-pyridyl group, a 5-diethylamino-2-pyridyl group, a 2-fluoro-6-methyl-3-pyridyl group, a 2,6-dichloro-4-pyridyl group, a 2-thienyl group, a 3-thienyl group, a 3-methyl-2-thienyl group, a 4-methyl-2-thienyl group, a 5-methyl-2-thienyl group, a 3-methoxy-2-thienyl group, a 4-ethoxy-2-thienyl group, a 5-methoxy-2-thienyl group, a 2-ethyl-3-thienyl group, a 4-fluoro-3-thienyl group, a 5-methyl-3-thienyl group, a 2-methoxy-3-thienyl group, a 4-chloro-3-thienyl group, a 4-methoxy-3-thienyl group, a 5-methoxy-3-thienyl group, a 4-(2-propenyl)-3-thienyl group, a 4-(2-butynyl)-3-thienyl group, a 3-formyl-2-thienyl group, a 4-(2-butenyloxy)-3-thienyl group, a 3-(2-propynyloxy)-2-thienyl group, a 4-ethylthio-3-thienyl group, a 2-propylsulfinyl-3-thienyl group, a 5-methylsulfonyl-2-thienyl group, a 4-phenyl-3-thienyl group, a 4-phenoxy-3-thienyl group, a 4-methoxymethyl-3-thienyl group, a 2-ethoxycarbonyl-3-thienyl group, a 3-hydroxy-2-thienyl group, a 5-cyano-2-thienyl group, a 5-nitro-3-thienyl group, a 3-diethylamino-2-thienyl group, a 2-methyl-3-thienyl group, a 4-methyl-3-thienyl group, a 4,5-dimethyl-2-thienyl group, a 2-furyl group, a 3-furyl group, a 3-methyl-2-furyl group, a 4-methyl-2-furyl group, a 4-vinyl-2-furyl group, a 5-ethynyl-3-furyl group, a 3-fluoro-2-furyl group, a 4-methoxy-2-furyl group, a 5-ethoxy-2-furyl group, a 2-ethyl-3-furyl group, a 2-methyl-3-furyl group, a 4-methyl-3-furyl group, a 5-methyl-3-furyl group, a 2-methoxy-3-furyl group, a 3-vinyl-2-furyl group, a 4-(1-methyl-2-propynyl)-3-furyl group, a 3-formyl-2-furyl group, a 4-(2-propenyloxy)-3-furyl group, a 3-(2-butynyloxy)-2-furyl group, a 4-propylthio-3-furyl group, a 2-methylsulfinyl-3-furyl group, a 5-ethylsulfonyl-2-furyl group, a 5-phenyl-3-furyl group, a 3-phenoxy-2-furyl group, a 4-ethoxymethyl-3-furyl group, a 2-isopropoxycarbonyl-3-furyl group, a 3-hydroxy-2-furyl group, a 5-cyano-2-furyl group, a 5-nitro-3-furyl group, a 3-dipropylamino-2-furyl group, a 4-chloro-2-trifluoromethyl-3-furyl group, a 2-pyrrolyl group, a 3-pyrrolyl group, a 1-methyl-2-pyrrolyl group, a 1-methyl-3-pyrrolyl group, a 3-methyl-2-pyrrolyl group, a 4-methyl-2-pyrrolyl group, a 4-vinyl-2-pyrrolyl group, a 5-ethynyl-3-pyrrolyl group, a 3-fluoro-2-pyrrolyl group, a 5-ethoxy-2-pyrrolyl group, a 2-ethyl-3-pyrrolyl group, a 4-methyl-3-pyrrolyl group, a 5-methyl-3-pyrrolyl group, a 2-methoxy-3-pyrrolyl group, a 3-vinyl-2-pyrrolyl group, a 4-(1-methyl-2-propynyl)-3-pyrrolyl group, a 3-formyl-2-pyrrolyl group, a 4-(2-propenyloxy)-3-pyrrolyl group, a 3-(2-butynyloxy)-2-pyrrolyl group, a 4-ethylthio-3-pyrrolyl group, a 2-isopropylsulfinyl-3-pyrrolyl group, a 5-methylsulfonyl-2-pyrrolyl group, a 5-phenyl-2-pyrrolyl group, a 3-phenoxy-2-pyrrolyl group, a 4-ethoxymethyl-3-pyrrolyl group, a 2-methoxycarbonyl-3-pyrrolyl group, a 3-hydroxy-2-pyrrolyl group, a 5-cyano-2-pyrrolyl group, a 5-nitro-3-pyrrolyl group, a 3-diisopropylamino-2-pyrrolyl group, a 1-methyl-5-trifluoromethyl-2-pyrrolyl group, a 3-chloro-5-methoxy-2-pyrrolyl group, and a 1-methyl-5-trifluoromethyl-2-pyrrolyl group.

In the present specification, examples of the C2-C4 alkenyl group include a vinyl group, a 1-propenyl group, a 2-propenyl group, a 1-methyl-2-propenyl group, a 2-methyl-2-propenyl group, a 1-butenyl group, a 2-butenyl group, and a 3-butenyl group.

In the present specification, examples of the C2-C4 alkynyl group include an ethynyl group, a 1-propynyl group, a 2-propynyl group, a 1-methyl-2-propynyl group, a 1-butynyl group, a 2-butynyl group, and a 3-butynyl group.

In the present specification, examples of the C1-C4 alkoxy group optionally having one or more fluorine atoms include a methoxy group, an ethoxy group, a propoxy group, an isopropoxy group, a butoxy group, an isobutoxy group, an s-butoxy group, a t-butoxy group, a fluoromethoxy group, a difluoromethoxy group, a trifluoromethoxy group, a 1-fluoroethoxy group, a 1,1-difluoroethoxy group, a 2,2,2-trifluoroethoxy group, a pentafluoroethoxy group, a heptafluoropropoxy group, a 1-trifluoromethylethoxy group, a 1,2,2,2-tetrafluoro-1-trifluoromethylethoxy group, a 4,4,4-trifluorobutoxy group, a 3,3,3-trifluoro-2-trifluoromethylpropoxy group, and a nonafluorobutoxy group.

In the present specification, examples of the C2-C4 alkenyloxy group include a vinyloxy group, a 1-propenyloxy group, a 2-propenyloxy group, a 1-methyl-2-propenyloxy group, a 2-methyl-2-propenyloxy group, a 1-butenyloxy group, a 2-butenyloxy group, and a 3-butenyloxy group.

In the present specification, examples of the C2-C4 alkynyloxy group include an ethynyloxy group, a 1-propynyloxy group, a 2-propynyloxy group, a 1-methyl-2-propynyloxy group, a 1-butynyloxy group, a 2-butynyloxy group, and a 3-butynyloxy group.

In the present specification, examples of the C1-C4 alkylthio group optionally having one or more fluorine atoms include a methylthio group, an ethylthio group, a propylthio group, an isopropylthio group, a butylthio group, an isobutylthio group, an s-butylthio group, a t-butylthio group, a fluoromethylthio group, a difluoromethylthio group, a trifluoromethylthio group, a 1-fluoroethylthio group, a 1,1-difluoroethylthio group, a 2,2,2-trifluoroethylthio group, a pentafluoroethylthio group, a heptafluoropropylthio group, a 1-trifluoromethylethylthio group, a 1,2,2,2-tetrafluoro-1-trifluoromethylethylthio group, a 4,4,4-trifluorobutylthio group, a 3,3,3-trifluoro-2-trifluoromethylpropylthio group, and a nonafluorobutylthio group.

In the present specification, examples of the C1-C4 alkylsulfinyl group optionally having one or more fluorine atoms include a methylsulfinyl group, an ethylsulfinyl group, a propylsulfinyl group, an isopropylsulfinyl group, a butylsulfinyl group, an isobutylsulfinyl group, an s-butylsulfinyl group, a t-butylsulfinyl group, a fluoromethylsulfinyl group, a difluoromethylsulfinyl group, a trifluoromethylsulfinyl group, a 1-fluoroethylsulfinyl group, a 1,1-difluoroethylsulfinyl group, a 2,2,2-trifluoroethylsulfinyl group, a pentafluoroethylsulfinyl group, a heptafluoropropylsulfinyl group, a 1-trifluoromethylethylsulfinyl group, a 1,2,2,2-tetrafluoro-1-trifluoromethylethylsulfinyl group, a 4,4,4-trifluorobutylsulfinyl group, a 3,3,3-trifluoro-2-trifluoromethylpropylsulfinyl group, and a nonafluorobutylsulfinyl group.

In the present specification, examples of the C1-C4 alkylsulfonyl group optionally having one or more fluorine atoms include a methylsulfonyl group, an ethylsulfonyl group, a propylsulfonyl group, an isopropylsulfonyl group, a butylsulfonyl group, an isobutylsulfonyl group, an s-butylsulfonyl group, a t-butylsulfonyl group, a fluoromethylsulfonyl group, a difluoromethylsulfonyl group, a trifluoromethylsulfonyl group, a 1-fluoroethylsulfonyl group, a 1,1-difluoroethylsulfonyl group, a 2,2,2-trifluoroethylsulfonyl group, a pentafluoroethylsulfonyl group, a heptafluoropropylsulfonyl group, a 1-trifluoromethylethylsulfonyl group, a 1,2,2,2-tetrafluoro-1-trifluoromethylethylsulfonyl group, a 4,4,4-trifluorobutylsulfonyl group, a 3,3,3-trifluoro-2-trifluoromethylpropylsulfonyl group, and a nonafluorobutylsulfonyl group.

In the present specification, examples of the (C1-C3 alkyl) carbonyl group include an acetyl group, a propionyl group, a butyryl group, and an isobutyryl group.

In the present specification, examples of the (C1-C3 alkoxy) C1-C3 alkyl group include a methoxymethyl group, an ethoxymethyl group, a propoxymethyl group, an isopropoxymethyl group, a 2-methoxyethyl group, a 2-methoxy-1-methylethyl group, a 2-methoxypropyl group, a 3-methoxypropyl group, and a 2-isopropoxy-1-methylethyl group.

In the present specification, examples of the (C1-C3 alkoxy) carbonyl group include a methoxycarbonyl group, an ethoxycarbonyl group, a propoxycarbonyl group, and an isopropoxycarbonyl group.

In the present specification, examples of the di(C1-C3 alkyl) amino group include a dimethylamino group, a methylethylamino group, a diethylamino group, and a diisopropylamino group.

In the present specification, examples of the C1-C3 alkyl group include a methyl group, an ethyl group, a propyl group, and an isopropyl group.

In the present specification, examples of the phenyl group optionally having one or more atoms or groups selected from the group A include a phenyl group, a 2-chlorophenyl group, a 3-chlorophenyl group, a 4-chlorophenyl group, a 2-bromophenyl group, a 3-bromophenyl group, a 2-fluorophenyl group, a 3-fluorophenyl group, a 4-fluorophenyl group, a 4-iodophenyl group, a 2-chloro-3-fluorophenyl group, a 2,3-dichlorophenyl group, a 2,4-dichlorophenyl group, a 2,5-dichlorophenyl group, a 2,6-dichlorophenyl group, a 2,3-difluorophenyl group, a 2,4-difluorophenyl group, a 2,5-difluorophenyl group, a 2,6-difluorophenyl group, a 2,4,6-trifluorophenyl group, a 2,3,5,6-tetrafluorophenyl group, a 2,3,4,5,6-pentafluorophenyl group, a 2-methylphenyl group, a 2-trifluoromethylphenyl group, a 3-trifluoromethylphenyl group, a 2-trifluoromethoxyphenyl group, a 4-methylphenyl group, a 2-t-butylphenyl group, a 4-t-butylphenyl group, a 2-(2,2,2-trifluoroethyl)phenyl group, a 4-(2,2,2-trifluoroethyl)phenyl group, a 3-isopropylphenyl group, a 2-ethylphenyl group, a 2-propylphenyl group, a 2-isopropylphenyl group, a 2-methoxyphenyl group, a 2-ethoxyphenyl group, a 2-propoxymethylphenyl group, a 2-isopropoxyphenyl group, a 2-(2,2,2-trifluoroethoxy)phenyl group, a 2-vinylphenyl group, a 2-(1-propenyl)phenyl group, a 3-(2-propenyl)phenyl group, a 3-formylphenyl group, a 4-(2-propenyloxy)phenyl group, a 3-(3-butynyloxy)phenyl group, a 2-methylthiophenyl group, a 3-propylsulfinylphenyl group, a 4-isopropylsulfonylphenyl group, a 2-phenylphenyl group, a 3-phenylphenyl group, a 3-phenoxyphenyl group, a 4-phenoxyphenyl group, a 2-methoxymethylphenyl group, a 3-isopropoxycarbonylphenyl group, a 4-hydroxyphenyl group, a 2-cyanophenyl group, a 3-cyanophenyl group, a 2-nitrophenyl group, a 2-dimethylaminophenyl group, a 3-dimethylaminophenyl group, a 2,3-dimethylphenyl group, a 2,4-dimethylphenyl group, a 2,5-dimethylphenyl group, a 2,6-dimethylphenyl group, a 2,4-bis(trifluoromethyl)phenyl group, a 2-methyl-5-trifluoromethylphenyl group, a 2,4,6-trimethylphenyl group, a 2,4,6-trimethoxyphenyl group, a 2-fluoro-6-methylphenyl group, a 3-fluoro-2-methylphenyl group, a 4-fluoro-2-methylphenyl group, a 5-fluoro-2-methylphenyl group, a 5-fluoro-2-ethylphenyl group, a 2-fluoro-6-trifluoromethoxyphenyl group, a 3-chloro-2-methoxyphenyl group, a 2-fluoro-6-methoxyphenyl group, a 3-fluoro-2-methoxyphenyl group, a 4-fluoro-2-methoxyphenyl group, a 5-fluoro-2-methoxyphenyl group, a 5-fluoro-2-ethoxyphenyl group, a 2,5-dimethoxyphenyl group, a 2-chloro-6-methylphenyl group, a 3-chloro-2-methylphenyl group, a 4-chloro-2-methylphenyl group, a 5-chloro-2-methylphenyl group, a 4-chloro-2-methoxyphenyl group, a 5-chloro-2-methoxyphenyl group, a 5-ethoxy-2-methoxyphenyl group, a 3-methoxy-2-methylphenyl group, a 4-methoxy-2-methylphenyl group, and a 5-methoxy-2-methylphenyl group.

In the present specification, examples of the phenyl group optionally having one or more atoms or groups selected from the group B include a phenyl group, a 2-chlorophenyl group, a 3-bromophenyl group, a 4-fluorophenyl group, a 2-chloro-3-fluorophenyl group, a 2,4-dichlorophenyl group, a 2,4,6-trifluorophenyl group, a 2,3,5,6-tetrafluorophenyl group, a 2,3,4,5,6-pentafluorophenyl group, a 2-methylphenyl group, a 3-methylphenyl group, a 4-methylphenyl group, a 3-isopropylphenyl group, a 2,4-dimethylphenyl group, a 2,4,6-trimethylphenyl group, a 2-methoxyphenyl group, a 4-trifluoromethoxyphenyl group, a 5-chloro-2-methoxyphenyl group, a 2-fluoro-4-trifluoromethylphenyl group, and a 2-fluoro-6-methylphenyl group.

In the present specification, examples of the phenyl group optionally having one or more atoms or groups selected from the group C include a 2-chlorophenyl group, a 2-bromophenyl group, a 3-bromophenyl group, a 2-fluorophenyl group, a 3-fluorophenyl group, a 4-fluorophenyl group, a 4-iodophenyl group, a 2-chloro-3-fluorophenyl group, a 2,4-dichlorophenyl group, a 2,4,6-trifluorophenyl group, a 2,3,5,6-tetrafluorophenyl group, a 2,3,4,5,6-pentafluorophenyl group, a 2-ethylphenyl group, a 2-methoxyphenyl group, a 2-ethoxyphenyl group, a 2-methylphenyl group, a 3-methylphenyl group, a 4-methylphenyl group, a 3-ethylphenyl group, a 2,4-dimethylphenyl group, a 2,5-dimethylphenyl group, a 2,4,6-trimethylphenyl group, a 2-fluoro-6-methylphenyl group, a 3-fluoro-2-methylphenyl group, a 4-fluoro-2-methylphenyl group, a 5-fluoro-2-methylphenyl group, a 5-fluoro-2-ethylphenyl group, a 2-fluoro-6-methoxyphenyl group, a 3-chloro-2-methoxyphenyl group, a 3-fluoro-2-methoxyphenyl group, a 4-fluoro-2-methoxyphenyl group, a 5-fluoro-2-methoxyphenyl group, a 5-fluoro-2-ethoxyphenyl group, a 2,5-dimethoxyphenyl group, a 5-chloro-2-methylphenyl group, a 4-chloro-2-methoxyphenyl group, a 5-chloro-2-methoxyphenyl group, a 5-ethoxy-2-methoxyphenyl group, a 2-methoxy-3-methylphenyl group, a 2-methoxy-4-methylphenyl group, a 2-methoxy-5-methylphenyl group, a 2-methoxy-6-methylphenyl group, and a 5-methoxy-2-methylphenyl group.

In the present specification, examples of the phenoxy group optionally having one or more atoms or groups selected from the group B include a phenoxy group, a 2-chlorophenoxy group, a 3-bromophenoxy group, a 4-fluorophenoxy group, a 2-chloro-3-fluorophenoxy group, a 2,4-dichlorophenoxy group, a 2,4,6-trifluorophenoxy group, a 2-methylphenoxy group, a 3-methylphenoxy group, a 4-methylphenoxy group, a 3-isopropylphenoxy group, a 2,4-dimethylphenoxy group, a 2,4,6-trimethylphenoxy group, a 2-methoxyphenoxy group, a 4-trifluoromethoxyphenoxy group, a 3-fluoro-5-methoxyphenoxy group, a 4-chloro-2-trifluoromethylphenoxy group, and a 2-fluoro-6-methylphenoxy group.

In the present specification, examples of the naphthyl group optionally having one or more atoms or groups selected from the group A include a 1-naphthyl group, a 2-naphthyl group, a 2-methyl-1-naphthyl group, a 2-methoxy-1-naphthyl group, a 1-methoxy-2-naphthyl group, a 5-methoxy-2-naphthyl group, a 6-trifluoromethyl-2-naphthyl group, a 3-methyl-2-naphthyl group, a 3-ethoxy-2-naphthyl group, a 2-chloro-1-naphthyl group, a 1-fluoro-2-naphthyl group, a 5-(2-propenyl)-2-naphthyl group, a 3-(2-butynyl)-1-naphthyl group, a 8-formyl-2-naphthyl group, a 6-(2-propenyloxy)-2-naphthyl group, a 5-(2-butynyloxy)-1-naphthyl group, a 1-methylthio-2-naphthyl group, a 7-propylsulfinyl-2-naphthyl group, a 4-isopropylsulfonyl-1-naphthyl group, a 3-phenyl-2-naphthyl group, a 6-phenoxy-1-naphthyl group, a 1-ethoxymethyl-2-naphthyl group, a 3-isopropoxycarbonyl-2-naphthyl group, a 4-hydroxy-1-naphthyl group, a 6-cyano-1-naphthyl group, a 2-nitro-1-naphthyl group, a 5-ethylmethylamino-2-naphthyl group, a 2-chloro-6-methyl-1-naphthyl group, a 8-chloro-6-methoxy-1-naphthyl group, and a 7-fluoro-2-trifluoromethyl-1-naphthyl group.

In the present specification, examples of the naphthyl group optionally having one or more atoms or groups selected from the group C include a 1-naphthyl group, a 2-naphthyl group, a 2-methyl-1-naphthyl group, a 2-methoxy-1-naphthyl group, a 6-methyl-2-naphthyl group, a 1-methoxy-2-naphthyl group, a 5-methoxy-2-naphthyl group, a 3-methyl-2-naphthyl group, a 3-ethoxy-2-naphthyl group, a 2-chloro-1-naphthyl group, a 1-fluoro-2-naphthyl group, a 8-chloro-6-methoxy-1-naphthyl group, and a 2-chloro-6-methyl-1-naphthyl group.

In the present specification, examples of the pyridyl group optionally having one or more atoms or groups selected from the group A include a 2-pyridyl group, a 3-pyridyl group, a 4-pyridyl group, a 5-chloro-2-pyridyl group, a 6-chloro-2-pyridyl group, a 2-methyl-3-pyridyl group, a 4-methyl-3-pyridyl group, a 3-methyl-2-pyridyl group, a 5-methyl-2-pyridyl group, a 5-methoxy-2-pyridyl group, a 6-chloro-3-pyridyl group, a 5-chloro-3-pyridyl group, a 4-trifluoromethyl-3-pyridyl group, a 6-ethyl-3-pyridyl group, a 2-methoxy-3-pyridyl group, a 2-ethoxy-3-pyridyl group, a 6-methoxy-3-pyridyl group, a 6-trifluoromethoxy-3-pyridyl group, a 5-vinyl-2-pyridyl group, a 3-methyl-4-pyridyl group, a 3-(2-butynyl)-4-pyridyl group, a 2-formyl-3-pyridyl group, a 6-(2-butenyloxy)-2-pyridyl group, a 5-(3-butynyloxy)-3-pyridyl group, a 3-ethylthio-4-pyridyl group, a 4-isopropylsulfinyl-2-pyridyl group, a 4-ethylsulfonyl-3-pyridyl group, a 3-phenyl-2-pyridyl group, a 6-phenoxy-4-pyridyl group, a 1-isopropoxymethyl-2-pyridyl group, a 5-methoxycarbonyl-2-pyridyl group, a 5-hydroxy-4-pyridyl group, a 6-cyano-3-pyridyl group, a 4-nitro-2-pyridyl group, a 5-diethylamino-2-pyridyl group, a 5,6-difluoro-3-pyridyl group, a 2-fluoro-6-methyl-3-pyridyl group, and a 2,6-dichloro-4-pyridyl group.

In the present specification, examples of the pyridyl group optionally having one or more atoms or groups selected from the group C include a 2-pyridyl group, a 3-pyridyl group, a 4-pyridyl group, a 5-chloro-2-pyridyl group, a 6-chloro-2-pyridyl group, a 3-methyl-2-pyridyl group, a 5-methyl-2-pyridyl group, a 5-methoxy-2-pyridyl group, a 6-chloro-3-pyridyl group, a 5-chloro-3-pyridyl group, a 2-methyl-3-pyridyl group, a 4-methyl-3-pyridyl group, a 6-ethyl-3-pyridyl group, a 2-methoxy-3-pyridyl group, a 2-ethoxy-3-pyridyl group, a 6-methoxy-3-pyridyl group, a 5,6-difluoro-3-pyridyl group, a 2-fluoro-6-methyl-3-pyridyl group, a 3-methyl-4-pyridyl group, and a 2,6-dichloro-4-pyridyl group.

In the present specification, examples of the thienyl group optionally having one or more atoms or groups selected from the group A include a 2-thienyl group, a 3-thienyl group, a 3-methyl-2-thienyl group, a 4-methyl-2-thienyl group, a 5-methyl-2-thienyl group, a 3-methoxy-2-thienyl group, a 4-ethoxy-2-thienyl group, a 5-methoxy-2-thienyl group, a 2-ethyl-3-thienyl group, a 4-fluoro-3-thienyl group, a 5-methyl-3-thienyl group, a 2-methoxy-3-thienyl group, a 4-chloro-3-thienyl group, a 4-methoxy-3-thienyl group, a 5-methoxy-3-thienyl group, a 4-(2-propenyl)-3-thienyl group, a 4-(2-butynyl)-3-thienyl group, a 3-formyl-2-thienyl group, a 4-(2-butenyloxy)-3-thienyl group, a 3-(2-propynyloxy)-2-thienyl group, a 4-ethylthio-3-thienyl group, a 2-propylsulfinyl-3-thienyl group, a 5-methylsulfonyl-2-thienyl group, a 4-phenyl-3-thienyl group, a 4-phenoxy-3-thienyl group, a 4-methoxymethyl-3-thienyl group, a 2-ethoxycarbonyl-3-thienyl group, a 3-hydroxy-2-thienyl group, a 5-cyano-2-thienyl group, a 5-nitro-3-thienyl group, a 3-diethylamino-2-thienyl group, a 2-methyl-3-thienyl group, a 4-methyl-3-thienyl group, a 4-ethoxy-2-methyl-3-thienyl group, and a 4,5-dimethyl-2-thienyl group.

In the present specification, examples of the thienyl group optionally having one or more atoms or groups selected from the group C include a 2-thienyl group, a 3-thienyl group, a 3-methyl-2-thienyl group, a 4-methyl-2-thienyl group, a 5-methyl-2-thienyl group, a 3-methoxy-2-thienyl group, a 4-ethoxy-2-thienyl group, a 5-methoxy-2-thienyl group, a 2-ethyl-3-thienyl group, a 4-fluoro-3-thienyl group, a 5-methyl-3-thienyl group, a 2-methoxy-3-thienyl group, a 4-chloro-3-thienyl group, a 4-methoxy-3-thienyl group, a 5-methoxy-3-thienyl group, a 2-methyl-3-thienyl group, a 4-methyl-3-thienyl group, a 5-fluoro-2-ethoxy-3-thienyl group, and a 4,5-dimethyl-2-thienyl group.

In the present specification, examples of the furyl group optionally having one or more atoms or groups selected from the group A include a 2-furyl group, a 3-furyl group, a 3-methyl-2-furyl group, a 4-methyl-2-furyl group, a 5-methyl-2-furyl group, a 4-vinyl-2-furyl group, a 5-ethynyl-3-furyl group, a 3-fluoro-2-furyl group, a 4-methoxy-2-furyl group, a 5-ethoxy-2-furyl group, a 2-ethyl-3-furyl group, a 2-methyl-3-furyl group, a 4-methyl-3-furyl group, a 5-methyl-3-furyl group, a 2-methoxy-3-furyl group, a 3-vinyl-2-furyl group, a 4-(1-methyl-2-propynyl)-3-furyl group, a 3-formyl-2-furyl group, a 4-(2-propenyloxy)-3-furyl group, a 3-(2-butynyloxy)-2-furyl group, a 4-propylthio-3-furyl group, a 2-methylsulfinyl-3-furyl group, a 5-ethylsulfonyl-2-furyl group, a 5-phenyl-3-furyl group, a 3-phenoxy-2-furyl group, a 4-ethoxymethyl-3-furyl group, a 2-isopropoxycarbonyl-3-furyl group, a 3-hydroxy-2-furyl group, a 5-cyano-2-furyl group, a 5-nitro-3-furyl group, a 3-dipropylamino-2-furyl group, a 2-ethyl-3-furyl group, a 4-chloro-2-trifluoromethyl-3-furyl group, and a 2,5-dimethyl-3-furyl group.

In the present specification, examples of the furyl group optionally having one or more atoms or groups selected from the group C include a 2-furyl group, a 3-furyl group, a 3-methyl-2-furyl group, a 4-methyl-2-furyl group, a 5-methyl-2-furyl group, a 4-methyl-2-furyl group, a 3-fluoro-2-furyl group, a 4-methoxy-2-furyl group, a 5-ethoxy-2-furyl group, a 2-ethyl-3-furyl group, a 2-methyl-3-furyl group, a 4-methyl-3-furyl group, a 5-methyl-3-furyl group, a 2-methoxy-3-furyl group, a 4-ethoxy-3-furyl group, a 5-methoxy-3-furyl group, a 2-ethyl-3-furyl group, a 4-chloro-2-trifluoromethoxy-3-furyl group, and a 2,5-dimethyl-3-furyl group.

In the present specification, examples of the pyrrolyl group optionally having one or more atoms or groups selected from the group A include a 2-pyrrolyl group, a 3-pyrrolyl group, a 1-methyl-2-pyrrolyl group, a 1-methyl-3-pyrrolyl group, a 3-methyl-2-pyrrolyl group, a 4-methyl-2-pyrrolyl group, a 5-methyl-2-pyrrolyl group, a 4-vinyl-2-pyrrolyl group, a 5-ethynyl-3-pyrrolyl group, a 3-fluoro-2-pyrrolyl group, a 4-methoxy-2-pyrrolyl group, a 5-ethoxy-2-pyrrolyl group, a 2-ethyl-3-pyrrolyl group, a 4-methyl-3-pyrrolyl group, a 5-methyl-3-pyrrolyl group, a 2-methoxy-3-pyrrolyl group, a 3-vinyl-2-pyrrolyl group, a 4-(1-methyl-2-propynyl)-3-pyrrolyl group, a 3-formyl-2-pyrrolyl group, a 4-(2-propenyloxy)-3-pyrrolyl group, a 3-(2-butynyloxy)-2-pyrrolyl group, a 4-ethylthio-3-pyrrolyl group, a 2-isopropylsulfinyl-3-pyrrolyl group, a 5-methylsulfonyl-2-pyrrolyl group, a 5-phenyl-3-pyrrolyl group, a 3-phenoxy-2-pyrrolyl group, a 4-ethoxymethyl-3-pyrrolyl group, a 2-methoxycarbonyl-3-pyrrolyl group, a 3-hydroxy-2-pyrrolyl group, a 5-cyano-2-pyrrolyl group, a 5-nitro-3-pyrrolyl group, a 3-diisopropylamino-2-pyrrolyl group, a 1-methyl-5-trifluoromethyl-2-pyrrolyl group, a 1-methyl-5-pentafluoroethoxy-2-pyrrolyl group, a 3-chloro-5-methoxy-2-pyrrolyl group, a 1-methyl-5-trifluoromethyl-2-pyrrolyl group, and a 1-methyl-2-ethyl-3-pyrrolyl group.

In the present specification, the leaving group represents a halogen atom, an alkylsulfonyloxy group, an arylsulfonyloxy group, an alkylsulfonyl group, or an arylsulfonyl group, and examples thereof include halogen atoms such as a fluorine atom, a chlorine atom, a bromine atom, and an iodine atom, alkylsulfonyloxy groups such as a methylsulfonyloxy group and a trifluoromethylsulfonyloxy group, arylsulfonyloxy groups such as a phenylsulfonyloxy group and a 4-methylphenylsulfonyloxy group, alkylsulfonyl groups such as a methylsulfonyl group and trifluoromethylsulfonyl group, and arylsulfonyl groups such as a phenylsulfonyl group and a 4-methylphenylsulfonyl group.

As an aspect of the compound of the present invention, the following thiazole compounds are exemplified.

A thiazole compound represented by Formula (1) in which $R^1$ is a C1-C3 alkyl group, and n is 0;

a thiazole compound represented by Formula (1) in which $R^1$ is a methyl group, and n is 0;

a thiazole compound represented by Formula (1) in which $R^1$ is an ethyl group, and n is 0;

a thiazole compound represented by Formula (1) in which $R^1$ is a C1-C3 alkyl group, and n is 1;

a thiazole compound represented by Formula (1) in which $R^1$ is a methyl group, and n is 1;

a thiazole compound represented by Formula (1) in which $R^1$ is a C1-C3 alkyl group, and n is 2;

a thiazole compound represented by Formula (1) in which $R^1$ is a methyl group, and n is 2;

a thiazole compound represented by Formula (1) in which each of $R^3$ and $R^4$ is a hydrogen atom;

a thiazole compound represented by Formula (1) in which each of $R^3$ and $R^4$ is a hydrogen atom, and Ar is a phenyl group optionally having one or more atoms or groups selected from the group A;

a thiazole compound represented by Formula (1) in which each of $R^3$ and $R^4$ is a hydrogen atom, and Ar is a naphthyl group optionally having one or more atoms or groups selected from the group A;

a thiazole compound represented by Formula (1) in which each of $R^3$ and $R^4$ is a hydrogen atom, and Ar is a pyridyl group optionally having one or more atoms or groups selected from the group A;

a thiazole compound represented by Formula (1) in which each of $R^3$ and $R^4$ is a hydrogen atom, and Ar is a thienyl group optionally having one or more atoms or groups selected from the group A;

a thiazole compound represented by Formula (1) in which each of $R^3$ and $R^4$ is a hydrogen atom, and Ar is a phenyl group optionally having one or more atoms or groups selected from the group C;

a thiazole compound represented by Formula (1) in which $R^3$ and $R^4$ are hydrogen atoms, and Ar is a naphthyl group optionally having one or more atoms or groups selected from the group C;

a thiazole compound represented by Formula (1) in which each of $R^3$ and $R^4$ is a hydrogen atom, and Ar is a pyridyl group optionally having one or more atoms or groups selected from the group C;

a thiazole compound represented by Formula (1) in which each of $R^3$ and $R^4$ is a hydrogen atom, and Ar is a thienyl group optionally having one or more atoms or groups selected from the group C;

a thiazole compound represented by Formula (1) in which $R^1$ is a C1-C3 alkyl group, $R^2$ is a hydrogen atom, and n is 0;

a thiazole compound represented by Formula (1) in which $R^1$ is a methyl group, $R^2$ is a hydrogen atom, and n is 0;

a thiazole compound represented by Formula (1) in which $R^1$ is an ethyl group, $R^2$ is a hydrogen atom, and n is 0;

a thiazole compound represented by Formula (1) in which $R^1$ is a C1-C3 alkyl group, $R^2$ is a hydrogen atom, and n is 1;

a thiazole compound represented by Formula (1) in which $R^1$ is a methyl group, $R^2$ is a hydrogen atom, and n is 1;

a thiazole compound represented by Formula (1) in which $R^1$ is a C1-C3 alkyl group, $R^2$ is a hydrogen atom, and n is 2;

a thiazole compound represented by Formula (1) in which $R^1$ is a methyl group, $R^2$ is a hydrogen atom, and n is a thiazole compound represented by Formula (1) in which $R^1$ is a C1-C3 alkyl group, $R^2$ is a methyl group, and n is 0;

a thiazole compound represented by Formula (1) in which $R^1$ is a methyl group, $R^2$ is a methyl group, and n is 0;

a thiazole compound represented by Formula (1) in which each of $R^2$, $R^3$, and $R^4$ is a hydrogen atom;

a thiazole compound represented by Formula (1) in which $R^2$ is a methyl group, and each of $R^3$ and $R^4$ is a hydrogen atom;

a thiazole compound represented by Formula (1) in which each of $R^2$, $R^3$, and $R^4$ is a hydrogen atom, and Ar is a phenyl group optionally having one or more atoms or groups selected from the group A;

a thiazole compound represented by Formula (1) in which each of $R^2$, $R^3$, and $R^4$ is a hydrogen atom, and Ar is a naphthyl group optionally having one or more atoms or groups selected from the group A;

a thiazole compound represented by Formula (1) in which each of $R^2$, $R^3$, and $R^4$ is a hydrogen atom, and Ar is a pyridyl group optionally having one or more atoms or groups selected from the group A;

a thiazole compound represented by Formula (1) in which each of $R^2$, $R^3$, and $R^4$ is a hydrogen atom, and Ar is a thienyl group optionally having one or more atoms or groups selected from the group A;

a thiazole compound represented by Formula (1) in which each of $R^2$, $R^3$, and $R^4$ is a hydrogen atom, and Ar is a phenyl group optionally having one or more atoms or groups selected from the group C;

a thiazole compound represented by Formula (1) in which each of $R^2$, $R^3$, and $R^4$ is a hydrogen atom, and Ar is a naphthyl group optionally having one or more atoms or groups selected from the group C;

a thiazole compound represented by Formula (1) in which each of $R^2$, $R^3$, and $R^4$ is a hydrogen atom, and Ar is a pyridyl group optionally having one or more atoms or groups selected from the group C;

a thiazole compound represented by Formula (1) in which each of $R^2$, $R^3$, and $R^4$ is a hydrogen atom, and Ar is a thienyl group optionally having one or more atoms or groups selected from the group C;

a thiazole compound represented by Formula (1) in which $R^2$ is a methyl group, each of $R^3$ and $R^1$ is a hydrogen atom, and Ar is a phenyl group optionally having one or more atoms or groups selected from the group A;

a thiazole compound represented by Formula (1) in which $R^2$ is a methyl group, each of $R^3$ and $R^4$ is a hydrogen atom, and Ar is a phenyl group optionally having one or more atoms or groups selected from the group C;

a thiazole compound represented by Formula (1) in which $R^1$ is a C1-C3 alkyl group, each of $R^3$ and $R^4$ is a hydrogen atom, and n is 0;

a thiazole compound represented by Formula (1) in which $R^1$ is a methyl group, each of $R^3$ and $R^4$ is a hydrogen atom, and n is 0;

a thiazole compound represented by Formula (1) in which $R^1$ is an ethyl group, each of $R^3$ and $R^4$ is a hydrogen atom, and n is 0;

a thiazole compound represented by Formula (1) in which $R^1$ is a C1-C3 alkyl group, each of $R^3$ and $R^4$ is a hydrogen atom, and n is 1;

a thiazole compound represented by Formula (1) in which $R^1$ is a methyl group, each of $R^1$ and $R^4$ is a hydrogen atom, and n is 1;

a thiazole compound represented by Formula (1) in which $R^1$ is a C1-C3 alkyl group, each of $R^3$ and $R^4$ is a hydrogen atom, and n is 2;

a thiazole compound represented by Formula (1) in which $R^1$ is a methyl group, each of $R^3$ and $R^4$ is a hydrogen atom, and n is 2;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group A, and n is 0;

a thiazole compound represented by Formula (1) in which $R^1$ is a methyl group, each of $R^3$ and $R^4$ is a hydrogen atom, Ar is a phenyl group optionally having one or more atoms or groups selected from the group A, and n is 0;

a thiazole compound represented by Formula (1) in which $R^1$ is an ethyl group, each of $R^3$ and $R^4$ is a hydrogen atom, Ar is a phenyl group optionally having one or more atoms or groups selected from the group A, and n is 0;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group A, and n is 1;

a thiazole compound represented by Formula (1) in which $R^1$ is a methyl group, each of $R^3$ and $R^4$ is a hydrogen atom, Ar is a phenyl group optionally having one or more atoms or groups selected from the group A, and n is 1;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group A, and n is 2;

a thiazole compound represented by Formula (1) in which $R^1$ is a methyl group, each of $R^3$ and $R^1$ is a hydrogen atom, Ar is a phenyl group optionally having one or more atoms or groups selected from the group A, and n is 2;

a thiazole compound represented by Formula (1) in which $R^1$ is a C1-C3 alkyl group, each of $R^3$ and $R^4$ is a hydrogen atom, Ar is a naphthyl group optionally having one or more atoms or groups selected from the group A, and n is 0;

a thiazole compound represented by Formula (1) in which $R^1$ is a methyl group, each of $R^3$ and $R^1$ is a hydrogen atom, Ar is a naphthyl group optionally having one or more atoms or groups selected from the group A, and n is 0;

a thiazole compound represented by Formula (1) in which $R^1$ is a C1-C3 alkyl group, each of $R^3$ and $R^4$ is a hydrogen atom, Ar is a pyridyl group optionally having one or more atoms or groups selected from the group A, and n is 0;

a thiazole compound represented by Formula (1) in which $R^1$ is a methyl group, each of $R^3$ and $R^1$ is a hydrogen atom, Ar is a pyridyl group optionally having one or more atoms or groups selected from the group A, and n is 0;

a thiazole compound represented by Formula (1) in which $R^1$ is a C1-C3 alkyl group, each of $R^3$ and $R^4$ is a hydrogen atom, Ar is a thienyl group optionally having one or more atoms or groups selected from the group A, and n is 0;

a thiazole compound represented by Formula (1) in which $R^1$ is a methyl group, each of $R^3$ and $R^4$ is a hydrogen atom, Ar is a thienyl group optionally having one or more atoms or groups selected from the group A, and n is 0;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group C, and n is 0;

a thiazole compound represented by Formula (1) in which $R^1$ is a methyl group, each of $R^3$ and $R^4$ is a hydrogen atom, Ar is a phenyl group optionally having one or more atoms or groups selected from the group C, and n is 0;

a thiazole compound represented by Formula (1) in which $R^1$ is an ethyl group, each of $R^3$ and $R^4$ is a hydrogen atom, Ar is a phenyl group optionally having one or more atoms or groups selected from the group C, and n is 0;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group C, and n is 1;

a thiazole compound represented by Formula (1) in which $R^1$ is a methyl group, each of $R^3$ and $R^1$ is a hydrogen atom, Ar is a phenyl group optionally having one or more atoms or groups selected from the group C, and n is 1;

a thiazole compound represented by Formula (1) in which $R^1$ is a C1-C3 alkyl group, each of $R^3$ and $R^4$ is a hydrogen atom, Ar is a phenyl group optionally having one or more atoms or groups selected from the group C, and n is 2;

a thiazole compound represented by Formula (1) in which $R^1$ is a methyl group, each of $R^3$ and $R^1$ is a hydrogen atom, Ar is a phenyl group optionally having one or more atoms or groups selected from the group C, and n is 2;

a thiazole compound represented by Formula (1) in which $R^1$ is a C1-C3 alkyl group, each of $R^3$ and $R^4$ is a hydrogen atom, Ar is a naphthyl group optionally having one or more atoms or groups selected from the group C, and n is 0;

a thiazole compound represented by Formula (1) in which $R^1$ is a methyl group, each of $R^3$ and $R^1$ is a hydrogen atom, Ar is a naphthyl group optionally having one or more atoms or groups selected from the group C, and n is 0;

a thiazole compound represented by Formula (1) in which $R^1$ is a C1-C3 alkyl group, each of $R^3$ and $R^4$ is a hydrogen atom, Ar is a pyridyl group optionally having one or more atoms or groups selected from the group C, and n is 0;

a thiazole compound represented by Formula (1) in which $R^1$ is a methyl group, each of $R^3$ and $R^4$ is a hydrogen atom, Ar is a pyridyl group optionally having one or more atoms or groups selected from the group C, and n is 0;

a thiazole compound represented by Formula (1) in which $R^1$ is a C1-C3 alkyl group, each of $R^3$ and $R^4$ is a hydrogen atom, Ar is a thienyl group optionally having one or more atoms or groups selected from the group C, and n is 0;

a thiazole compound represented by Formula (1) in which $R^1$ is a methyl group, each of $R^3$ and $R^4$ is a hydrogen atom, Ar is a thienyl group optionally having one or more atoms or groups selected from the group C, and n is 0;

a thiazole compound represented by Formula (1) in which $R^1$ is a C1-C3 alkyl group, each of $R^2$, $R^3$, and $R^4$ is a hydrogen atom, and n is 0;

a thiazole compound represented by Formula (1) in which $R^1$ is a methyl group, each of $R^2$, $R^3$, and $R^4$ is a hydrogen atom, and n is 0;

a thiazole compound represented by Formula (1) in which $R^1$ is an ethyl group, each of $R^2$, $R^3$, and $R^4$ is a hydrogen atom, and n is 0;

a thiazole compound represented by Formula (1) in which $R^1$ is a C1-C3 alkyl group, each of $R^2$, $R^3$, and $R^4$ is a hydrogen atom, and n is 1;

a thiazole compound represented by Formula (1) in which $R^1$ is a methyl group, each of $R^2$, $R^3$, and $R^4$ is a hydrogen atom, and n is 1;

a thiazole compound represented by Formula (1) in which $R^1$ is a C1-C3 alkyl group, each of $R^2$, $R^3$, and $R^4$ is a hydrogen atom, and n is 2;

a thiazole compound represented by Formula (1) in which $R^1$ is a methyl group, each of $R^2$, $R^3$, and $R^4$ is a hydrogen atom, and n is 2;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group A, and n is 0;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group A, and n is 0;

a thiazole compound represented by Formula (1) in which $R^1$ is an ethyl group, each of $R^2$, $R^3$, and $R^4$ is a hydrogen atom, Ar is a phenyl group optionally having one or more atoms or groups selected from the group A, and n is 0;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group A, and n is 1;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group A, and n is 1;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group A, and n is 2;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group A, and n is 2;

a thiazole compound represented by Formula (1) in which $R^1$ is a C1-C3 alkyl group, each of $R^2$, $R^3$, and $R^4$ is a hydrogen atom, Ar is a naphthyl group optionally having one or more atoms or groups selected from the group A, and n is 0;

a thiazole compound represented by Formula (1) in which $R^1$ is a methyl group, each of $R^2$, $R^3$, and $R^4$ is a hydrogen atom, Ar is a naphthyl group optionally having one or more atoms or groups selected from the group A, and n is 0;

a thiazole compound represented by Formula (1) in which $R^1$ is a C1-C3 alkyl group, each of $R^2$, $R^3$, and $R^4$ is a hydrogen atom, Ar is a pyridyl group optionally having one or more atoms or groups selected from the group A, and n is 0;

a thiazole compound represented by Formula (1) in which $R^1$ is a methyl group, each of $R^2$, $R^3$, and $R^4$ is a hydrogen atom, Ar is a pyridyl group optionally having one or more atoms or groups selected from the group A, and n is 0;

a thiazole compound represented by Formula (1) in which $R^1$ is a C1-C3 alkyl group, each of $R^2$, $R^3$, and $R^4$ is a hydrogen atom, Ar is a thienyl group optionally having one or more atoms or groups selected from the group A, and n is 0;

a thiazole compound represented by Formula (1) in which $R^1$ is a methyl group, each of $R^2$, $R^3$, and $R^4$ is a hydrogen atom, Ar is a thienyl group optionally having one or more atoms or groups selected from the group A, and n is 0;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group C, and n is 0;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group C, and n is 0;

a thiazole compound represented by Formula (1) in which $R^1$ is an ethyl group, each of $R^2$, $R^3$, and $R^4$ is a hydrogen atom, Ar is a phenyl group optionally having one or more atoms or groups selected from the group C, and n is 0;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group C, and n is 1;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group C, and n is 1;

a thiazole compound represented by Formula (1) in which $R^1$ is a C1-C3 alkyl group, each of $R^2$, $R^3$, and $R^4$ is a hydrogen atom, Ar is a phenyl group optionally having one or more atoms or groups selected from the group C, and n is 2;

a thiazole compound represented by Formula (1) in which $R^1$ is a methyl group, each of $R^2$, $R^3$, and $R^4$ is a hydrogen atom, Ar is a phenyl group optionally having one or more atoms or groups selected from the group C, and n is 2;

a thiazole compound represented by Formula (1) in which $R^1$ is a C1-C3 alkyl group, each of $R^2$, R, and $R^4$ is a hydrogen atom, Ar is a naphthyl group optionally having one or more atoms or groups selected from the group C, and n is 0;

a thiazole compound represented by Formula (1) in which $R^1$ is a methyl group, each of $R^2$, $R^3$, and $R^4$ is a hydrogen atom, Ar is a naphthyl group optionally having one or more atoms or groups selected from the group C, and n is 0;

a thiazole compound represented by Formula (1) in which $R^1$ is a C1-C3 alkyl group, each of $R^2$, $R^3$, and $R^1$ is a hydrogen atom, Ar is a pyridyl group optionally having one or more atoms or groups selected from the group C, and n is 0;

a thiazole compound represented by Formula (1) in which $R^1$ is a methyl group, each of $R^2$, $R^3$, and $R^4$ is a hydrogen atom, Ar is a pyridyl group optionally having one or more atoms or groups selected from the group C, and n is 0;

a thiazole compound represented by Formula (1) in which $R^1$ is a C1-C3 alkyl group, each of $R^2$, $R^3$, and $R^4$ is a hydrogen atom, Ar is a thienyl group optionally having one or more atoms or groups selected from the group C, and n is 0;

a thiazole compound represented by Formula (1) in which $R^1$ is a methyl group, each of $R^2$, $R^3$, and $R^4$ is a hydrogen atom, Ar is a thienyl group optionally having one or more atoms or groups selected from the group C, and n is 0;

a thiazole compound represented by Formula (1) in which $R^1$ is a C1-C3 alkyl group, $R^2$ is a methyl group, each of $R^3$ and $R^4$ is a hydrogen atom, and n is 0;

a thiazole compound represented by Formula (1) in which $R^1$ is a methyl group, $R^2$ is a methyl group, each of $R^3$ and $R^4$ is a hydrogen atom, and n is 0;

a thiazole compound represented by Formula (1) in which $R^1$ is a C1-C3 alkyl group, $R^2$ is a methyl group, each of $R^3$ and $R^4$ is a hydrogen atom, Ar is a phenyl group optionally having one or more atoms or groups selected from the group A, and n is 0;

a thiazole compound represented by Formula (1) in which $R^1$ is a methyl group, $R^2$ is a methyl group, each of $R^3$ and $R^4$ is a hydrogen atom, Ar is a phenyl group optionally having one or more atoms or groups selected from the group A, and n is 0;

a thiazole compound represented by Formula (1) in which $R^1$ is a C1-C3 alkyl group, $R^2$ is a methyl group, each of $R^3$ and $R^4$ is a hydrogen atom, Ar is a phenyl group optionally having one or more atoms or groups selected from the group C, and n is 0;

a thiazole compound represented by Formula (1) in which $R^1$ is a methyl group, $R^2$ is a methyl group, each of $R^3$ and $R^4$ is a hydrogen atom, Ar is a phenyl group optionally having one or more atoms or groups selected from the group C, and n is 0;

a thiazole compound represented by Formula (1) in which Ar is a phenyl group optionally having one or more atoms or groups selected from the group D, a naphthyl group optionally having one or more atoms or groups selected from the group D, or a 5- or 6-membered heteroaryl group optionally having one or more atoms or groups selected from the group D, and the group D is the group consisting of a C1-C4 alkyl group optionally having one or more fluorine atoms, a C2-C4 alkenyl group, a C1-C4 alkoxy group optionally having one or more fluorine atoms, a C1-C4 alkylthio group optionally having one or more fluorine atoms, a phenyl group optionally having one or more atoms or groups selected from the group B, a phenoxy group optionally having one or more atoms or groups selected from the group B, a (C1-C3 alkoxy) C1-C3 alkyl group, a cyano group, a di(C1-C3 alkyl) amino group, and a halogen atom;

a thiazole compound represented by Formula (1) in which Ar is a phenyl group optionally having one or more atoms or groups selected from the group E, a naphthyl group optionally having one or more atoms or groups selected from the group E, or a 5- or 6-membered heteroaryl group optionally having one or more atoms or groups selected from the group E, and the group E is the group consisting of a C1-C4 alkyl group optionally having one or more fluorine atoms, an ethynyl group, a C1-C4 alkoxy group optionally having one or more fluorine atoms, a methylthio group, a phenoxy group, a methoxymethyl group, a cyano group, a dimethylamino group, and a halogen atom;

a thiazole compound represented by Formula (1) in which Ar is a phenyl group optionally having one or more atoms or groups selected from the group E, a naphthyl group, or a 5- or 6-membered heteroaryl group optionally having one or more groups selected from the group F, and the group F is the group consisting of a C1-C3 alkyl group and a C1-C3 alkoxy group;

a thiazole compound represented by Formula (1) in which Ar is a phenyl group optionally having one or more atoms or groups selected from the group E, a naphthyl group, or a 5- or 6-membered heteroaryl group optionally having one or more groups selected from the group F, and the 5- or 6-membered heteroaryl group is a pyridyl group, a thienyl group, or a furyl group;

a thiazole compound represented by Formula (1) in which $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, and Ar is a phenyl group optionally having one or more atoms or groups selected from the group D, a naphthyl group optionally having one or more atoms or groups selected from the group D, or a 5- or 6-membered heteroaryl group optionally having one or more atoms or groups selected from the group D;

a thiazole compound represented by Formula (1) in which $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, and Ar is a phenyl group optionally having one or more atoms or groups selected from the group E, a naphthyl group optionally having one or more atoms or groups selected from the group E, or a 5- or 6-membered heteroaryl group optionally having one or more atoms or groups selected from the group E;

a thiazole compound represented by Formula (1) in which $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, and Ar is a phenyl group optionally having one or more atoms or groups selected from the group E, a naphthyl group, or a 5- or 6-membered heteroaryl group optionally having one or more groups selected from the group F;

a thiazole compound represented by Formula (1) in which $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, Ar is a phenyl group optionally having one or more atoms or groups selected from the group E, a naphthyl group, or a 5- or 6-membered heteroaryl group optionally having one or more groups selected from the group F, and the 5- or 6-membered heteroaryl group is a pyridyl group, a thienyl group, or a furyl group;

a thiazole compound represented by Formula (1) in which $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, Ar is a phenyl group optionally having one or more atoms or groups selected from the group E, a naphthyl group, or a 5- or 6-membered heteroaryl group optionally having one or more groups selected from the group F, the 5- or 6-membered heteroaryl group is a pyridyl group, a thienyl group, or a furyl group, and n is 0; and a thiazole compound represented by Formula (1) in which, in a case where n is 0, $R^1$ is a C1-C3 alkyl group, $R^2$ is hydrogen atom or a methyl group, $R^3$ is a hydrogen atom, $R^4$ is a C1-C3 alkyl group, a cyclopropyl group, or a hydrogen atom, Ar is a phenyl group optionally having one or more atoms or groups selected from the group E, a naphthyl group, or a 5- or 6-membered heteroaryl group optionally having one or more groups selected from the group F, and the 5- or 6-membered heteroaryl group is a pyridyl group, a thienyl group, or a furyl group, and in a case where n is 1 or 2, $R^1$ is a methyl group, $R^1$ is a hydrogen atom, $R^3$ and $R^4$ are hydrogen atoms, and Ar is a phenyl group optionally having a methyl group.

Next, production methods of the compound of the present invention will be described.

The compound of the present invention may be produced according to, for example, the following (Production Method 1) to (Production Method 6).

Hereinafter, the compound represented by Formula (α) is referred to as a "compound (α)" in some cases.

(Production Method 1)

The compound of the present invention may be produced by reacting a compound (2) with a compound (3).

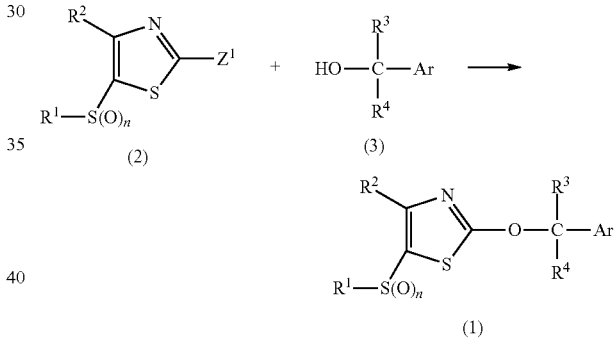

[wherein $R^1$, $R^2$, $R^3$, $R^4$, Ar, and n each have the same meaning as described above, and $Z^1$ represents a leaving group.]

The reaction is usually performed in a solvent.

Examples of the solvent used in the reaction include water; ketones such as acetone and methyl ethyl ketone; ethers such as tetrahydrofuran (hereinafter, sometimes referred to as THF), diethyl ether, t-butyl methyl ether, ethylene glycol dimethyl ether, and 1,4-dioxane; acid amides such as N,N-dimethylformamide (hereinafter, sometimes referred to as DMF); nitriles such as acetonitrile; aromatic hydrocarbons such as toluene and xylene; aliphatic hydrocarbons such as pentane, hexane, and heptane; esters such as ethyl acetate; sulfoxides such as dimethyl sulfoxide; sulfones such as sulfolane; halogenated hydrocarbons such as 1,2-dichloroethane, chloroform, and chlorobenzene; organic amines such as pyridine, lutidine, and collidine; and mixtures thereof.

The amount of the compound (3) used in the reaction is usually 0.5 moles to 5 moles with respect to 1 mole of the compound (2).

The reaction is usually performed in the presence of a base.

Examples of the base used in the reaction include alkali metal hydrides such as sodium hydride; carbonates such as sodium carbonate, potassium carbonate, and cesium carbonate; alkali metal hydroxides such as sodium hydroxide and potassium hydroxide; alkali metal alkoxides such as potassium t-butoxide; and organic amines such as triethylamine, pyridine, and 1,8-diazabicyclo[5.4.0]undec-7-ene. The amount of the base used in the reaction is usually 1 mole to 5 moles with respect to 1 mole of the compound (2). In addition, in a case where an organic base such as pyridine is used, the reaction may also be performed in an organic base of a solvent amount.

The reaction may also be performed out in the presence of a phase transfer catalyst. Examples of the phase transfer catalyst used in the reaction include quaternary ammonium salt such as tetrabutylammonium bromide and benzyltriethylammonium chloride. The amount of the phase transfer catalyst used in the reaction is usually 0.01 moles to 0.5 moles with respect to 1 mole of the compound (2).

The reaction temperature of the reaction is usually within a range of 0° C. to 200° C. The reaction time of the reaction is usually within a range of 0.1 hours to 24 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Production Method 2)

Among the compounds of the present invention, a compound (1a) in a case where n is 0 may be produced by reacting a compound (4) with a compound (5).

The reaction is usually performed in the presence of a base.

Examples of the base used in the reaction include alkali metal hydrides such as sodium hydride; carbonates such as sodium carbonate, potassium carbonate, and cesium carbonate; alkali metal hydroxides such as sodium hydroxide and potassium hydroxide; alkali metal alkoxides such as potassium t-butoxide; and organic amines such as triethylamine, pyridine, and 1,8-diazabicyclo[5.4.0]undec-7-ene. The amount of the base used in the reaction is usually 1 mole to 5 moles with respect to 1 mole of the compound (4). In addition, in a case where an organic base such as pyridine is used, the reaction may also be performed in an organic base of a solvent amount.

The reaction may also be performed out in the presence of a phase transfer catalyst. Examples of the phase transfer catalyst used in the reaction include quaternary ammonium salt such as tetrabutylammonium bromide and benzyltriethylammonium chloride. The amount of the phase transfer catalyst used in the reaction is usually 0.01 moles to 0.5 moles with respect to 1 mole of the compound (4).

The reaction temperature of the reaction is usually within a range of 0° C. to 200° C. The reaction time of the reaction is usually within a range of 0.1 hours to 24 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Production Method 3)

The compound of the present invention may be produced by reacting a compound (6) with a compound (7).

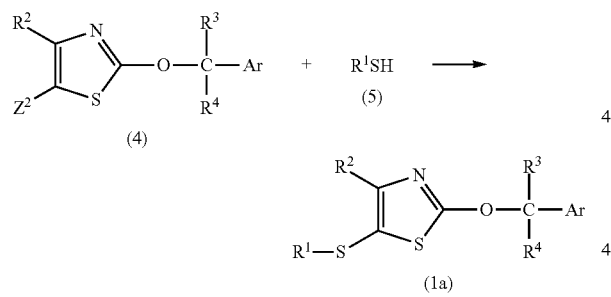

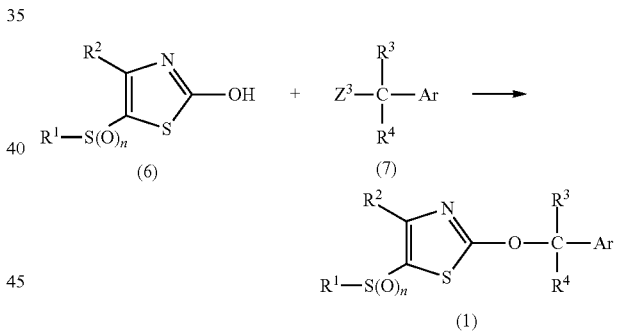

[wherein $R^1$, $R^2$, $R^3$, $R^4$, and Ar each have the same meaning as described above, and $Z^2$ represents a chlorine atom, a bromine atom, or an iodine atom.]

The reaction is usually performed in a solvent.

Examples of the solvent used in the reaction include water; ketones such as acetone and methyl ethyl ketone; ethers such as tetrahydrofuran, diethyl ether, t-butyl methyl ether, ethylene glycol dimethyl ether, and 1,4-dioxane; acid amides such as N,N-dimethylformamide; nitriles such as acetonitrile; aromatic hydrocarbons such as toluene and xylene; aliphatic hydrocarbons such as pentane, hexane, and heptane; esters such as ethyl acetate; sulfoxides such as dimethyl sulfoxide; sulfones such as sulfolane; halogenated hydrocarbons such as 1,2-dichloroethane, chloroform, and chlorobenzene; organic amines such as pyridine, lutidine, and collidine; and mixtures thereof.

The amount of the compound (5) used in the reaction is usually 0.5 moles to 5 moles with respect to 1 mole of the compound (4).

[wherein $R^1$, $R^2$, $R^3$, $R^4$, Ar, and n each have the same meaning as described above, and $Z^3$ is a leaving group.]

The reaction is usually performed in a solvent.

Examples of the solvent used in the reaction include water; alcohols such as methanol, ethanol, and isopropyl alcohol; ketones such as acetone and methyl ethyl ketone; ethers such as tetrahydrofuran, diethyl ether, t-butyl methyl ether, ethylene glycol dimethyl ether, and 1,4-dioxane; acid amides such as N,N-dimethylformamide; nitriles such as acetonitrile; aromatic hydrocarbons such as toluene and xylene; aliphatic hydrocarbons such as pentane, hexane, and heptane; esters such as ethyl acetate; sulfoxides such as dimethyl sulfoxide; sulfones such as sulfolane; halogenated hydrocarbons such as 1,2-dichloroethane, chloroform, and chlorobenzene; organic amines such as pyridine, lutidine, and collidine; and mixtures thereof.

The amount of the compound (6) used in the reaction is usually 0.5 moles to 5 moles with respect to 1 mole of the compound (7).

The reaction is usually performed in the presence of a base.

Examples of the base used in the reaction include alkali metal hydrides such as sodium hydride; carbonates such as sodium carbonate, potassium carbonate, and cesium carbonate; alkali metal hydroxides such as sodium hydroxide and potassium hydroxide; alkali metal alkoxides such as potassium t-butoxide; and organic amines such as triethylamine, pyridine, and 1,8-diazabicyclo[5.4.0]undec-7-ene.

The amount of the base used in the reaction is usually 1 mole to 5 moles with respect to 1 mole of the compound (6). In addition, in a case where an organic base such as pyridine is used, the reaction may also be performed in an organic base of a solvent amount.

The reaction may also be performed out in the presence of a phase transfer catalyst. Examples of the phase transfer catalyst used in the reaction include quaternary ammonium salt such as tetrabutylammonium bromide and benzyltriethylammonium chloride. The amount of the phase transfer catalyst used in the reaction is usually 0.01 moles to 0.5 moles with respect to 1 mole of the compound (6).

The reaction temperature of the reaction is usually within a range of 0° C. to 160° C. The reaction time of the reaction is usually within a range of 0.1 hours to 24 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Production Method 4)

Among the compounds of the present invention, the compound (1a) in a case where n is 0 may be produced by reacting the compound (4) with an organometallic reagent and reacting the resulting product with a compound (8).

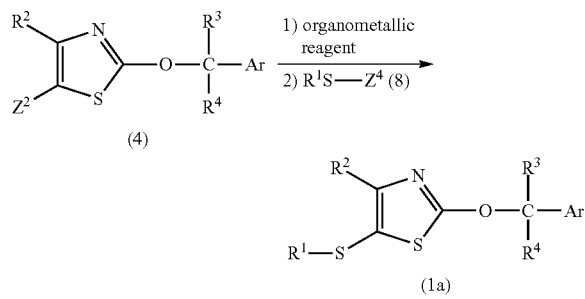

[wherein $R^1$, $R^2$, $R^3$, $R^4$, Ar, and $Z^2$ each have the same meaning as described above, and $Z^4$ represents a chlorine atom, a bromine atom, or a C1-C4 alkylthio group optionally having one or more fluorine atoms.]

The reaction is usually performed in a solvent.

Examples of the solvent used in the reaction include ethers such as tetrahydrofuran, diethyl ether, t-butyl methyl ether, ethylene glycol dimethyl ether, and 1,4-dioxane; aromatic hydrocarbons such as toluene and xylene; aliphatic hydrocarbons such as pentane, hexane, and heptane; and mixtures thereof.

Examples of the organometallic reagent used in the reaction include organolithium compounds such as methyllithium, n-butyllithium, s-butyllithium, t-butyllithium, and phenyllithium; and organomagnesium compounds such as methylmagnesium bromide, isopropylmagnesium bromide, t-butylmagnesium bromide, and phenylmagnesium bromide. The amount of the organometallic reagent used in the reaction is usually 1 mole to 2 moles with respect to 1 mole of the compound (4).

The amount of the compound (8) used in the reaction is usually 1 moles to 5 moles with respect to 1 mole of the compound (4).

The reaction temperature of the reaction is usually within a range of −100° C. to 50° C. The reaction time of the reaction is usually within a range of 15 minutes to 6 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Production Method 5)

Among the compounds of the present invention, the compound (1a) in a case where n is 0 may be produced by reacting the compound (9) with a base and reacting the resulting product with a compound (8).

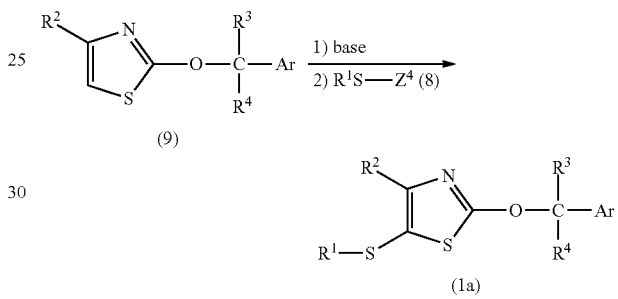

[wherein $R^1$, $R^2$, $R^3$, $R^4$, Ar, and $Z^4$ each have the same meaning as described above.]

The reaction is usually performed in a solvent.

Examples of the solvent used in the reaction include ethers such as tetrahydrofuran, diethyl ether, t-butyl methyl ether, ethylene glycol dimethyl ether, and 1,4-dioxane; aromatic hydrocarbons such as toluene and xylene; aliphatic hydrocarbons such as pentane, hexane, and heptane; and mixtures thereof.

Examples of the base used in the reaction include organolithium compounds such as n-butyllithium and phenyllithium; and lithium hexamethyldisilazide, sodium hexamethyldisilazide, potassium hexamethyldisilazide, and lithium diisopropylamide (hereinafter, referred to as LDA in some cases). The amount of the base used in the reaction is usually 1 mole to 2 moles with respect to 1 mole of the compound (9).

The amount of the compound (8) used in the reaction is usually 1 moles to 5 moles with respect to 1 mole of the compound (9).

The reaction temperature of the reaction is usually within a range of −100° C. to 50° C. The reaction time of the reaction is usually within a range of 15 minutes to 6 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Production Method 6)

Among the compounds of the present invention, a compound (1b) in a case where n is 1 and a compound (1c) in a case where n is 2 may be produced by oxidizing the compound (1a) in a case where n is 0.

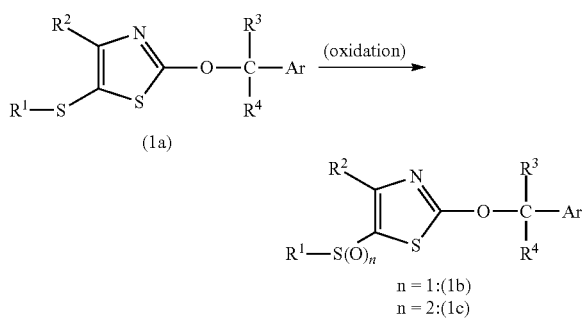

[wherein $R^1$, $R^2$, $R^3$, $R^4$, and Ar each have the same meaning as described above.]

Examples of the oxidant used in the reaction include hydrogen peroxide; peracids such as peracetic acid, perbenzoic acid, and 3-chloroperbenzoic acid; and potassium permanganate, sodium periodate, and sodium percarbonate.

A method of using 3-chloroperbenzoic acid as an oxidant will be more specifically described below.

Examples of the solvent used in this reaction include alcohols such as methanol, ethanol, and isopropyl alcohol; acid amides such as N,N-dimethylformamide; nitriles such as acetonitrile; halogenated hydrocarbons such as 1,2-dichloroethane, chloroform, and chlorobenzene; and mixtures thereof.

The amount of 3-chloroperbenzoic acid used in the reaction is usually 1 mole to 10 moles with respect to 1 mole of the compound (1a).

The reaction temperature of the reaction is usually within a range of 0° C. to 150° C. The reaction time of the reaction is usually within a range of 0.1 hours to 24 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

Next, production methods of the intermediates used in production of the compounds of the present invention will be described.

(Reference Production Method 1)

The compound (4) may be produced by reacting a compound (10) with the compound (3).

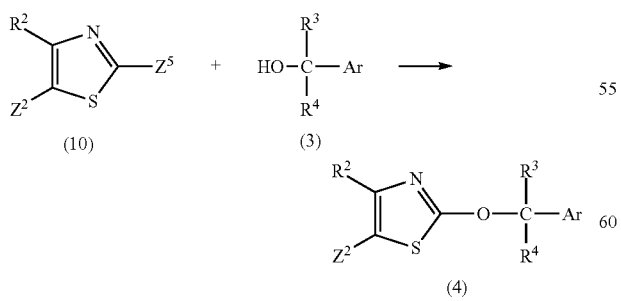

[wherein $R^2$, $R^3$, $R^4$, Ar, and Z each have the same meaning as described above, and $Z^5$ represents a leaving group.]

The reaction is usually performed in a solvent.

Examples of the solvent used in the reaction include water; ketones such as acetone and methyl ethyl ketone; ethers such as tetrahydrofuran, diethyl ether, t-butyl methyl ether, ethylene glycol dimethyl ether, and 1,4-dioxane; acid amides such as N,N-dimethylformamide; nitriles such as acetonitrile; aromatic hydrocarbons such as toluene and xylene; aliphatic hydrocarbons such as pentane, hexane, and heptane; esters such as ethyl acetate; sulfoxides such as dimethyl sulfoxide; sulfones such as sulfolane; halogenated hydrocarbons such as 1,2-dichloroethane, chloroform, and chlorobenzene; organic amines such as pyridine, lutidine, and collidine; and mixtures thereof.

The amount of the compound (3) used in the reaction is usually 0.5 moles to 5 moles with respect to 1 mole of the compound (10).

The reaction is usually performed in the presence of a base.

Examples of the base used in the reaction include alkali metal hydrides such as sodium hydride; carbonates such as sodium carbonate, potassium carbonate, and cesium carbonate; alkali metal hydroxides such as sodium hydroxide and potassium hydroxide; alkali metal alkoxides such as potassium t-butoxide; and organic amines such as triethylamine, pyridine, and 1,8-diazabicyclo[5.4.0]undec-7-ene. The amount of the base used in the reaction is usually 1 mole to 5 moles with respect to 1 mole of the compound (3). In addition, in a case where an organic base such as pyridine is used, the reaction may also be performed in an organic base of a solvent amount.

The reaction may also be performed out in the presence of a phase transfer catalyst. Examples of the phase transfer catalyst used in the reaction include quaternary ammonium salt such as tetrabutylammonium bromide and benzyltriethylammonium chloride. The amount of the phase transfer catalyst used in the reaction is usually 0.01 moles to 0.5 moles with respect to 1 mole of the compound (3).

The reaction temperature of the reaction is usually within a range of 0° C. to 200° C. The reaction time of the reaction is usually within a range of 0.1 hours to 24 hours.

After completion of the reaction, it is possible to isolate the compound of the present invention by performing post-treatment operations such as organic solvent extraction, drying, and concentration of the reaction mixture. The isolated compound of the present invention may also be purified by chromatography or recrystallization.

(Reference Production Method 2)

The compound (9) may be produced by reacting a compound (11) with the compound (3).

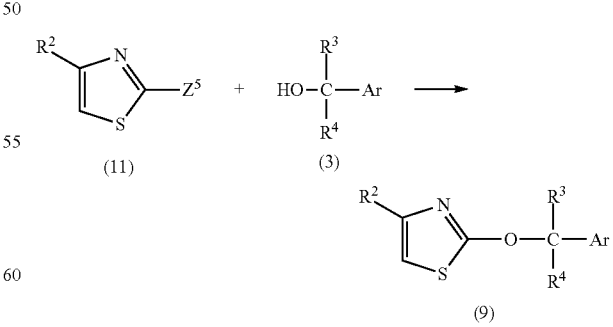

[wherein $R^2$, $R^3$, $R^4$, Ar, and $Z^5$ each have the same meaning as described above.]

The reaction is performed according to (Production Method 1).

(Reference Production Method 3)

Among the compounds (6), a compound (6b) in a case where n is 1 and a compound (6c) in a case where n is 2 may be produced by oxidizing a compound (6a) in a case where n is 0.

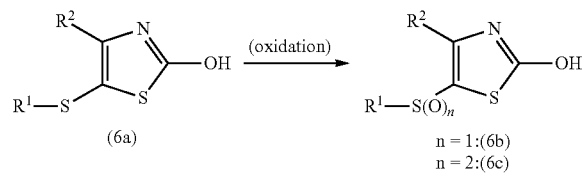

[wherein $R^1$ and $R^2$ each have the same meaning as described above.]

The reaction is performed according to (Production Method 6).

In the production methods and the reference production methods described above, the compound (2), the compound (3), the compound (5), the compound (6a), the compound (7), the compound (8), the compound (10), and the compound (11) are known, or may be produced according to known methods from known compounds.

Examples of pests for which the compound of the present invention has an effect include harmful arthropods such as harmful insects or harmful mites and nematodes. Specific examples of the pests include the following.

Hemiptera pests: planthoppers such as small brown planthoppers (*Laodelphax striatella*), brown planthoppers (*Nilaparvata lugens*), and white-backed planthoppers (*Sogatella furcifera*); leafhoppers such as green rice leafhoppers (*Nephotettix cincticeps*), Taiwan green rice leafhoppers (*Nephotettix virescens*), and tea green leafhoppers (*Empoasca onukii*); aphids such as cotton aphids (*Aphis gossypii*), green peach aphids (*Myzus persicae*), cabbage aphids (*Brevicoryne brassicae*), spiraea aphids (*Aphis spiraecola*), potato aphids (*Macrosiphum euphorbiae*), greenhouse potato aphids (*Aulacorthum solani*), bird-cherry oat aphids (*Rhopalosiphum* aphids *padi*), black citrus aphids (*Toxoptera citricidus*), and mealy plum aphids (*Hyalopterus pruni*); stink bugs such as eastern green stink bugs (*Nezara antennata*), bean bugs (*Riptortus clavetus*), male rice bugs (*Leptocorisa chinensis*), white-spotted spined bugs (*Eysarcoris parvus*), and brown marmorated stink bugs (*Halyomorpha mista*); whiteflies such as greenhouse whiteflies (*Trialeurodes vaporariorum*), silverleaf whiteflies (*Bemisia tabaci*), citrus whiteflies (*Dialeurodes citri*), and orange spiny whiteflies (*Aleurocanthus spiniferus*); scale insects such as red scales (*Aonidiella aurantii*), San Jose scales (*Comstockaspis perniciosa*), citrus snow scales (*Unaspis citri*), red wax scales (*Ceroplastes rubens*), cottony cushion scales (*Icerya purchasi*), mealybugs (*Planococcus kraunhiae*), comstock mealybugs (*Pseudococcus longispinis*), and white peach scales (*Pseudaulacaspis pentagona*); lace bugs; bedbugs such as *Cimex lectularius*; and psyllids.

Lepidoptera pests: pyralids such as asiatic rice borers (*Chilo suppressalis*), yellow stem borers (*Tryporyza incertulas*), rice leafrollers (*Cnaphalocrocis medinalis*), cotton leaf rollers (*Notarcha derogata*), Indian meal moths (*Plodia interpunctella*), Asian corn borers (*Ostrinia furnacalis*), cabbage webworms (*Hellula undalis*), and bluegrass webworms (*Pediasia teterrellus*); noctuids such as oriental leafworm moths (*Spodoptera litura*), beet armyworms (*Spodoptera exigua*), oriental armyworms (*Pseudaletia separata*), cabbage moths (*Mamestra brassicae*), black cutworms (*Agrotis ipsilon*), asiatic common loopers (*Plusia nigrisigna*), the genus *Trichoplusia*, the genus *Heliothis*, and the genus *Helicoverpa*; pieridae such as small white butterflies (*Pieris rapae*); leaf roller moths such as the genus *Adoxophyes*, oriental fruit moths (*Grapholita molesta*), soybean pod borers (*Leguminivora glycinivorella*), adzuki bean podworms (*Matsumuraeses azukivora*), summer fruit *tortrix* moths (*Adoxophyes orana fasciata*), smaller tea tortrixes (*Adoxophyes honmai.*), oriental tea *tortrix* moths (*Homona magnanima*), apple tortrixes (*Archips fuscocupreanus*), and codling moths (*Cydia pomonella*); meaf miners such as tea leaf rollers (*Caloptilia theivora*), and apple leaf miner (*Phyllonorycter ringoneella*); codling moths such as peach fruit moths (*Carposina niponensis*); leafminer moths such as the genus *Rionetia*; tussock moths such as the genus *Lymantria* and the genus *Euproctis*; ermine moths such as diamondback moths (*Plutella xylostella*); pink bollworms (*Pectinophora gossypiella*) and potato tuber moths (*Phthorimaea operculella*); tiger moths such as fall webworms (*Hyphantria cunea*); and tineids such as clothes moths (*Tinea translucens*) and common clothes moths (*Tineola bisselliella*).

Thysanoptera pests: trips such as western flower *thrips* (*Frankliniella occidentalis*), southern yellow *thrips* (*Thrips parmi*), yellow tea *thrips* (*Scirtothrips dorsalis*), onion *thrips* (*Thrips tabaci*), and flower *thrips* (*Frankliniella intonsa*).

Diptera pests: house mosquitoes such as common house mosquitoes (*Culex pipiens pallens*), *culex* mosquitoes (*Culex tritaeniorhynchus*), and southern house mosquitoes (*Culex quinquefasciatus*); aedes such as tallow fever mosquitoes (*Aedes aegypti*) and tiger mosquitoes (*Aedes albopictus*); anopheles such as hyrcanus group mosquitoes (*Anopheles sinensis*) and gambiae sensu strictoes (*Anopheles Gambiae*); midges; house flies such as common houseflies (*Musca domestica*) and false stable flies (*Muscina stabulans*); greenbottle flies; fleshflies; *Fannia canicularis*; root-maggots such as bean seed flies (*Delia platura*) and onion flies (*Delia antiqua*); leafminer flies such as Japanese rice leafminers (*Agromyza oryzae*), rice leafminers (*Hydrellia griseola*), vegetable leafminers, (*Liriomyza sativae*), American serpentine leafminers (*Liriomyza trifolii*), and garden pea leafminers (*Chromatomyia horticola*); fruit flies, such as rice stem maggots (Chlorops *oryzae*); fruit flies such as melon flies (*Dacus cucurbitae*) and Mediterranean fruit flies (*Ceratitis capitata*); dorsophilas; phorid flies such as flea flies (*Megaselia spiracularis*); sand flies such as moth flies (*Clogmia albipunctata*); fungus gnats; buffalo gnats; horse flies such as gadflies (*Tabanus trigonus*); louse flies; and stable flies.

Elytron pests: corn rootworms such as western corn rootworms (*Diabrotica virgifera virgifera*) and southern corn rootworms (*Diabrotica undecimpunctata howardi*); scarabaeid beetles such as scarab beetles (*Anomala cuprea*), soybean beetles (*Anomala rufocuprea*), and Japanese beetles (*Popillia japonica*); weevils such as maize weevils (*Sitophilus zeamais*), rice water weevils (*Lissorhoptrus oryzophilus*), adzuki bean weevils (*Callosobruchuys chienensis*), rice plant weevils (*Echinocnemus squameus*), boll weevils (*Anthonomus grandis*), and hunting billbugs (*Sphenophorus venatus*); mealworms such as tallow mealworms (*Tenebrio molitor*) and red flour beetles (*Tribolium castaneum*); leaf beetles such as rice leaf beetles (*Oulema oryzae*), cucurbit leaf beetles (*Aulacophora femoralis*), striped flea beetles (*Phyllotreta striolata*), and Colorado potato beetles (*Leptinotarsa decemlineata*); carpet beetles such as varied carpet beetles (*Anthrenus verbasci*), and hide beetles (*Dermestes maculates*); deathwatch beetles, such as cigarette beetles (*Lasioderma serricorne*); ladybugs such as 28-spotted ladybirds (*Epilachna vigintioctopunctata*); bark beetles such as powderpost beetles (*Lyctus brunneus*) and common pine shoot beetles (*Tomicus piniperda*); auger beetles; museum beetles; sawyer beetles such as sitrus long-horned beetles (*Anoplophora malasiaca*); and click beetles (*Agriotes* spp.), and rove beetles (*Paederus fuscipes*).

Orthopteran pests: migratory locusts (*Locusta migratoria*), mole crickets (*Gryllotalpa africana*), rice grasshoppers (*Oxya yezoensis*), rice grasshoppers (*Oxya japonica*), and crickets.

Siphonaptera pests: cat fleas (*Ctenocephalides felis*), dog fleas (*Ctenocephalides canis*), human fleas (*Pulex irritans*), oriental rat fleas (*Xenopsylla cheopis*), and the like.

Anoplura pests: body lice (*Pediculus humanus corporis*), head lice (*Pediculus humanus humanus*), pubic lice (*Phthirus pubis*), short-nosed cattle lice (*Haematopinus eurysternus*), sheep sucking lice (*Dalmalinia ovis*), pig lice (*Haematopinus suis*), dog sucking lice (*Linognathus setosus*), and the like.

Mallophaga pests: sheep biting lice (*Dalmalinia ovis*), cattle biting lice (*Dalmalinia bovis*), chicken shaft lice (*Menopon gallinae*), canine chewing lice (*Trichodectes canis*), cat chewing lice (*Felicola subrostrata*), and the like.

Hymenoptera pests: ants, such as pharaoh ants (*Monomorium pharaosis*), Japanese wood ants (Formica *fusca japonica*), black house ants (*Ochetellus glaber*), queenless ants (*Pristomyrmex pungens*), big-headed ants (*Pheidole noda*), leafcutter ants (*Acromyrmex* spp.), fire ants (*Solenopsis* spp.), and argentine ants (*Linepithema humile*); wasps; bethylid wasps; and sawflies such as turnip sawflies (*Athalia rosae*) and cabbage sawflies (*Athalia japonica*).

Nematodes: rice white tip nematodes (*Aphelenchoides besseyi*), strawberry bud nematodes (*Nothotylenchus acris*), southern root-knot nematodes (*Meloidogyne incognita*), northern root-knot nematodes (*Meloidogyne hapla*), Javanese root-knot nematodes (*Meloidogyne javanica*), soybean cyst nematodes (*Heterodera glycines*), potato cyst nematodes (*Globodera rostochiensis*), South meadow nematodes (*Pratylenchus coffeae*), and wheat meadow nematodes (*Pratylenchus neglectus*).

Blattodea Pests: German cockroaches (*Blattella germanica*), smoky brown cockroaches (*Periplaneta fuliginosa*), American cockroaches (*Periplaneta americana*), brown cockroaches (*Periplaneta brunnea*), and oriental cockroaches (*Blatta orientalis*).

Isoptera Pests: Yamato termites (*Reticulitermes speratus*), Formosan subterranean termites (*Coptotermes formosanus*), western drywood termites (*Incisitermes minor*), Daikoku drywood termites (Cryptotermes *domesticus*), Taiwan termites (*Odontotermes formosanus*), dry-wood termites (*Neotermes koshunensis*), red tree termites (*Glyptotermes satsumensis*), Nakajima termites (*Glyptotermes nakajimai*), black tree termites (*Glyptotermes fuscus*), Kodama termites (*Glyptotermes kodamai*), Kushimoto termites (*Glyptotermes kushimensis*), Japanese damp-wood termites (*Hodotermopsis japonica*), Koshuie termites (*Coptotermes guangzhoensis*), Amami termites (*Reticulitermes miyatakei*), yellow limb termites (*Reticulitermes flaviceps amamianus*), Kanmon termites (*Reticulitermes* sp.), wood-eating higher termites (*Nasutitermes takasagoensis*), Nitobe termites (*Pericapritermes nitobei*), Musha termites (*Sinocapritermes mushae*), and the like.

Acarina pests: spider mites such as two-spotted spider mites (*Tetranychus urticae*), kanzawai spider mites (*Tetranychus kanzawai*), citrus red mites (*Panonychus citri*), European red mites (*Panonychus ulmi*), and the genus *Origonikasu*; eriophyidae such as Mandarin orange rust mites (*Aculops pelekassi*), pink citrus rust mites (*Phyllocoptruta citri*), tomato rust mites (*Aculops lycopersici*), purple mites (*Calacarus carinatus*), tea rust mites (*Acaphylla theavagrans*), false pear rust mites (*Eriophyes chibaensis*), and apple rust mites (*Aculus schlechtendali*); white mites such as broad mites (*Polyphagotarsonemus latus*); false spider mites such as red and black flat mites (*Brevipalpus phoenicis*); peacock mites; ticks such as three-host ticks (*Haemaphysalis longicornis*), yellow ticks (*Haemaphysalis flava*), Taiwan leather ticks (*Dermacentor taiwanicus*), American dog ticks (*Dermacentor variabilis*), ovate hard ticks (*Ixodes ovatus*), taiga ticks (*Ixodes persulcatus*), black-legged ticks (*Ixodes scapularis*), lone star ticks (*Amblyomma americanum*), cattle ticks (*Boophilus microplus*), and brown dog ticks (*Rhipicephalus sanguineus*); flour mites such as mould mites (*Tyrophagus putrescentiae*) and acarid mites (*Tyrophagus similis*); acariform mites such as American house dust mites (*Dermatophagoides farinae*) and European house dust mites (*Dermatophagoides ptrenyssnus*); cheyletid mites such as hunting mites (*Cheyletus eruditus*), Malacca meat mites (*Cheyletus malaccensis*), Minami Tsumedani (*Cheyletus moorei*), and dog mites (*Cheyletiella yasguri*); itch mites such as ear mites (*Octodectes cynotis*) and itch mites (*Sacroptes scabiei*); follicle mites such as follicle mites (*Demodex canis*); Listrophorid mites; oribatid mites; parasitoid mites such as tropical rat mites (*Ornithonyssus bacoti*), northern fowl mites (*Ornithonyssus sylvairum*), and chicken mites (*Dermanyssus gallinae*); trombiculid mites such as red fiber sand mites (*Leptotrombidium akamushi*); and the like.

Acarina pests: Japanese foliage spiders (*Chiracanthium japonicum*), redback spiders (*Latrodectus hasseltii*), and the like.

Chilopoda: house centipedes (*Thereuonema hilgendorfi*), Chinese red-headed centipedes (*Scolopendra subspinipes*), and the like.

Diplopoda: garden millipedes (*Oxidus gracilis*), red millipedes (*Nedyopus tambanus*), and the like.

Isopoda: pill-bugs (*Armadillidium vulgare*), and the like.

Gastropoda: air-breathing land slugs (*Limax marginatus*), yellow slugs (*Limax flavus*), and the like.

A pest control agent of the present invention comprises the compound of the present invention and an inert carrier. In the present invention, the inert carrier refers to a bulking agent or a diluent used in epidemic-preventing and agricultural fields. In general, the pest control agent of the present invention has been formulated into an emulsion, an oil solution, powder, granules, a water-dispersible agent, a flowable agent, a microcapsule agent, an aerosol agent, a smoking agent, a poison bait agent, a resin formulation, a shampoo agent, a paste formulation, a foaming agent, a carbon dioxide gas formulation, and a tablet by mixing the compound of the present invention with an inert carrier, such as a solid carrier, liquid carrier, and gaseous carrier, and, as necessary, adding a surfactant and other auxiliary agents for a formulation. These formulations are processed into a mosquito coil, an electric mosquito repellent mat, a liquid mosquito repellent formulation, a smoking agent, a fumigant, a sheet formulation, a spot-on agent, or an oral treatment agent, and these are also used in some cases.

The pest control agent of the present invention comprises usually 0.01% by weight to 95% by weight of the compound of the present invention.

Examples of the solid carrier used during the formulation include fine powder and particulates, such as clays (kaolin clay, diatomaceous earth, bentonite, Fubasami clay, acid clay, and the like), synthetic hydrated silicon oxide, talc, ceramics, other inorganic minerals (sericite, quartz, sulfur, activated carbon, calcium carbonate, hydrated silica, and the like), and chemical fertilizers (ammonium sulfate, ammonium phosphate dibasic, ammonium nitrate, urea, ammonium chloride, and the like), and synthetic resins (polyethylene, polypropylene, polyacrylonitrile, polymethyl methacrylate, polyester resins such as polyethylene terephthalate, nylon resins such as nylon-6, nylon-11, and nylon-66, polyamide resins, polyvinyl chloride, polyvinylidene chloride, a vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, and the like), ketones (acetone, methyl ethyl ketone, cyclohexanone, and the like), aromatic hydrocarbons (toluene, xylene, ethylbenzene, dodecylbenzene, phenylxylylethane, methylnaphthalene, and the like), aliphatic hydrocarbons (hexane, cyclohexane, kerosine, gas oil, and the like), esters (ethyl acetate, butyl acetate, isopropyl myristate, ethyl oleate, diisopropyl adipate, diisobutyl adipate, propylene glycol monomethyl ether acetate, and the like), nitriles (acetonitrile, isobutyronitrile, and the like), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol), acid amides (N,N-dimethylformamide, N,N-dimethylacetamide, and the like), halogenated hydrocarbons (dichloromethane, trichloroethane, carbon tetrachloride, and the like), sulfoxides (dimethyl sulfoxide, and the like), propylene carbonate, and vegetable oils (soybean oil, cottonseed oil, and the like).

Examples of the gaseous carrier include fluorocarbon, butane gas, liquefied petroleum gas (LPG), dimethyl ether, and carbon dioxide gas.

Examples of the surfactant include non-ionic surfactants such as polyoxyethylene alkyl ether, polyoxyethylene alkylaryl ether, and polyethylene glycol fatty acid ester; and anionic surfactants such as alkyl sulfonate, alkyl benzene sulfonate, and alkyl sulfate.

Examples of the auxiliary agent for a formulation include a sticking agent, a dispersing agent, a colorant and a stabilizer, and specific examples thereof include casein, gelatin, sugars (starch, gum arabic, cellulose derivatives, alginic acid, and the like), lignin derivatives, bentonite, synthetic water-soluble polymers (polyvinyl alcohol, polyvinyl pyrrolidone, polyacrylic acids, and the like), PAP (acidic isopropyl phosphate), BHT (2,6-di-t-butyl-4-methylphenol), and BHA (a mixture of 2-t-butyl-4-methoxyphenol and 3-t-butyl-4-methoxyphenol).

Examples of the base material of the resin formulation include vinyl chloride-based polymers and polyurethanes, and plasticizers such as phthalates (dimethyl phthalate, dioctyl phthalate, and the like), adipates, or stearic acid may be added to these base materials, as necessary. The resin formulation is obtained by kneading a compound and the base material using a typical kneading device and molding the resulting product by injection molding, extrusion molding, or a press molding, and may be further processed into a resin formulation having a plate shape, a film shape, a tape shape, a net shape, or a string shape through a step of molding or cutting, as necessary. These resin formulations are processed into, for example, an animal collar, an animal ear tag, a sheet formulation, an attracting string, or a horticultural support.

Examples of the base material of a poison bait include grain flour, vegetable oil, sugar, and crystalline cellulose, and an antioxidant such as dibutylhydroxytoluene or nordihydroguaiaretic acid, a preservative such as dehydroacetic acid, an accidental ingestion-preventing agent for preventing children and pets from accidentally ingesting, such as red pepper powder, or a pest-attracting flavoring such as cheese flavoring, onion flavoring, or peanut oil is further added, as necessary.

By directly applying the pest control agent of the present invention to pests and/or applying the pest control agent of the present invention to a habitat, pests may be controlled.

A method for controlling pests in the present invention is performed by directly applying an effective amount of the compound of the present invention to pests and/or applying an effective amount of the compound of the present invention to a habitat (plants, soil, the inside of a house, animal bodies, etc.) of the pests. In the method for controlling pests of the present invention, the compound of the present invention is usually used in the form of a pest control agent of the present invention.

In a case of using the pest control agent of the present invention for controlling pests in agricultural fields, the application amount thereof is usually 1 g to 10000 g of the amount of compound of the present invention per 10000 m$^2$. In a case where the pest control agent of the present invention has been formulated into an emulsion, a water-dispersible agent, a flowable agent, etc., in general, the compound of the present invention is applied by being diluted in water so that the concentration of the active ingredients becomes 0.01 ppm to 10000 ppm.

Granules, powder, etc. are generally applied to the subject as they are.

These formulations or water-diluted solutions of the formulations may be scattered directly onto pests or onto plants, such as crops, to be protected from the pests.

Alternately, soil in cultivated land may be treated with the formulations or the water-diluted solutions in order to control pests which live in the soil.

In addition, the treatment may be performed through methods, such as winding of a resin formulation which has been processed into a sheet shape or a string shape onto crops, stretching the resin formulation across the vicinity of the crops, and spreading the resin formulation onto soil near the roots.

In the case of using the pest control agent of the present invention for controlling pests which live inside of a house, in general, the application amount thereof is 0.01 mg to 1000 mg of the amount of compound of the present invention per 1 m$^2$ of the treatment area when being treated on a surface, and is 0.01 mg to 500 mg of the amount of compound of the present invention per 1 m$^3$ of the treatment space when being treated in a space. In a case where the pest control agent of the present invention has been formulated into an emulsion, a water-dispersible agent, a flowable agent, etc, in general, the compound of the present invention is applied by being diluted in water so that the concentration of the active ingredients becomes 0.1 ppm to 10000 ppm. An oil solution, an aerosol agent, a smoking agent, a poison bait agent, etc. are generally applied to the subject as they are.

In a case where the pest control agent of the present invention is used for controlling ectoparasite of domestic animals such as cattle, horses, pigs, sheep, goats, or chickens, or small animals such as dogs, cats, rats, or mice, the pest control agent may be used for domestic animals or animals by known veterinary methods. As a specific usage method, in the case of a systemic control purpose, the agent is administered, for example, in a form of a tablet, mixing in feed, or a suppository, or by (intramuscular, subcutaneous, intravenous, or intraperitoneal) injection, and in the case of a non-systemic control purpose, a method of spraying an oil or an aqueous solution, a method of performing a pour-on treatment or a spot-on treatment, a method of washing an animal with a shampoo formulation, or a method of attaching a collar or an ear tag of a resin formulation to an animal is used. The amount of the compound of the present invention in the case being administered to an animal body is within a range of 0.1 mg to 1000 mg, usually, with respect to 1 kg of the body weight of the animal.

The pest control agent of the present invention may be used in agricultural land in which the following crops have been cultivated.

Farm products: corn, rice, wheat, barley, rye, oats, sorghum, cotton, soybeans, peanuts, buckwheat, sugar beets, rapeseeds, sunflowers, sugar cane, tobacco, and the like.

Vegetables: solanaceous vegetables (eggplants, tomatoes, bell peppers, peppers, potatoes, and the like), cucurbit vegetables (cucumbers, pumpkins, zucchinis, watermelons, melons, and the like), cruciferous vegetables (radishes, turnips, horseradishes, kohlrabi, chinese cabbage, cabbage, mustard, broccoli, cauliflower, and the like), asteraceae vegetables (burdock, garland *chrysanthemum*, artichoke, lettuce, and the like), liliaceae vegetables (spring onions, onions, garlic, asparagus), umbelliferae vegetables (carrots, parsley, celery, parsnips, and the like), chenopodiaceae vegetables (spinach, chard, and the like), labiatae vegetables (*perilla*, mint, basil, and the like), strawberries, sweet potatoes, Japanese yams, taro, and the like.

Fruit trees: pomaceous fruits (apples, European pears, Japanese pears, Chinese quinces, quinces, and the like), stone fruits (peaches, Japanese plums, nectarines, Chinese plums, cherries, apricots, prunes, and the like), citrus (satsuma mandarins, oranges, lemons, limes, grapefruits, and the like), nut trees (chestnut, walnut, hazelnut, almond, pistachio, cashew nut, macadamia nut, and the like), berry fruits (blueberries, cranberries, blackberries, raspberries, and the like), grapes, oysters, olives, loquats, bananas, coffee, date palms, coconuts, oil palms, and the like.

Trees other than fruit trees: tea, mulberry, flowering trees (azalea, *camellia, hydrangea*, sasanqua, Japanese star anise, cherry, tulip tree, crape myrtle, fragrant olive, and the like), street trees (ash, birch tree, dogwood, *eucalyptus*, ginkgo, lilac, maple, oak, poplar, *cercis*, sweetgum, sycamore, Japanese *zelkova*, Japanese arborvitae, fir tree, hemlock, juniper, pine, spruce, yew, elm, horse chestnut, and the like), sweet *viburnum*, podocarpus, cedar, Japanese cypress, croton, Japanese spindle tree, Japanese *photinia*, and the like.

Lawn: grasses (zoysiagrass, *zoysia matrella*, and the like), bermuda grasses (bermuda grass, and the like), bent grasses (creeping bent, creeping bent grass high, thread creeping bent grass, and the like), blue grasses (kentucky bluegrass, rough bluegrass, and the like), fescues (*festuca arundinacea*, chewings fescue, creeping red fescue, and the like), ryegrasses (darnel, rye grass, and the like), orchard grass, timothy grass, and the like.

Others: flowering plants (rose, carnation, *chrysanthemum*, lisianthus, *gypsophila, gerbera*, marigold, *salvia, petunia, verbena*, tulip, aster, gentian, lily, pansies, cyclamen, orchid, lily of the valley, lavender, stock, ornamental cabbage, *primula*, poinsettia, *gladiolus*, cattleya, daisy, cymbidium, *begonia*, and the like), biofuel plants (jatropha, curcas, safflower, camelina, switchgrass, *miscanthus*, reed canarygrass, giant reed, kenaf, cassava, willow, algae, and the like), foliage plants, and the like.

Genetically modified crops are also included in "crops".

It is possible to use the pest control agent of the present invention by mixing with or together with other insecticides, acaricides, nematicides, fungicides, plant growth regulators, herbicides, synergists, and phytotoxicity reducing agents. Examples of active ingredients of the insecticides, the acaricides, the nematicides, the fungicides, the herbicides, the synergists, and the phytotoxicity reducing agents are shown as follows.

Active Ingredients of Insecticides (1) Organic Phosphorus Compounds

Acephate, aluminium phosphide, butathiofos, cadusafos, chlorethoxyfos, chlorfenvinphos, chlorpyrifos, chlorpyrifos-methyl, cyanophos:CYAP, diazinon, dichlorodiisopropyl ether (DCIP), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, and cadusafos.

(2) Carbamate Compounds

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, and aldicarb.

(3) Pyrethroid Compounds

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl(EZ)-(1RS,3RS;1RS, 3SR)-2,2-dimethyl-3-prop-1-enylcyclopropanecarboxylate, 2,3,5,6-tetrafluoro-4-methyl-benzyl(EZ)-(1RS,3RS;1RS, 3SR)-2,2-dimethyl-3-prop-1-enylcyclopropanecarboxylate, 2,3,5,6-tetrafluoro-4-(methoxymethyl)benzyl(1RS,3RS; 1RS,3SR)-2,2-dimethyl-3-(2-methyl-1-propenyl)cyclopropanecarboxylate, and 2,3,5,6-tetrafluoro-4-(methoxymethyl)benzyl(EZ)-(1RS,3RS; RS,3SR)-2,2-dimethyl-3-(2-cyano-1-propenyl)cyclopropanecarboxylate.

(4) Nereistoxin Compounds

Cartap, bensultap, thiocyclam, monosultap, and bisultap.

(5) Neonicotinoid Compounds

Imidacloprid, nitenpyram, acetamiprid, thiamethoxam, thiacloprid, dinotefuran, and clothianidin.

(6) Benzoylurea Compounds

Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds

Acetoprole, ethiprole, fipronil, vaniliprole, pyriprole, and pyrafluprole.

(8) Bt Toxin

Viable spores derived from *Bacillus thuringiensis* bacteria and crystal toxins produced from *Bacillus thuringiensis* bacteria, and a mixture thereof;

(9) Hydrazine Compounds Chromafenozide, halofenozide, methoxyfenozide, and tebufenozide.

(10) Organic Chlorine Compounds

Aldrin, dieldrin, dienochlor, endosulfan, and methoxychlor.

(11) Other Active Ingredients of Insecticides

Machine oil, nicotine-sulfate; avermectin-B, bromopropylate, buprofezin, chlorphenapyr, cyantraniliprole, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metamammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, and cyantraniliprole, a compound represented by the following Formula (K)

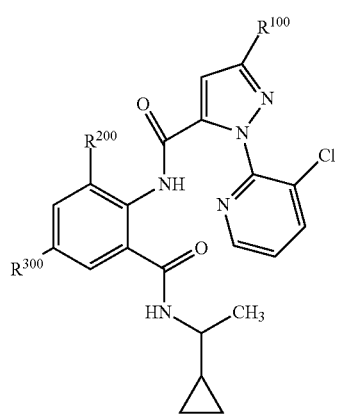

[wherein $R^{100}$ represents a chlorine atom, a bromine atom, or a trifluoromethyl group, $R^{200}$ represents a chlorine atom, a bromine atom, or a methyl group, and $R^{300}$ represents a chlorine atom, a bromine atom, or a cyano group.], and a compound represented by the following Formula (L)

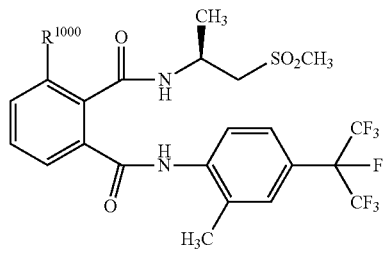

[wherein $R^{1000}$ represents a chlorine atom, a bromine atom, or an iodine atom.].

Active Ingredients of Acaricides

Acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicides

DCIP, fosthiazate, levamisole hydrochloride (levamisol), methylisothiocyanate, morantel tartarate, and imicyafos.

Active Ingredients of Fungicides

Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

cyclic amine fungicidal compounds such as fenpropimorph, tridemorph, and fenpropidin;

Benzimidazole fungicidal compounds such as carbendezim, benomyl, thiabendazole, and thiophanate-methyl; and procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil, and tiadinil.

Active Ingredients of Plant Growth Regulators

Ethephon, chlormequat-chloride, mepiquat-chloride, Gibberellin A represented by Gibberellin A3, abscisic acid, Kinetin, benzyladenine, 1,3-diphenyl urea, forchlorfenuron, thidiazuron, 4-oxo-4-(2-phenylethyl)aminobutyric acid, methyl 5-(trifluoromethyl)benzo[b]thiophene-2-carboxylate, and 5-(trifluoromethyl)benzo[b]thiophene-2-carboxylate.

Active Ingredients of Herbicides (1) Phenoxyfatty Acid Herbicidal Compounds 2,4-PA, MCP, MCPB, phenothiol, mecoprop, fluroxypyr, triclopyr, clomeprop, and naproanilide.

(2) Benzoic Acid Herbicidal Compounds 2,3,6-TBA, dicamba, clopyralid, picloram, aminopyralid, quinclorac, and quinmerac.

(3) Urea Herbicidal Compounds

Diuron, linuron, chlortoluron, isoproturon, fluometuron, isouron, tebuthiuron, methabenzthiazuron, cumyluron, daimuron, and methyl-daimuron.

(4) Triazine Herbicidal Compounds

Atrazine, ametoryn, cyanazine, simazine, propazine, simetryn, dimethametryn, prometryn, metribuzin, triaziflam, and indaziflam.

(5) Bipyridinium Herbicidal Compounds

Paraquat and diquat.

(6) Hydroxy Benzonitrile Herbicidal Compounds

Bromoxynil and ioxynil.

(7) Dinitroaniline Herbicidal Compounds

Pendimethalin, prodiamine, and trifluralin.

(8) Organic Phosphorus Herbicidal Compounds

Amiprofos-methyl, butamifos, bensulide, piperophos, anilofos, glyphosate, glufosinate, glufosinate-P, and bialaphos.

(9) Carbamate Herbicidal Compounds

Di-allate, tri-allate, EPTC, butylate, benthiocarb, esprocarb, molinate, dimepiperate, swep, chlorpropham, chlorpropham, phenmedipham, phenisopham, pyributicarb, and asulam.

(10) Acid Amide Herbicidal Compounds

Propanil, propyzamide, bromobutide, and etobenzanid.

(11) Chloroacetanilide Herbicidal Compounds

Acetochlor, alachlor, butachlor, dimethenamid, propachlor, metazachlor, metolachlor, pretilachlor, thenylchlor, and pethoxamid.

(12) Diphenyl Ether Herbicidal Compounds

Acifluorfen (acifluorfen-sodium), bifenox, oxyfluorfen, lactofen, fomesafen, chlomethoxynil, and aclonifen.

(13) Cyclic Imide Herbicidal Compounds

Oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds

Benzofenap, pyrazolate, pyrazoxyfen, topramezone, and pyrasulfotole.

(15) Triketone Herbicidal Compounds

Isoxaflutole, benzobicyclon, sulcotrione, mesotrione, tembotrione, and tefuryltrione.

(16) Aryloxyphenoxypropionic Acid Herbicidal Compounds

Clodinafop-propargyl, cyhalofop-butyl, diclofop-methyl, fenoxaprop-ethyl, fluazifop-butyl, haloxyfop-methyl, quizalofop-ethyl, and metamifop.

(17) Trione Oxime Herbicidal Compounds

Alloxydim (alloxydim-sodium), sethoxydim, butroxydim, clethodim, cloproxydim, cycloxydim, tepraloxydim, tralkoxydim, and profoxydim.

(18) Sulfonylurea Herbicidal Compounds

Chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds

Imazamethabenz-methyl, imazamethapyr, imazamox, imazapyr, imazaquin, and imazethapyr.

(20) Sulfonamide Herbicidal Compounds

Flumetsulam, metosulam, diclosulam, florasulam, cloransulam-methyl, penoxsulam, and pyroxsulam.

(21) Pyrimidinyloxy Benzoic Acid Herbicidal Compounds

Pyrithiobac-sodium, bispyribac-sodium, pyriminobac-methyl, pyribenzoxim, pyriftalid, and pyrimisulfan.

(22) Other Herbicidal Compounds

Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergists

Piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

Active Ingredients of Phytotoxicity Reducing Agent

Benoxacor, cloquintocet-mexyl, cyometrinil, dichlormid, fenchlorazole-ethyl, fenclorim, flurazole, furilazole, mefenpyr-diethyl, MG191, oxabetrinil, allidochlor, isoxadifen-ethyl, cyprosulfamide, fluxofenim, 1,8-naphthalic anhydride, and AD-67.

EXAMPLES

Hereinafter, the present invention will be described in more detail with reference to production examples, formulation examples, and test examples, but the present invention is not limited to these examples.

In the present specification, Me represents a methyl group, Et represents an ethyl group, Pr represents a propyl group, i-Pr represents an isopropyl group, c-Pr represents a cyclopropyl group, t-Bu represents a t-butyl group, Ac represents an acetyl group, OMe represents a methoxy group, OEt represents an ethoxy group, OPr represents a propyloxy group, Oi-Pr represents an isopropyloxy group, Ph represents a phenyl group, 1-Nap represents a 1-naphthyl group, 2-Nap represents a 2-naphthyl group, 2-Py represents a 2-pyridyl group, 3-Py represents a 3-pyridyl group, 4-Py represents a 4-pyridyl group, 2-Thia represents a 2-thiazolyl group, 4-Thia represents a 4-thiazolyl group, 2-Thie represents a 2-thienyl group, 3-Thie represents a 3-thienyl group, 2-Pyrr represents a 2-pyrrolyl group, 3-Pyrr represents a 3-pyrrolyl group, 2-Thia represents a 2-thiazolyl group, 4-Thia represents a 4-thiazolyl group, 5-Thia represents a 5-thiazolyl group, 2-Fur represents a 2-furyl group, and 3-Fur represents a 3-furyl group.

First, production examples of the compound of the present invention will be shown.

Production Example 1

In a nitrogen atmosphere, a 1.6 M n-butyl lithium hexane solution (2.3 ml, 3.6 mmol) was added dropwise to a diethyl ether solution (15 ml) of 900 mg (3 mmol) of 2-(2-methoxybenzyloxy)-5-bromothiazole (Compound (4-1)) at −78° C. over a period of 5 minutes, and the mixture was stirred at −78° C. for 20 minutes. A diethyl ether solution (5 ml) of 558 mg (6 mmol) of dimethyl disulfide was added dropwise to the reaction mixture at −78° C., and after stirring at −78° C. for 1 hour, the temperature was raised to 0° C. After a saturated ammonium chloride aqueous solution was added to the reaction mixture, the organic layer was separated, and the aqueous layer was extracted with ethyl acetate. After the organic layers were combined and concentrated, the residue was purified by silica gel column chromatography, whereby 320 mg of 2-(2-methoxybenzyloxy)-5-methylthiothiazole (compound (1a-1) of the present invention) was obtained.

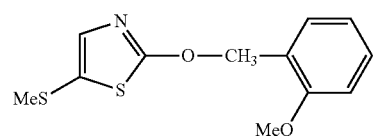 [SMILES: COc1ccccc1COc1ncc(SC)s1]

$^1$H-NMR (CDCl$_3$) δ: 2.39 (3H, s), 3.85 (3H, s), 5.47 (2H, s), 6.91 (1H, d, J=8.3 Hz), 6.97 (1H, dt, J=1.5, 7.5 Hz), 7.17 (1H, s), 7.34 (1H, dt, J=1.5, 7.5 Hz), 7.42 (1H, dd, J=1.5, 7.5 Hz).

The reaction of the following formula was performed in the same manner as in Production Example 1 except that a compound (4) was used instead of 2-(2-methoxybenzyloxy)-5-bromothiazole and a compound (8) was used instead of dimethyl disulfide, whereby compounds (1a-2) to (1a-61) and (1a-63) to (1a-91) of the present invention represented by Formula (1a) described below were obtained.

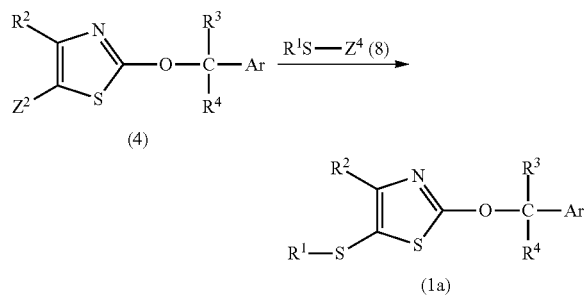

$R^1$, $R^2$, $R^3$, $R^4$, Ar, $Z^2$, and $Z^4$ in the formula represent the combinations described in [Table 1] to [Table 4] below.

TABLE 1

| Compound of the present invention | $R^1$ | $R^2$ | $R^3$ | $R^4$ | Ar | $Z^2$ | $Z^4$ |
|---|---|---|---|---|---|---|---|
| 1a-2 | Me | H | H | H | 2-Me—Ph | Br | SMe |
| 1a-3 | Me | H | H | H | 2-Cl—Ph | Br | SMe |
| 1a-4 | Me | H | H | H | 2-F—Ph | Br | SMe |
| 1a-5 | Me | H | H | H | 2-F-6-OMe—Ph | Br | SMe |
| 1a-6 | Me | Me | H | H | 2-OMe—Ph | Br | SMe |
| 1a-7 | Et | H | H | H | 2-OMe—Ph | Br | SEt |
| 1a-8 | Pr | H | H | H | 2-OMe—Ph | Br | SPr |
| 1a-9 | Me | H | H | H | 3-Py | Br | SMe |
| 1a-10 | Me | H | H | H | 2,4,6-Me$_3$—Ph | Br | SMe |
| 1a-11 | Me | H | H | H | 2,3,4-(OMe)$_3$—Ph | Br | SMe |
| 1a-12 | Me | H | H | H | Ph | Br | SMe |
| 1a-13 | Me | H | H | H | 1-OMe-2-Nap | Br | SMe |
| 1a-14 | Me | H | H | H | 2-OMe-3-Py | Br | SMe |
| 1a-15 | Me | H | H | H | 2,5-Me$_2$—Ph | Br | SMe |
| 1a-16 | Me | H | H | H | 2-F-6-Me—Ph | Br | SMe |
| 1a-17 | Me | H | H | H | 3-F-2-Me—Ph | Br | SMe |
| 1a-18 | Me | H | H | H | 4-F-2-Me—Ph | Br | SMe |
| 1a-19 | Me | H | H | H | 5-F-2-Me—Ph | Br | SMe |
| 1a-20 | Me | H | H | H | 4-Me-3-Thie | Br | SMe |
| 1a-21 | Me | H | H | H | 3-F-2-OMe—Ph | Br | SMe |
| 1a-22 | Me | H | H | H | 4-F-2-OMe—Ph | Br | SMe |
| 1a-23 | Me | H | H | H | 5-F-2-OMe—Ph | Br | SMe |
| 1a-24 | Me | H | H | H | 2,5-(OMe)$_2$—Ph | Br | SMe |
| 1a-25 | Me | H | H | H | 2-OMe-6-Me—Ph | Br | SMe |

TABLE 2

| Compound of the present invention | $R^1$ | $R^2$ | $R^3$ | $R^4$ | Ar | $Z^2$ | $Z^4$ |
|---|---|---|---|---|---|---|---|
| 1a-26 | Me | H | H | H | 2-OMe-5-Me—Ph | Br | SMe |
| 1a-27 | Me | H | H | H | 2-OMe-4-Me—Ph | Br | SMe |
| 1a-28 | Me | H | H | H | 2-OMe-3-Me—Ph | Br | SMe |
| 1a-29 | Me | H | H | H | 3-Cl-2-OMe—Ph | Br | SMe |
| 1a-30 | Me | H | H | H | 4-Cl-2-OMe—Ph | Br | SMe |
| 1a-31 | Me | H | H | H | 5-Cl-2-OMe—Ph | Br | SMe |
| 1a-32 | Me | H | H | H | 2-OEt—Ph | Br | SMe |

TABLE 2-continued

| Compound of the present invention | $R^1$ | $R^2$ | $R^3$ | $R^4$ | Ar | $Z^2$ | $Z^4$ |
|---|---|---|---|---|---|---|---|
| 1a-33 | Me | H | H | H | 2-OPr—Ph | Br | SMe |
| 1a-34 | Me | H | H | H | 2-Oi-Pr—Ph | Br | SMe |
| 1a-35 | Me | H | H | H | 2-CH$_2$=CH—Ph | Br | SMe |
| 1a-36 | Me | H | H | H | 2-OCF$_3$—Ph | Br | SMe |
| 1a-37 | Me | H | H | H | 3-Thie | Br | SMe |
| 1a-38 | Me | H | H | H | 2-Me-3-Thie | Br | SMe |
| 1a-39 | Me | H | H | H | 4-OMe-3-Thie | Br | SMe |
| 1a-40 | Et | H | H | H | 5-F-2-Me—Ph | Br | SEt |
| 1a-41 | Et | H | H | H | 2-F-6-Me—Ph | Br | SEt |
| 1a-42 | Et | H | H | H | 4-F-2-Me—Ph | Br | SEt |
| 1a-43 | Me | H | H | H | 2,4-Me$_2$—Ph | Br | SMe |
| 1a-44 | Me | H | H | H | 3-F—Ph | Br | SMe |
| 1a-45 | Me | H | H | H | 4-F—Ph | Br | SMe |
| 1a-46 | Me | H | H | H | 2-CN—Ph | Br | SMe |
| 1a-47 | Me | H | H | H | 2-OPh—Ph | Br | SMe |
| 1a-48 | Me | H | H | H | 2-CF$_3$—Ph | Br | SMe |
| 1a-49 | Me | H | H | H | 2-NMe$_2$—Ph | Br | SMe |
| 1a-50 | Me | H | H | H | 2-SMe—Ph | Br | SMe |

TABLE 3

| Compound of the present invention | $R^1$ | $R^2$ | $R^3$ | $R^4$ | Ar | $Z^2$ | $Z^4$ |
|---|---|---|---|---|---|---|---|
| 1a-51 | Me | H | H | H | 2-Pr—Ph | Br | SMe |
| 1a-52 | Me | H | H | H | 2-i-Pr—Ph | Br | SMe |
| 1a-53 | Me | H | H | H | 2-t-Bu—Ph | Br | SMe |
| 1a-54 | Me | H | H | H | 2,3-F$_2$—Ph | Br | SMe |
| 1a-55 | Me | H | H | H | 2,4-F$_2$—Ph | Br | SMe |
| 1a-56 | Me | H | H | H | 2,5-F$_2$—Ph | Br | SMe |
| 1a-57 | Me | H | H | H | 2,6-F$_2$—Ph | Br | SMe |
| 1a-58 | Me | H | H | H | 2-Me-3-Py | Br | SMe |
| 1a-59 | Me | H | H | H | 3-Me-2-Py | Br | SMe |
| 1a-60 | Me | H | H | H | 4-Me-3-Py | Br | SMe |
| 1a-61 | Me | H | H | H | 3-Me-4-Py | Br | SMe |
| 1a-63 | Me | H | H | H | 2-OCH$_2$CF$_3$—Ph | Br | SMe |
| 1a-64 | Me | H | H | H | 3-Cl—Ph | Br | SMe |
| 1a-65 | Me | H | H | H | 4-Cl—Ph | Br | SMe |
| 1a-66 | Me | H | H | H | 2-CH$_2$OMe—Ph | Br | SMe |
| 1a-67 | Me | H | H | H | 2-Br—Ph | Br | SMe |
| 1a-68 | Me | H | H | H | 2-Ph—Ph | Br | SMe |
| 1a-69 | Me | H | H | H | 2-CH$_2$CF$_3$—Ph | Br | SMe |
| 1a-70 | Me | H | H | H | 2,3-Cl$_2$—Ph | Br | SMe |
| 1a-71 | Me | H | H | H | 2,4-Cl$_2$—Ph | Br | SMe |
| 1a-72 | Me | H | H | H | 2,5-Cl$_2$—Ph | Br | SMe |
| 1a-73 | Me | H | H | H | 2,6-Cl$_2$—Ph | Br | SMe |
| 1a-74 | Me | H | H | H | 2-Fur | Br | SMe |
| 1a-75 | Me | H | H | H | 3-Fur | Br | SMe |

TABLE 4

| Compound of the present invention | $R^1$ | $R^2$ | $R^3$ | $R^4$ | Ar | $Z^2$ | $Z^4$ |
|---|---|---|---|---|---|---|---|
| 1a-76 | Me | H | H | H | 2-Me-3-Fur | Br | SMe |
| 1a-77 | Me | H | H | H | 2,6-Me$_2$—Ph | Br | SMe |
| 1a-78 | Me | H | H | H | 2,3-Me$_2$—Ph | Br | SMe |
| 1a-79 | Me | H | H | H | 3-Cl-2-Me—Ph | Br | SMe |
| 1a-80 | Me | H | H | H | 4-Cl-2-Me—Ph | Br | SMe |
| 1a-81 | Me | H | H | H | 2-Cl-6-Me—Ph | Br | SMe |
| 1a-82 | Me | H | H | H | 5-Cl-2-Me—Ph | Br | SMe |
| 1a-83 | Me | H | H | H | 3-OMe-2-Me—Ph | Br | SMe |
| 1a-84 | Me | H | H | H | 4-OMe-2-Me—Ph | Br | SMe |
| 1a-85 | Me | H | H | H | 2-Me-5-CF$_3$—Ph | Br | SMe |
| 1a-86 | Me | H | H | H | 5-OMe-2-Me—Ph | Br | SMe |
| 1a-87 | Me | H | Me | H | 2-Me—Ph | Br | SMe |
| 1a-88 | Me | H | Et | H | 2-Me—Ph | Br | SMe |

TABLE 4-continued

| Compound of the present invention | R¹ | R² | R³ | R⁴ | Ar | Z² | Z⁴ |
|---|---|---|---|---|---|---|---|
| 1a-89 | Me | H | Pr | H | 2-Me—Ph | Br | SMe |
| 1a-90 | Me | H | i-Pr | H | 2-Me—Ph | Br | SMe |
| 1a-91 | Me | H | c-Pr | H | 2-Me—Ph | Br | SMe |

TABLE 5

| Compound of the present invention | R¹ | R² | R³ | R⁴ | Ar | Z⁴ |
|---|---|---|---|---|---|---|
| 1a-202 | Et | H | H | H | 2-Et—Ph | SEt |
| 1a-203 | Me | H | H | H | 2-Et—Ph | SMe |
| 1a-204 | Me | H | Me | H | 2-Nap | SMe |

Production Example 2

In a nitrogen atmosphere, a tetrahydrofuran-ethylbenzene-heptane solution (2.4 ml, 3.6 mmol) of 1.5 M lithium diisopropylamide was added dropwise to a diethyl ether solution (15 ml) of 615 mg (3 mmol) of 2-(2-methylbenzyloxy)thiazole (Compound (9-1)) at −78° C. over a period of 5 minutes, and the mixture was stirred at −78° C. for 40 minutes. A tetrahydrofuran solution (10 ml) of 732 mg (6 mmol) of diethyl disulfide was added dropwise to the reaction mixture at −78° C., and after stirring at −78° C. for 1 hour, the temperature was raised to 0° C. After a saturated ammonium chloride aqueous solution was added to the reaction mixture, the organic layer was separated, and the aqueous layer was extracted with ethyl acetate. After the organic layers were combined and concentrated, the residue was purified by silica gel column chromatography, whereby 983 mg of 2-(2-methylbenzyloxy)-5-ethylthiothiazole (compound (1a-201) of the present invention) was obtained.

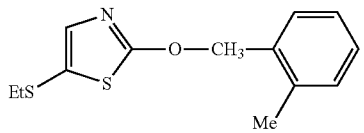

$^1$H-NMR (CDCl$_3$)δ: 1.26 (3H, t, J=7.5 Hz), 2.39 (3H, s), 2.69 (2H, q, J=7.5 Hz), 5.42 (2H, s), 7.17 (1H, s), 7.25 (3H, m), 7.39 (1H, m).

The reaction of the following formula was performed in the same manner as in Production Example 2 except that a compound (9) was used instead of 2-(2-methylbenzyloxy)thiazole and a compound (8) was used instead of diethyl disulfide, whereby compounds (1a-202) to (1a-204) of the present invention represented by Formula (1a) described below were obtained.

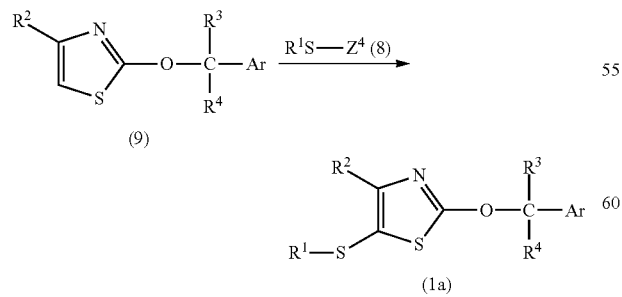

R¹, R², R³, R⁴, Ar, and Z⁴ in the formula represent the combinations described in [Table 5] below.

Production Example 3

A mixture of 2.67 g (10 mmol) of the compound (1a-1) and a chloroform solution (100 ml) of 2.93 g (12 mmol) of 70% 3-chloroperbenzoic acid was stirred at room temperature for 2 hours. A sodium thiosulfate aqueous solution was added to the reaction mixture, and the organic layer was separated. After the organic layer was washed two times with a sodium hydrogen carbonate aqueous solution, the organic layer was concentrated. The residue was purified by silica gel column chromatography, whereby 1.41 g of 2-(2-methoxybenzyloxy)-5-methylsulfinylthiazole (compound (1b-1) of the present invention) and 0.42 g of 2-(2-methoxybenzyloxy)-5-methylsulfonylthiazole (compound (1c-1) of the present invention) were obtained.

Compound (1b-1)

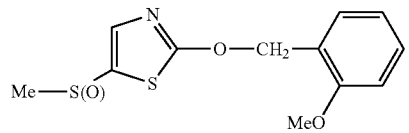

$^1$H-NMR (CDCl$_3$)δ: 2.92 (3H, s), 3.86 (3H, s), 5.54 (2H, s), 6.91-7.03 (2H, m), 7.32-7.40 (2H, m), 7.55 (1H, s).

Compound (1c-1)

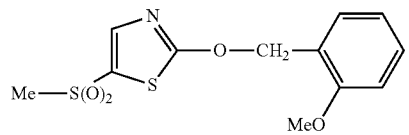

$^1$H-NMR (CDCl$_3$)δ: 3.17 (3H, s), 3.86 (3H, s), 5.54 (2H, s), 6.91-7.03 (2H, m), 7.32-7.40 (2H, m), 7.76 (1H, s).

The reaction of the following formula was performed in the same manner as in Production Example 3 except that a compound (1a) was used instead of the compound (1a-1) of the present invention, whereby compounds (1b-2) and (1b-12) of the present invention represented by Formula (1b) described below and compounds (1c-2) and (1c-12) of the present invention represented by Formula (1c) described below were obtained.

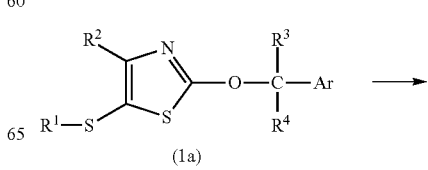

-continued

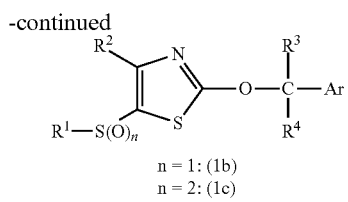

n = 1: (1b)
n = 2: (1c)

$R^1$, $R^2$, $R^3$, $R^4$, Ar, and n in the formula represent the combinations described in [Table 6] below.

TABLE 6

| Compound | $R^1$ | $R^2$ | $R^3$ | $R^4$ | Ar | n |
|---|---|---|---|---|---|---|
| 1b-2 | Me | H | H | H | 2-Me—Ph | 1 |
| 1c-2 | Me | H | H | H | 2-Me—Ph | 2 |
| 1b-12 | Me | H | H | H | Ph | 1 |
| 1c-12 | Me | H | H | H | Ph | 2 |

The $^1$H-NMR data of each of the compounds (1a-2) to (1a-61), (1a-63) to (1a-91), (1a-202) to (1a-204), (1b-2), (1c-2), (1b-12), and (1c-12) are described below.

Compound (1a-2) of Present Invention
$^1$H-NMR (CDCl$_3$)δ: 2.38 (3H, s), 2.39 (3H, s), 5.41 (2H, s), 7.17 (1H, s) 7.16-7.28 (3H, m), 7.37-7.42 (1H, m).

Compound (1a-3) of Present Invention
$^1$H-NMR (CDCl$_3$)δ: 2.39 (3H, s), 5.52 (2H, s), 7.16 (1H, s) 7.27-7.37 (2H, m), 7.38-7.42 (1H, m), 7.47-7.52 (1H, m).

Compound (1a-4) of Present Invention
$^1$H-NMR (CDCl$_3$)δ: 2.39 (3H, s), 5.48 (2H, s), 7.09-7.18 (2H, m), 7.16 (1H, s) 7.08-7.18 (1H, m), 7.43-7.57 (1H, m).

Compound (1a-5) of Present Invention
$^1$H-NMR (CDCl$_3$)δ: 2.38 (3H, s), 3.85 (3H, s), 5.48 (2H, s), 6.69-6.76 (2H, m), 7.18 (1H, s) 7.29-7.36 (1H, m).

Compound (1a-6) of Present Invention
$^1$H-NMR (CDCl$_3$)δ: 2.30 (3H, s), δ: 2.36 (3H, s), 3.85 (3H, s), 5.42 (2H, s), 6.91 (1H, d, J=8.3 Hz), 6.97 (1H, dt, J=1.5, 7.5 Hz), 7.34 (1H, dt, J=1.5, 7.5 Hz), 7.42 (1H, dd, J=1.5, 7.5 Hz).

Compound (1a-7) of Present Invention
$^1$H-NMR (CDCl$_3$)δ: 1.26 (3H, t, J=7.2 Hz), 2.36 (2H, q, J=7.2 Hz), 3.85 (3H, s), 5.47 (2H, s), 6.91 (1H, d, J=8.3 Hz), 6.97 (1H, dt, J=1.5, 7.5 Hz), 7.14 (1H, s) 7.34 (1H, dt, J=1.5, 7.5 Hz), 7.42 (1H, dd, J=1.5, 7.5 Hz).

Compound (1a-8) of Present Invention
$^1$H-NMR (CDCl$_3$)δ: 0.99 (3H, t, J=7.2 Hz), 1.60 (2H, m), 2.66 (2H, t, J=7.2 Hz), 3.84 (3H, s), 5.47 (2H, s), 6.91 (1H, d, J=8.3 Hz), 6.97 (1H, dt, J=1.5, 7.5 Hz), 7.15 (1H, s), 7.34 (1H, dt, J=1.5, 7.5 Hz), 7.42 (1H, dd, J=1.5, 7.5 Hz).

Compound (1a-9) of Present Invention
$^1$H-NMR (CDCl$_3$)δ: 2.39 (3H, s), 5.45 (2H, s), 7.16 (1H, s), 7.37 (1H, m), 7.79 (1H, m), 8.62 (1H, m), 8.70 (1H, m).

Compound (1a-10) of Present Invention
$^1$H-NMR (CDCl$_3$) δ value: 2.28 (3H, s), 2.37 (6H, s), 2.39 (3H, s), 5.45 (2H, s), 6.89 (2H, s), 7.17 (1H, s).

Compound (1a-11) of Present Invention
$^1$H-NMR (CDCl$_3$)δ: 2.31 (3H, s), 3.86 (3H, s), 3.88 (3H, s), 3.89 (3H, s), 4.53 (2H, s), 6.66 (1H, d, J=8.8 Hz), 7.08 (1H, d, J=8.8 Hz), 7.24 (1H, s).

Compound (1a-12) of Present Invention
$^1$H-NMR (CDCl$_3$)δ: 2.37 (3H, s), 5.41 (2H, s), 7.16 (1H, s), 7.34-7.45 (5H, m).

Compound (1a-13) of Present Invention
$^1$H-NMR (CDCl$_3$)δ: 2.41 (3H, s), 4.02 (3H, s), 5.66 (2H, s), 7.21 (1H, s), 7.51-7.56 (3H, m), 7.65 (1H, d, J=8.5 Hz), 7.84-7.87 (1H, m), 8.11-8.15 (1H, m).

Compound (1a-14) of Present Invention
$^1$H-NMR (CDCl$_3$)δ: 2.39 (3H, s), 3.99 (3H, s), 5.43 (2H, s), 6.88-6.93 (1H, m), 7.16 (1H, s), 7.71 (1H, d, J=7.9 Hz), 8.1 (1H, d, J=5.2 Hz).

Compound (1a-15) of Present Invention
$^1$H-NMR (CDCl$_3$)δ: 2.32 (3H, s), 2.34 (3H, s), 2.39 (3H, s), 5.38 (2H, s), 7.04-7.10 (2H, m), 7.16 (1H, s), 7.21 (1H, s).

Compound (1a-16) of Present Invention
$^1$H-NMR (CDCl$_3$)δ: 2.39 (3H, s), 2.43 (3H, s), 5.60 (2H, d, J=1.6 Hz), 6.95 (1H, t, J=9.2 Hz), 7.07 (1H, d, J=7.2 Hz), 7.18 (1H, s), 7.23-7.28 (1H, m).

Compound (1a-17) of Present Invention
$^1$H-NMR (CDCl$_3$)δ: 2.29 (3H, d, J=1.8 Hz), 2.39 (3H, s), 5.42 (2H, s), 7.01-7.07 (1H, m), 7.14-7.21 (3H, m).

Compound (1a-18) of Present Invention
$^1$H-NMR (CDCl$_3$)δ: 2.33 (3H, s), 2.39 (3H, d, J=3.2 Hz), 5.37 (2H, s), 6.91-6.99 (1H, m), 7.11-7.18 (3H, m).

Compound (1a-19) of Present Invention
$^1$H-NMR (CDCl$_3$)δ: 2.38 (6H, m), 5.39 (2H, s), 6.92-6.98 (1H, m), 7.07 (1H, s), 7.10-7.20 (2H, m).

Compound (1a-20) of Present Invention
$^1$H-NMR (CDCl$_3$)δ: 2.27 (3H, s), 2.39 (3H, s), 5.34 (2H, s), 6.97 (1H, d, J=3.6 Hz), 7.16 (1H, s), 7.37 (1H, d, J=3.6 Hz).

Compound (1a-21) of Present Invention
$^1$H-NMR (CDCl$_3$)δ: 2.38 (3H, s), 3.96 (3H, s), 5.45 (2H, s), 6.98-7.04 (1H, m), 7.06-7.11 (1H, m), 7.15 (1H, s), 7.19 (1H, d, J=7.6 Hz).

Compound (1a-22) of Present Invention
$^1$H-NMR (CDCl$_3$)δ: 2.37 (3H, s), 3.82 (3H, s), 5.39 (2H, s), 6.64 (2H, m), 7.15 (1H, s), 7.38 (1H, t, J=7.6 Hz).

Compound (1a-23) of Present Invention
$^1$H-NMR (CDCl$_3$)δ: 2.38 (3H, s), 3.81 (3H, s), 5.43 (2H, s), 6.81 (1H, m), 6.98 (1H, m), 7.15 (2H, m).

Compound (1a-24) of Present Invention
$^1$H-NMR (CDCl$_3$)δ: 2.33 (3H, s), 3.76 (3H, s), 3.79 (3H, s), 5.43 (2H, s), 6.84 (2H, m), 6.99 (1H, s), 7.15 (1H, s).

Compound (1a-25) of Present Invention
$^1$H-NMR (CDCl$_3$)δ: 2.27 (3H, s), 2.33 (3H, s), 3.85 (3H, s), 4.88 (2H, s), 6.53 (1H, s), 6.80 (2H, m), 7.21 (1H, m).

Compound (1a-26) of Present Invention
$^1$H-NMR (CDCl$_3$)δ: 2.29 (3H, s), 2.38 (3H, s), 3.81 (3H, s), 5.41 (2H, s), 6.79 (1H, d, J=8.4 Hz), 7.11 (1H, d, J=8.4 Hz), 7.16 (1H, s), 7.21 (1H, s).

Compound (1a-27) of Present Invention
$^1$H-NMR (CDCl$_3$)δ: 2.36 (3H, s), 2.37 (3H, s), 3.82 (3H, s), 5.41 (1H, s), 5.44 (1H, s), 6.72 (1H, s), 6.77 (1H, d, J=7.6 Hz), 7.13-7.15 (1H, m), 7.27-7.31 (1H, m).

Compound (1a-28) of Present Invention
$^1$H-NMR (CDCl$_3$)δ: 2.31 (3H, s), 2.38 (3H, s), 3.78 (3H, s), 5.45 (2H, s), 7.06 (1H, t, J=7.6 Hz), 7.16 (1H, s), 7.19 (1H, d, J=7.6 Hz), 7.28 (1H, d, J=7.6 Hz).

Compound (1a-29) of Present Invention
$^1$H-NMR (CDCl$_3$)δ: 2.38 (3H, s), 3.90 (3H, s), 5.46 (2H, s), 7.09 (1H, t, J=7.6 Hz), 7.15 (1H, s), 7.37 (2H, m).

Compound (1a-30) of Present Invention
$^1$H-NMR (CDCl$_3$)δ: 2.38 (3H, s), 3.83 (3H, s), 5.43 (2H, s), 6.86 (1H, m), 6.94 (1H, d, J=7.6 Hz), 7.14 (1H, s), 7.33 (1H, d, J=8 Hz).

Compound (1a-31) of Present Invention
$^1$H-NMR (CDCl$_3$)δ: 2.39 (3H, s), 3.83 (3H, s), 5.41 (2H, s), 6.81 (1H, d, J=8.8 Hz), 7.15 (1H, s), 7.25 (1H, s), 7.39 (1H, d, J=2.8 Hz).

Compound (1a-32) of Present Invention
¹H-NMR (CDCl₃)δ: 1.37 (3H, t, J=7.2 Hz), 2.38 (3H, s), 4.05 (2H, q, J=7.2 Hz), 5.47 (2H, s), 6.88 (1H, d, J=8.0 Hz), 6.96 (1H, t, J=7.6 Hz), 7.16 (1H, s), 7.31 (1H, t, J=7.6 Hz), 7.40 (1H, d, J=7.2 Hz).

Compound (1a-33) of Present Invention
¹H-NMR (CDCl₃)δ: 1.02 (3H, t, J=7.2 Hz), 1.78 (2H, m), 2.38 (3H, s), 3.97 (2H, t, J=6.4 Hz), 5.47 (2H, s), 6.88 (1H, d, J=8.0 Hz), 6.96 (1H, t, J=7.6 Hz), 7.16 (1H, s), 7.32 (1H, t, J=7.6 Hz), 7.39 (1H, d, J=7.6 Hz).

Compound (1a-34) of Present Invention
¹H-NMR (CDCl₃)δ: 1.29 (6H, m), 2.38 (3H, s), 4.60 (1H, m), 5.44 (2H, s), 6.91 (2H, m), 7.16 (1H, s), 7.28 (1H, m), 7.40 (1H, d, J=6.8 Hz).

Compound (1a-35) of Present Invention
¹H-NMR (CDCl₃)δ: 2.38 (3H, s), 5.36 (1H, d, J=10.8 Hz), 5.47 (2H, s), 5.70 (1H, d, J=17.2 Hz), 6.98 (1H, m), 7.15 (1H, s), 7.30 (1H, t, J=7.6 Hz), 7.37 (1H, t, J=7.2 Hz), 7.42 (1H, d, J=7.2 Hz), 7.56 (1H, d, J=7.6 Hz).

Compound (1a-36) of Present Invention
¹H-NMR (CDCl₃)δ: 2.38 (3H, s), 5.49 (2H, s), 7.15 (1H, s), 7.30 (2H, m), 7.39 (1H, m), 7.55 (1H, d, J=7.6 Hz).

Compound (1a-37) of Present Invention
¹H-NMR (CDCl₃)δ: 2.38 (3H, s), 5.41 (2H, s), 7.15 (2H, m), 7.34 (1H, t, J=4.8 Hz), 7.38 (1H, s).

Compound (1a-38) of Present Invention
¹H-NMR (CDCl₃)δ: 2.37 (3H, s), 2.49 (3H, s), 5.33 (2H, s), 7.03 (1H, d, J=5.2 Hz), 7.06 (1H, d, J=5.2 Hz), 7.14 (1H, s).

Compound (1a-39) of Present Invention
¹H-NMR (CDCl₃)δ: 2.37 (3H, s), 3.83 (3H, s), 5.29 (2H, s), 6.23 (1H, d, J=3.2 Hz), 7.14 (1H, s), 7.33 (1H, d, J=3.6 Hz).

Compound (1a-40) of Present Invention
¹H-NMR (CDCl₃)δ: 1.26 (3H, t, J=7.2 Hz), 2.32 (3H, s), 2.71 (2H, q, J=7.2 Hz), 5.38 (2H, s), 6.92-6.98 (1H, m), 7.09-7.26 (3H, m).

Compound (1a-41) of Present Invention
¹H-NMR (CDCl₃)δ: 1.27 (3H, t, J=7.2 Hz), 2.43 (3H, s), 2.70 (2H, q, J=7.2 Hz), 5.50 (2H, d, J=1.6 Hz), 6.95 (1H, t, J=9.2 Hz), 7.07 (1H, d, J=7.2 Hz), 7.18 (1H, s), 7.23-7.28 (1H, m).

Compound (1a-42) of Present Invention
¹H-NMR (CDCl₃)δ: 1.27 (3H, t, J=7.2 Hz), 2.39 (3H, s), 2.70 (2H, q, J=7.2 Hz), 5.38 (2H, s), 6.86-6.96 (2H, m), 7.17 (1H, s), 7.34-7.38 (1H, m).

Compound (1a-43) of Present Invention
¹H-NMR (CDCl₃)δ: 2.32 (3H, s), 2.36 (3H, s), 2.38 (3H, s), 5.38 (2H, s), 7.03-7.05 (2H, m), 7.17 (1H, s), 7.24-7.29 (1H, m).

Compound (1a-44) of Present Invention
¹H-NMR (CDCl₃)δ: 2.38 (3H, s), 5.40 (2H, s), 7.01-7.05 (1H, m), 7.13 (1H, s), 7.15 (1H. s), 7.18 (1H, d, J=7.64 Hz), 7.31-7.36 (1H, m).

Compound (1a-45) of Present Invention
¹H-NMR (CDCl₃)δ: 2.37 (3H, s), 5.36 (2H, s), 7.06 (2H, t, J=8.6 Hz), 7.13 (1H, s), 7.39-7.42 (2H, m).

Compound (1a-46) of Present Invention
¹H-NMR (CDCl₃)δ: 2.38 (3H, s), 5.60 (2H, s), 7.14 (1H, s), 7.43-7.47 (1H, m), 7.59-7.62 (2H.m), 7.70 (1H, d, J=7.6 Hz).

Compound (1a-47) of Present Invention
¹H-NMR (CDCl₃)δ: 2.36 (3H, s), 5.51 (2H, s), 6.89 (1H, d, J=8.2 Hz), 6.96 (2H, d, J=8.04 Hz), 7.06-7.15 (3H, m), 7.27-7.33 (3H, m), 7.53 (1H, d, J=7.48 Hz).

Compound (1a-48) of Present Invention
¹H-NMR (CDCl₃)δ: 2.39 (3H, s), 5.60 (2H, s), 7.15 (1H, s), 7.45 (1H, t, J=7.56 Hz), 7.57 (1H, t, J=7.6 Hz), 7.65-7.70 (2H. m).

Compound (1a-49) of Present Invention
¹H-NMR (CDCl₃)δ: 2.30 (3H, s), 2.66 (6H, s), 4.94 (2H, s), 6.62 (1H, s), 7.04-7.07 (1H, m), 7.14-7.17 (2H, m), 7.28-7.29 (1H. m).

Compound (1a-50) of Present Invention
¹H-NMR (CDCl₃)δ: 2.30 (3H, s), 2.48 (3H, s), 5.50 (2H, s), 7.16 (1H, s), 7.19-7.20 (1H, m), 7.32-7.34 (2H, m), 7.43 (1H, t, J=7.6 Hz).

Compound (1a-51) of Present Invention
¹H-NMR (CDCl₃)δ: 0.96 (3H, t, J=8 Hz), 1.58-1.68 (2H, m), 2.38 (3H, s), 2.66 (2H, t, J=7.92 Hz), 5.43 (2H, s), 7.16 (1H, s), 7.19-7.25 (2H, m), 7.30 (1H, t, J=6.56 Hz), 7.40 (1H, d, J=7.52 Hz).

Compound (1a-52) of Present Invention
¹H-NMR (CDCl₃)δ: 1.25 (6H, d, J=6.8 Hz), 2.38 (3H, s), 3.16-3.22 (1H, m), 5.46 (2H, s), 7.16 (1H, s), 7.18-7.23 (1H, m), 7.35-7.39 (3H, m).

Compound (1a-53) of Present Invention
¹H-NMR (CDCl₃)δ: 1.42 (9H, s), 2.39 (3H, s), 5.64 (2H, s), 7.16 (1H, s), 7.25-7.26 (1H, m), 7.28-7.32 (1H, m), 7.44-7.47 (2H, m).

Compound (1a-54) of Present Invention
¹H-NMR (CDCl₃)δ: 2.38 (3H, s), 5.48 (2H, s), 7.06-7.25 (4H, m).

Compound (1a-55) of Present Invention
¹H-NMR (CDCl₃)δ: 2.38 (3H, s), 5.42 (2H, s), 6.81-6.91 (2H, m), 7.14 (1H, s), 7.43-7.49 (1H, m).

Compound (1a-56) of Present Invention
¹H-NMR (CDCl₃)δ: 2.38 (3H, s), 5.45 (2H, s), 6.99-7.07 (2H, m), 7.14 (1H, s), 7.17-7.21 (1H, m).

Compound (1a-57) of Present Invention
¹H-NMR (CDCl₃)δ: 2.38 (3H, s), 5.49 (2H, s), 6.90-6.96 (2H, m), 7.16 (1H, s), 7.31-7.38 (1H, m).

Compound (1a-58) of Present Invention
¹H-NMR (CDCl₃)δ: 2.38 (3H, s), 2.64 (3H, s), 5.42 (2H, s), 7.14-7.16 (2H, m), 7.69 (1H, d, J=7.6 Hz), 8.47 (1H, d, J=4.4 Hz).

Compound (1a-59) of Present Invention
¹H-NMR (CDCl₃) δ value: 2.38 (3H, s), 2.41 (3H, s), 5.54 (2H, s), 7.15 (1H, s), 7.18-7.21 (1H, m), 7.51 (1H, d, J=7.64 Hz), 8.45 (1H, d, J=4.60 Hz).

Compound (1a-60) of Present Invention
¹H-NMR (CDCl₃)δ: 2.38 (3H, s), 2.40 (3H, s), 5.44 (2H, s), 7.13 (1H, s), 7.14-7.21 (1H, m), 8.46 (1H, d, J=4.96 Hz), 8.57 (1H, s).

Compound (1a-61) of Present Invention
¹H-NMR (CDCl₃)δ: 2.33 (3H, s), 2.39 (3H, s), 5.42 (2H, s), 7.13 (1H, s), 7.32 (1H, d, J=4.8 Hz), 8.43 (1H, s), 8.47 (1H, d, J=4.8 Hz).

Compound (1a-63) of Present Invention
¹H-NMR (CDCl₃)δ: 2.38 (3H, s), 4.36-4.42 (2H, m), 5.48 (2H, s), 6.88 (1H, d, J=8.24 Hz), 7.07 (1H, t, J=7.52 Hz), 7.15 (1H, s), 7.32-7.36 (1H, m), 7.46 (1H, d, J=7.36 Hz).

Compound (1a-64) of Present Invention
¹H-NMR (CDCl₃)δ: 2.38 (3H, s), 5.38 (2H, s), 7.13 (1H, s), 7.29-7.32 (3H, m), 7.42 (1H, s).

Compound (1a-65) of Present Invention
¹H-NMR (CDCl₃)δ: 2.37 (3H, s), 5.37 (2H, s), 7.12 (1H, s), 7.33-7.37 (4H, m).

Compound (1a-66) of Present Invention
¹H-NMR (CDCl₃)δ: 2.38 (3H, s), 3.38 (3H, s), 4.55 (2H, s), 5.49 (2H, s), 7.15 (1H, s), 7.30-7.37 (2H, m), 7.39-7.41 (1H, m), 7.45-7.47 (1H, m).

Compound (1a-67) of Present Invention
¹H-NMR (CDCl₃)δ: 2.39 (3H, s), 5.50 (2H, s), 7.16 (1H, s), 7.19-7.23 (1H, m), 7.34 (1H, t, J=7.46 Hz), 7.50 (1H, d, J=7.04 Hz), 7.59 (1H, d, J=7.96 Hz).

Compound (1a-68) of Present Invention
¹H-NMR (CDCl₃)δ: 2.37 (3H, s), 5.31 (2H, s), 7.08 (1H, s), 7.32-7.41 (8H, m), 7.57-7.60 (1H, m).

Compound (1a-69) of Present Invention
¹H-NMR (CDCl₃)δ: 2.37 (3H, s), 3.52-3.61 (2H, m), 5.50 (2H, s), 7.13-7.14 (1H, m), 7.32-7.38 (2H, m), 7.47-7.52 (2H, m).

Compound (1a-70) of Present Invention
¹H-NMR (CDCl₃)δ: 2.39 (3H, s), 5.53 (2H, s), 7.14 (1H, s), 7.21-7.23 (1H, m), 7.41-7.46 (2H, m).

Compound (1a-71) of Present Invention
¹H-NMR (CDCl₃)δ: 2.38 (3H, s), 5.47 (2H, s), 7.14 (1H, s), 7.27-7.28 (1H, m), 7.42-7.46 (2H, m).

Compound (1a-72) of Present Invention
¹H-NMR (CDCl₃)δ: 2.39 (3H, s), 5.48 (2H, s), 7.14 (1H, s), 7.26-7.27 (1H, m), 7.32 (1H, d, J=8.48 Hz), 7.50-7.53 (1H, m).

Compound (1a-73) of Present Invention
¹H-NMR (CDCl₃)δ: 2.39 (3H, s), 5.67 (2H, s), 7.18 (1H, s), 7.25-7.28 (1H, m), 7.35 (1H, s), 7.37 (1H, s).

Compound (1a-74) of Present Invention
¹H-NMR (CDCl₃)δ: 2.39 (3H, s), 5.67 (2H, s), 6.37-6.38 (1H, m), 6.49 (1H, d, J=3.2 Hz), 7.14 (1H, s), 7.45 (1H, s).

Compound (1a-75) of Present Invention
¹H-NMR (CDCl₃)δ: 2.37 (3H, s), 5.28 (2H, s), 6.42 (1H, s), 7.13 (1H, s), 7.41 (1H, d, J=1.4 Hz), 7.53 (1H, s).

Compound (1a-76) of Present Invention
¹H-NMR (CDCl₃)δ: 2.35 (3H, s), 2.37 (3H, s), 5.21 (2H, s), 6.40 (1H, d, J=1.56 Hz), 7.13 (1H, s), 7.25-7.26 (1H, m).

Compound (1a-77) of Present Invention
¹H-NMR (CDCl₃)δ: 2.27 (3H, s), 2.30 (3H, s), 2.38 (3H, s), 5.42 (2H, s), 7.11 (1H, t, J=7.48 Hz), 7.15 (2H, m), 7.16-7.23 (1H, m).

Compound (1a-78) of Present Invention
¹H-NMR (CDCl₃)δ: 2.38 (3H, s), 2.41 (6H, s), 5.48 (2H, s), 7.05 (2H, t, J=7.52 Hz), 7.15-7.19 (2H, m).

Compound (1a-79) of Present Invention
¹H-NMR (CDCl₃)δ: 2.39 (3H, s), 2.41 (3H, s), 5.42 (2H, s), 7.11-7.15 (2H, m), 7.30 (1H, d, J=7.44 Hz), 7.37 (1H, d, J=7.76 Hz).

Compound (1a-80) of Present Invention
¹H-NMR (CDCl₃)δ: 2.36 (3H, s), 2.38 (3H, s), 5.37 (2H, s), 7.13 (1H, s), 7.16-7.20 (2H, m), 7.32 (1H, d, J=8.08 Hz).

Compound (1a-81) of Present Invention
¹H-NMR (CDCl₃)δ: 2.39 (3H, s), 2.43 (3H, s), 5.59 (2H, s), 7.12 (1H, d, J=7.48 Hz), 7.17-7.22 (2H, m), 7.27 (1H, d, J=7.92 Hz).

Compound (1a-82) of Present Invention
¹H-NMR (CDCl₃)δ: 2.32 (3H, s), 2.38 (3H, s), 5.36 (2H, s), 7.11-7.14 (2H, m), 7.21-7.22 (1H, m), 7.39 (1H, d, J=1.56 Hz).

Compound (1a-83) of Present Invention
¹H-NMR (CDCl₃)δ: 2.24 (3H, s), 2.38 (3H, s), 3.83 (3H, s), 5.42 (2H, s), 6.87 (1H, d, J=8.82 Hz), 7.01 (1H, d, J=7.56 Hz), 7.15-7.20 (2H, m).

Compound (1a-84) of Present Invention
¹H-NMR (CDCl₃)δ: 2.24 (3H, s), 2.29 (3H, s), 3.79 (3H, s), 4.75 (2H, s), 6.41 (1H, s), 6.72-6.75 (2H, m), 7.10 (1H, d, J=8.0 Hz).

Compound (1a-85) of Present Invention
¹H-NMR (CDCl₃)δ: 2.39 (3H, s), 2.43 (3H, s), 5.44 (2H, s), 7.15 (1H, s), 7.31 (1H, d, J=7.88 Hz), 7.51 (1H, d, J=7.8 Hz), 7.66 (1H, s).

Compound (1a-86) of Present Invention
¹H-NMR (CDCl₃)δ: 2.30 (3H, s), 2.38 (3H, s), 3.79 (3H, s), 5.37 (2H, s), 6.79-6.82 (1H, m), 6.95 (1H, d, J=2.8 Hz), 7.11 (1H, d, J=8.5 Hz), 7.15 (1H, s).

Compound (1a-87) of Present Invention
¹H-NMR (CDCl₃)δ: 1.65 (3H, d, J=6.5 Hz), 2.34 (3H, s), 2.40 (3H, s), 6.18 (1H, q, J=6.5 Hz), 7.08 (1H, s), 7.14-7.23 (3H, m), 7.44-7.46 (1H, m).

Compound (1a-88) of Present Invention
¹H-NMR (CDCl₃)δ: 0.98 (3H, t, J=7.2 Hz), 1.87-1.92 (1H, m), 2.00-2.05 (1H, m), 2.32 (3H, s), 2.42 (3H, s), 5.95 (1H, t, J=7.2 Hz), 7.04 (1H, s), 7.12-7.18 (3H, m), 7.37-7.40 (1H, m).

Compound (1a-89) of Present Invention
¹H-NMR (CDCl₃)δ: 0.94 (3H, t, J=7.36 Hz), 1.35-1.43 (1H, m), 1.47-1.56 (1H, m), 1.73-1.82 (1H, m), 1.96-2.05 (1H, m), 2.32 (3H, s), 2.42 (3H, s), 6.00-6.03 (1H, m), 7.04 (1H, s), 7.12-7.20 (3H, m), 7.38-7.40 (1H, m).

Compound (1a-90) of Present Invention
¹H-NMR (CDCl₃)δ: 0.86 (3H, t, J=6.88 Hz), 1.09 (3H, t, J=6.64 Hz), 2.03-2.21 (1H, m), 2.31 (3H, s), 2.44 (3H, s), 5.73 (1H, d, J=7.64 Hz), 7.02 (1H, s), 7.11-7.18 (3H, m), 7.33-7.36 (1H, m).

Compound (1a-91) of Present Invention
¹H-NMR (CDCl₃)δ: 0.32-0.37 (1H, m), 0.67-0.77 (3H, m), 1.39-1.50 (1H, m), 2.18 (3H, s), 2.28 (3H, s), 4.88 (1H, d, J=9.28 Hz), 6.51 (1H, s), 7.16-7.22 (1H, m), 7.23-7.28 (2H, m), 7.62 (1H, t, J=6.2 Hz).

Compound (1a-202) of Present Invention
¹H-NMR (CDCl₃)δ: 1.27 (6H, m), 2.75 (4H, m), 5.44 (2H, s), 7.18 (1H, s), 7.23 (3H, m), 7.40 (1H, m).

Compound (1a-203) of Present Invention
¹H-NMR (CDCl₃)δ: 1.24 (3H, t, J=7.5 Hz), 2.38 (3H, s), 2.73 (2H, q, J=7.5 Hz), 5.45 (2H, s), 7.17 (1H, s), 7.25 (3H, m), 7.39 (1H, m).

Compound (1a-204) of Present Invention
¹H-NMR (CDCl₃)δ: 1.76 (3H, d, J=6.6 Hz), 2.36 (3H, s), 6.16 (1H, q, J=6.6 Hz), 7.09 (1H, s), 7.45-7.49 (2H, m), 7.51-7.55 (1H, m), 7.80-7.89 (4H, m).

Compound (1b-2) of Present Invention
¹H-NMR (CDCl₃)δ: 2.40 (3H, s), 2.92 (3H, s), 5.51 (2H, s), 7.20-7.26 (2H, m), 7.28-7.33 (1H, m), 7.39-7.42 (1H, m), 7.55 (1H, s).

Compound (1c-2) of Present Invention
¹H-NMR (CDCl₃)δ: 2.40 (3H, s), 3.17 (3H, s), 5.54 (2H, s), 6.91-7.03 (2H, m), 7.32-7.40 (2H, m), 7.72 (1H, s).

Compound (1b-12) of Present Invention
¹H-NMR (CDCl₃)δ: 2.39 (3H, s), 5.50 (2H, s), 7.37-7.47 (5H, m), 7.53 (1H, s).

Compound (1c-12) of Present Invention
¹H-NMR (CDCl₃)δ: 3.17 (3H, s), 5.54 (2H, s), 6.91-7.03 (2H, m), 7.32-7.40 (3H, m), 7.72 (1H, s).

Next, reference production examples for producing of production intermediates are described.

Reference Production Example 1

In a nitrogen atmosphere, a tetrahydrofuran solution (10 ml) of 829 mg (6 mmol) of 2-methoxybenzyl alcohol was added dropwise to a tetrahydrofuran suspension (20 ml) of 280 mg (7 mmol) of 60% sodium hydride at 0° C., and the mixture was stirred at room temperature for 30 minutes. A tetrahydrofuran solution (10 ml) of 1.21 g (5 mmol) of 2,5-dibromothiazole was added to the reaction mixture at room temperature, and the resulting product was stirred for 4 hours. The reaction mixture was cooled to 0° C., then, water was added thereto, and the resulting product was extracted three times with ethyl acetate. After the organic layers were combined and concentrated, the residue was purified by silica gel column chromatography, whereby 1.05 g of 5-bromo-2-(2-methoxybenzyloxy)thiazole (compound (4-1)) was obtained.

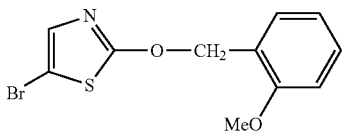 [SMILES: COc1ccccc1COc1ncc(Br)s1]

$^1$H-NMR (CDCl$_3$)δ: 3.86 (3H, s), 5.49 (2H, s), 6.90 (1H, d, J=8.3 Hz), 6.93 (1H, dt, J=1.5, 7.5 Hz), 7.07 (1H, s), 7.33 (1H, dt, J=1.5, 7.5 Hz), 7.43 (1H, dd, J=1.5, 7.5 Hz).

The reaction of the following formula was performed in the same manner as in Reference Production Example 1 except that a compound (10) was used instead of 2,5-dibromothiazole and a compound (3) was used instead of 2-methoxybenzyl alcohol, whereby compounds (4-2) to (4-86) represented by Formula (4) were obtained.

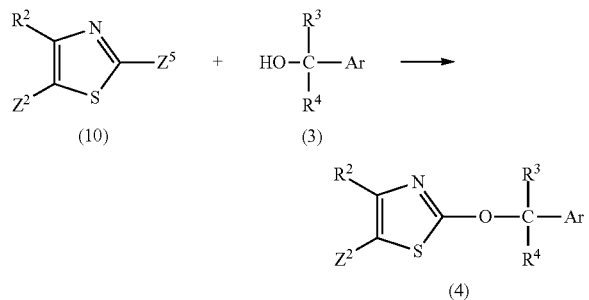

R$^2$, R$^3$, R$^4$, Ar, Z$^2$, and Z$^5$ in the formula represent the combinations described in [Table 7] to [Table 10] below.

TABLE 7

| Compound | R$^2$ | R$^3$ | R$^4$ | Ar | Z$^2$ | Z$^5$ |
|---|---|---|---|---|---|---|
| 4-2 | H | H | H | 2-Me—Ph | Br | Br |
| 4-3 | H | H | H | 2-Cl—Ph | Br | Br |
| 4-4 | H | H | H | 2-F—Ph | Br | Br |
| 4-5 | H | H | H | 2-F-6-OMe—Ph | Br | Br |
| 4-6 | Me | H | H | 2-OMe—Ph | Br | Br |
| 4-7 | H | H | H | 3-Py | Br | Br |
| 4-8 | H | H | H | 2,4,6-Me$_3$—Ph | Br | Br |
| 4-9 | H | H | H | 2,3,4-(OMe)$_3$—Ph | Br | Br |
| 4-10 | H | H | H | Ph | Br | Br |
| 4-11 | H | H | H | 1-OMe-2-Nap | Br | Br |
| 4-12 | H | H | H | 2-OMe-3-Py | Br | Br |
| 4-13 | H | H | H | 2,5-Me$_2$—Ph | Br | Br |
| 4-14 | H | H | H | 2-F-6-Me—Ph | Br | Br |
| 4-15 | H | H | H | 3-F-2-Me—Ph | Br | Br |
| 4-16 | H | H | H | 4-F-2-Me—Ph | Br | Br |
| 4-17 | H | H | H | 5-F-2-Me—Ph | Br | Br |
| 4-18 | H | H | H | 4-Me-3-Thie | Br | Br |
| 4-19 | H | H | H | 3-F-2-OMe—Ph | Br | Br |
| 4-20 | H | H | H | 4-F-2-OMe—Ph | Br | Br |
| 4-21 | H | H | H | 5-F-2-OMe—Ph | Br | Br |
| 4-22 | H | H | H | 2,5-(OMe)$_2$—Ph | Br | Br |
| 4-23 | H | H | H | 2-OMe-6-Me—Ph | Br | Br |
| 4-24 | H | H | H | 2-OMe-5-Me—Ph | Br | Br |
| 4-25 | H | H | H | 2-OMe-4-Me—Ph | Br | Br |

TABLE 8

| Compound | R$^2$ | R$^3$ | R$^4$ | Ar | Z$^2$ | Z$^5$ |
|---|---|---|---|---|---|---|
| 4-26 | H | H | H | 2-OMe-3-Me—Ph | Br | Br |
| 4-27 | H | H | H | 3-Cl-2-OMe—Ph | Br | Br |
| 4-28 | H | H | H | 4-Cl-2-OMe—Ph | Br | Br |
| 4-29 | H | H | H | 5-Cl-2-OMe—Ph | Br | Br |
| 4-30 | H | H | H | 2-OEt—Ph | Br | Br |
| 4-31 | H | H | H | 2-OPr—Ph | Br | Br |
| 4-32 | H | H | H | 2-Oi—Pr—Ph | Br | Br |
| 4-33 | H | H | H | 2-CH$_2$=CH—Ph | Br | Br |
| 4-34 | H | H | H | 2-OCF$_3$—Ph | Br | Br |
| 4-35 | H | H | H | 3-Thie | Br | Br |
| 4-36 | H | H | H | 2-Me-3-Thie | Br | Br |
| 4-37 | H | H | H | 4-OMe-3-Thie | Br | Br |
| 4-38 | H | H | H | 2,4-Me$_2$—Ph | Br | Br |
| 4-39 | H | H | H | 3-F—Ph | Br | Br |
| 4-40 | H | H | H | 4-F—Ph | Br | Br |
| 4-41 | H | H | H | 2-CN—Ph | Br | Br |
| 4-42 | H | H | H | 2-OPh—Ph | Br | Br |
| 4-43 | H | H | H | 2-CF$_3$—Ph | Br | Br |
| 4-44 | H | H | H | 2-NMe$_2$—Ph | Br | Br |
| 4-45 | H | H | H | 2-SMe—Ph | Br | Br |
| 4-46 | H | H | H | 2-Pr—Ph | Br | Br |
| 4-47 | H | H | H | 2-i-Pr—Ph | Br | Br |
| 4-48 | H | H | H | 2-t-Bu—Ph | Br | Br |
| 4-49 | H | H | H | 2,3-F$_2$—Ph | Br | Br |
| 4-50 | H | H | H | 2,4-F$_2$—Ph | Br | Br |

TABLE 9

| Compound | R$^2$ | R$^3$ | R$^4$ | Ar | Z$^2$ | Z$^5$ |
|---|---|---|---|---|---|---|
| 4-51 | H | H | H | 2,5-F$_2$—Ph | Br | Br |
| 4-52 | H | H | H | 2,6-F$_2$—Ph | Br | Br |
| 4-53 | H | H | H | 2-Me-3-Py | Br | Br |
| 4-54 | H | H | H | 3-Me-2-Py | Br | Br |
| 4-55 | H | H | H | 4-Me-3-Py | Br | Br |
| 4-56 | H | H | H | 3-Me-4-Py | Br | Br |
| 4-57 | H | H | H | 1-Me-3-Pyrr | Br | Br |
| 4-58 | H | H | H | 2-OCH$_2$CF$_3$—Ph | Br | Br |
| 4-59 | H | H | H | 3-Cl—Ph | Br | Br |
| 4-60 | H | H | H | 4-Cl—Ph | Br | Br |
| 4-61 | H | H | H | 2-CH$_2$OMe—Ph | Br | Br |
| 4-62 | H | H | H | 2-Br—Ph | Br | Br |
| 4-63 | H | H | H | 2-Ph—Ph | Br | Br |
| 4-64 | H | H | H | 2-CH$_2$CF$_3$—Ph | Br | Br |
| 4-65 | H | H | H | 2,3-Cl$_2$—Ph | Br | Br |
| 4-66 | H | H | H | 2,4-Cl$_2$—Ph | Br | Br |
| 4-67 | H | H | H | 2,5-Cl$_2$—Ph | Br | Br |
| 4-68 | H | H | H | 2,6-Cl$_2$—Ph | Br | Br |
| 4-69 | H | H | H | 2-Fur | Br | Br |
| 4-70 | H | H | H | 3-Fur | Br | Br |
| 4-71 | H | H | H | 2-Me-3-Fur | Br | Br |
| 4-72 | H | H | H | 2,6-Me$_2$—Ph | Br | Br |
| 4-73 | H | H | H | 2,3-Me$_2$—Ph | Br | Br |
| 4-74 | H | H | H | 3-Cl-2-Me—Ph | Br | Br |
| 4-75 | H | H | H | 4-Cl-2-Me—Ph | Br | Br |

TABLE 10

| Compound | R$^2$ | R$^3$ | R$^4$ | Ar | Z$^2$ | Z$^5$ |
|---|---|---|---|---|---|---|
| 4-76 | H | H | H | 2-Cl-6-Me—Ph | Br | Br |
| 4-77 | H | H | H | 5-Cl-2-Me—Ph | Br | Br |
| 4-78 | H | H | H | 3-OMe-2-Me—Ph | Br | Br |
| 4-79 | H | H | H | 4-OMe-2-Me—Ph | Br | Br |
| 4-80 | H | H | H | 2-Me-5-CF$_3$—Ph | Br | Br |
| 4-81 | H | H | H | 5-OMe-2-Me—Ph | Br | Br |
| 4-82 | H | Me | H | 2-Me—Ph | Br | Br |
| 4-83 | H | Et | H | 2-Me—Ph | Br | Br |
| 4-84 | H | Pr | H | 2-Me—Ph | Br | Br |
| 4-85 | H | i-Pr | H | 2-Me—Ph | Br | Br |
| 4-86 | H | c-Pr | H | 2-Me—Ph | Br | Br |

The ¹H-NMR data of each of the compounds (4-2) to (4-86) are described below. The compound (4-9), (4-11), (4-12), (4-18), and (4-38) were subjected to the next reaction without performing ¹H-NMR measurement.

Compound (4-2)
¹H-NMR (CDCl$_3$)δ: 2.38 (3H, s), 5.41 (2H, s), 7.07 (1H, s) 7.16-7.28 (3H, m), 7.37-7.42 (1H, m).

Compound (4-3)
¹H-NMR (CDCl$_3$)δ: 5.52 (2H, s), 7.08 (1H, s) 7.27-7.37 (2H, m), 7.38-7.42 (1H, m), 7.47-7.52 (1H, m).

Compound (4-4)
¹H-NMR (CDCl$_3$)δ: 5.48 (2H, s), 7.07 (1H, s), 7.09-7.18 (2H, m), 7.08-7.18 (1H, m), 7.43-7.57 (1H, m).

Compound (4-5)
¹H-NMR (CDCl$_3$)δ: 3.86 (3H, s), 5.48 (2H, s), 6.69-6.76 (2H, m), 7.09 (1H, s), 7.29-7.36 (1H, m).

Compound (4-6)
¹H-NMR (CDCl$_3$)δ: 2.61 (3H, s), 3.85 (3H, s), 5.42 (2H, s), 6.91 (1H, d, J=8.3 Hz), 6.97 (1H, dt, J=1.5, 7.5 Hz), 7.34 (1H, dt, J=1.5, 7.5 Hz,), 7.42 (1H, dd, J=1.5, 7.5 Hz).

Compound (4-7)
¹H-NMR (CDCl$_3$)δ: 5.45 (2H, s), 7.08 (1H, s), 7.37 (1H, m), 7.79 (1H, m), 8.62 (1H, m), 8.70 (1H, m).

Compound (4-8)
¹H-NMR (CDCl$_3$)δ: 2.28 (3H, s), 2.37 (6H, s), 5.45 (2H, s), 6.91 (2H, s), 7.09 (1H, s).

Compound (4-10)
¹H-NMR (CDCl$_3$)δ: 5.40 (2H, s), 7.07 (1H, s), 7.34-7.45 (5H, m).

Compound (4-13)
¹H-NMR (CDCl$_3$)δ: 2.32 (3H, s), 2.33 (3H, s), 5.38 (2H, s), 7.07 (1H, s), 7.08-7.10 (2H, m), 7.19 (1H, s).

Compound (4-14)
¹H-NMR (CDCl$_3$)δ: 2.43 (3H, s), 5.50 (2H, d, J=1.6 Hz), 6.95 (1H, t, J=9.2 Hz), 7.07 (1H, d, J=7.2 Hz), 7.09 (1H, s), 7.23-7.30 (1H, m).

Compound (4-15)
¹H-NMR (CDCl$_3$)δ: 2.28 (3H, d, J=1.8 Hz), 5.42 (2H, s), 7.01-7.07 (1H, m), 7.08 (1H, s), 7.15-7.23 (2H, m).

Compound (4-16)
¹H-NMR (CDCl$_3$)δ: 2.38 (3H, s), 5.36 (2H, s), 6.87-6.96 (2H, m), 7.07 (1H, s), 7.11-7.18 (1H, m).

Compound (4-17)
¹H-NMR (CDCl$_3$)δ: 2.32 (3H, s), 5.39 (2H, s), 6.92-6.98 (1H, m), 7.07 (1H, s), 7.10-7.20 (2H, m).

Compound (4-19)
¹H-NMR (CDCl$_3$)δ: 3.96 (3H, s), 5.44 (2H, s), 6.98-7.04 (1H, m), 7.07 (1H, s), 7.08-7.12 (1H, m), 7.18 (1H, d, J=7.6 Hz).

Compound (4-20)
¹H-NMR (CDCl$_3$)δ: 3.87 (3H, s), 5.39 (2H, s), 6.64 (2H, m), 7.06 (1H, s), 7.35 (1H, t, J=6.8 Hz).

Compound (4-21)
¹H-NMR (CDCl$_3$)δ: 3.81 (3H, s), 5.42 (2H, s), 6.81 (1H, m), 6.98 (1H, m), 7.06 (1H, s), 7.14 (1H, m).

Compound (4-22)
¹H-NMR (CDCl$_3$)δ: 3.76 (3H, s), 3.79 (3H, s), 5.42 (2H, s), 6.84 (2H, m), 6.98 (1H, d, J=2.0 Hz), 7.06 (1H, s).

Compound (4-23)
¹H-NMR (CDCl$_3$)δ: 2.37 (3H, s), 3.81 (3H, s), 5.51 (2H, s), 6.77 (1H, d, J=8.4 Hz), 6.83 (1H, d, J=7.6 Hz), 7.09 (1H, s), 7.24 (1H, m).

Compound (4-24)
¹H-NMR (CDCl$_3$)δ: 2.29 (3H, s), 3.81 (3H, s), 5.41 (2H, s), 6.80 (1H, d, J=8.4 Hz), 7.07 (1H, d, J=8 Hz), 7.20 (1H, s).

Compound (4-25)
¹H-NMR (CDCl$_3$)δ: 2.26 (3H, s), 3.82 (3H, s), 5.41 (2H, s), 6.80 (1H, d, J=8.4 Hz), 7.07 (1H, s), 7.12 (1H, d, J=8.0 Hz), 7.20 (1H, s).

Compound (4-26)
¹H-NMR (CDCl$_3$)δ: 2.31 (3H, s), 3.78 (3H, s), 5.45 (2H, s), 7.05 (2H, m), 7.20 (1H, d, J=7.2 Hz), 7.26 (1H, m).

Compound (4-27)
¹H-NMR (CDCl$_3$)δ: 3.90 (3H, s), 5.46 (2H, s), 7.07 (2H, m), 7.37 (2H, m).

Compound (4-28)
¹H-NMR (CDCl$_3$)δ: 3.83 (3H, s), 5.39 (2H, s), 6.88 (1H, m), 6.94 (1H, m), 7.05 (1H, s), 7.31 (1H, d, J=8.4 Hz).

Compound (4-29)
¹H-NMR (CDCl$_3$)δ: 3.82 (3H, s), 5.41 (2H, s), 6.81 (1H, d, J=8.8 Hz), 7.06 (1H, s), 7.27 (1H, m), 7.37 (1H, m).

Compound (4-30)
¹H-NMR (CDCl$_3$)δ: 1.42 (3H, t, J=7.2 Hz), 4.06 (2H, q, J=7.2 Hz), 5.46 (2H, s), 6.88 (1H, d, J=8.0 Hz), 6.94 (1H, t, J=7.2 Hz), 7.07 (1H, s), 7.30 (1H, m), 7.38 (1H, m).

Compound (4-31)
¹H-NMR (CDCl$_3$)δ: 1.01 (3H, t, J=7.2 Hz), 1.80 (2H, m), 3.95 (2H, t, J=7.2 Hz), 5.46 (2H, s), 6.88 (1H, d, J=8.0 Hz), 6.94 (1H, t, J=7.6 Hz), 7.07 (1H, s), 7.30 (1H, m), 7.38 (1H, m).

Compound (4-32)
¹H-NMR (CDCl$_3$)δ: 1.32 (6H, m), 4.58 (1H, m), 5.44 (2H, s), 6.92 (2H, m), 7.07 (1H, s), 7.29 (1H, m), 7.38 (1H, m).

Compound (4-33)
¹H-NMR (CDCl$_3$)δ: 5.35 (1H, d, J=11 Hz), 5.46 (2H, s), 5.69 (1H, d, J=16 Hz), 6.97 (1H, m), 7.07 (1H, s), 7.28 (1H, m), 7.36 (1H, t, J=7.2 Hz), 7.41 (1H, d, J=7.6 Hz), 7.55 (1H, d, J=7.6 Hz).

Compound (4-34)
¹H-NMR (CDCl$_3$)δ: 5.49 (2H, s), 7.06 (1H, s), 7.31 (2H, m), 7.39 (1H, m), 7.54 (1H, d, J=7.6 Hz).

Compound (4-35)
¹H-NMR (CDCl$_3$)δ: 5.40 (2H, s), 7.06 (1H, s), 7.14 (1H, m), 7.33 (1H, m), 7.38 (1H, s).

Compound (4-36)
¹H-NMR (CDCl$_3$)δ: 2.49 (3H, s), 5.33 (2H, s), 7.02 (1H, d, J=5.2 Hz), 7.05-7.07 (2H, m).

Compound (4-37)
¹H-NMR (CDCl$_3$)δ: 3.83 (3H, s), 5.29 (2H, s), 6.23 (1H, d, J=3.2 Hz), 7.05 (1H, s), 7.32 (1H, t, J=3.2).

Compound (4-39)
¹H-NMR (CDCl$_3$)δ: 5.39 (2H, s), 7.01-7.05 (2H, m), 7.14 (1H, d, J=9.32 Hz), 7.19 (1H, d, J=7.6 Hz), 7.31-7.37 (1H, m).

Compound (4-40)
¹H-NMR (CDCl$_3$)δ: 5.36 (2H, s), 7.04-7.08 (3H, m), 7.38-7.42 (2H, m).

Compound (4-41)
¹H-NMR (CDCl$_3$)δ: 5.60 (2H, s), 7.06 (1H, s), 7.44-7.48 (1H, m), 7.62 (2H, d, J=4.0 Hz), 7.71 (1H, d, J=7.68 Hz).

Compound (4-42)
¹H-NMR (CDCl$_3$)δ: 5.51 (2H, s), 6.88-6.90 (1H, m), 6.95-6.97 (2H, m), 7.02 (1H, s), 7.07-7.15 (2H, m), 7.27-7.33 (3H, m), 7.50-7.52 (1H, m).

Compound (4-43)
¹H-NMR (CDCl$_3$)δ: 5.60 (2H, s), 7.07 (1H, s), 7.47 (1H, t, J=7.64 Hz), 7.59 (1H, t, J=7.48 Hz), 7.65 (1H, d, J=7.68 Hz), 7.70 (1H, d, J=7.8 Hz).

Compound (4-44)

¹H-NMR (CDCl₃)δ: 2.68 (6H, s), 4.94 (2H, s), 6.55 (1H, s), 7.09 (1H, t, J=7.4 Hz), 7.18 (2H, d, J=8.92 Hz), 7.27-7.29 (1H, m).

Compound (4-45)

¹H-NMR (CDCl₃)δ: 2.48 (3H, s), 5.50 (2H, s), 7.07 (1H, s), 7.16-7.20 (1H, m), 7.31-7.36 (2H, m), 7.43 (1H, d, J=7.36 Hz).

Compound (4-46)

¹H-NMR (CDCl₃)δ: 0.98 (3H, t, J=7.2 Hz), 1.58-1.67 (2H, m), 2.67 (2H, t, J=7.6 Hz), 5.42 (2H, s), 7.07 (1H, s), 7.19-7.24 (2H, m), 7.29-7.32 (1H, m), 7.40 (1H, d, J=7.6 Hz).

Compound (4-47)

¹H-NMR (CDCl₃)δ: 1.26 (6H, d, J=6.84 Hz), 3.14-3.21 (1H, m), 5.45 (2H, s), 7.07 (1H, s), 7.17-7.23 (1H, m), 7.35-7.38 (3H, m).

Compound (4-48)

¹H-NMR (CDCl₃)δ: 1.37 (9H, s), 5.64 (2H, s), 7.27 (1H, t, J=7.2 Hz), 7.30-7.34 (1H, m), 7.37 (1H, s), 7.42-7.47 (2H, m).

Compound (4-49)

¹H-NMR (CDCl₃)δ: 5.49 (2H, s), 7.06 (1H, s), 7.07-7.11 (1H, m), 7.13-7.18 (1H, m), 7.20-7.24 (1H, m).

Compound (4-50)

¹H-NMR (CDCl₃)δ: 5.42 (2H, s), 6.82-6.90 (2H, m), 7.05 (1H, s), 7.42-7.48 (1H, m).

Compound (4-51)

¹H-NMR (CDCl₃)δ: 5.45 (2H, s), 6.98-7.07 (3H, m), 7.16-7.20 (1H, m).

Compound (4-52)

¹H-NMR (CDCl₃)δ: 5.49 (2H, s), 6.90-6.96 (2H, m), 7.08 (1H, s), 7.31-7.39 (1H, m).

Compound (4-53)

¹H-NMR (CDCl₃)δ: 2.60 (3H, s), 5.42 (2H, s), 7.06 (1H, s), 7.13-7.16 (1H, m), 7.70 (1H, d, J=7.52 Hz), 8.47-8.49 (1H, m).

Compound (4-54)

¹H-NMR (CDCl₃)δ: 2.40 (3H, s), 5.53 (2H, s), 7.06 (1H, s), 7.18-7.21 (1H, m), 7.52 (1H, d, J=7.6 Hz), 8.46 (1H, d, J=4.52 Hz).

Compound (4-55)

¹H-NMR (CDCl₃)δ: 2.39 (3H, s), 5.44 (2H, s), 7.15 (1H, d, J=4.96 Hz), 7.25 (1H, s), 8.47 (1H, d, J=4.96 Hz), 8.57 (1H, s).

Compound (4-56)

¹H-NMR (CDCl₃)δ: 2.32 (3H, s), 5.41 (2H, s), 7.05 (1H, s), 7.32 (1H, d, J=4.8 Hz), 8.43 (1H, s), 8.47 (1H, d, J=4.8 Hz).

Compound (4-57)

¹H-NMR (CDCl₃)δ: 3.62 (3H, s), 4.65 (2H, s), 6.05-6.06 (1H, m), 6.55 (2H, s), 6.60 (1H, s).

Compound (4-58)

¹H-NMR (CDCl₃) δδ: 4.36-4.42 (2H, m), 5.48 (2H, s), 6.89 (1H, d, J=8.24 Hz), 7.05-7.09 (2H, m), 7.32-7.37 (1H, m), 7.45 (1H, d, J=7.56 Hz).

Compound (4-59)

¹H-NMR (CDCl₃)δ: 5.37 (2H, s), 7.05 (1H, s), 7.27-7.33 (3H, m), 7.42 (1H, s).

Compound (4-60)

¹H-NMR (CDCl₃)δ: 5.36 (2H, s), 7.04 (1H, s), 7.35 (4H, m).

Compound (4-61)

¹H-NMR (CDCl₃)δ: 3.37 (3H, s), 4.54 (2H, s), 5.49 (2H, s), 7.06 (1H, s), 7.30-7.40 (3H, m), 7.44-7.46 (1H, m).

Compound (4-62)

¹H-NMR (CDCl₃)δ: 5.49 (2H, s), 7.07 (1H, s), 7.19-7.23 (1H, m), 7.35 (1H, t, J=7.36 Hz), 7.50 (1H, d, J=7.6 Hz), 7.60 (1H, d, J=7.88 Hz).

Compound (4-63)

¹H-NMR (CDCl₃)δ: 5.31 (2H, s), 7.00 (1H, s), 7.32-7.55 (8H, m), 7.59-7.64 (1H, m).

Compound (4-64)

¹H-NMR (CDCl₃)δ: 3.51-3.59 (2H, m), 5.46 (2H, s), 7.05 (1H, s), 7.36-7.38 (3H, m), 7.48-7.50 (1H, m).

Compound (4-65)

¹H-NMR (CDCl₃)δ: 5.52 (2H, s), 7.06 (1H, s), 7.23 (1H, d, J=7.84 Hz), 7.42 (1H, d, J=7.36 Hz), 7.46 (1H, d, J=8.0 Hz).

Compound (4-66)

¹H-NMR (CDCl₃)δ: 5.47 (2H, s), 7.06 (1H, s), 7.26-7.28 (1H, m), 7.42-7.44 (2H, m).

Compound (4-67)

¹H-NMR (CDCl₃)δ: 5.47 (2H, s), 7.07 (1H, s), 7.27 (1H, d, J=2.44 Hz), 7.32-7.34 (1H, m), 7.50 (1H, d, J=2.4 Hz).

Compound (4-68)

¹H-NMR (CDCl₃)δ: 5.67 (2H, s), 7.09 (1H, s), 7.26-7.28 (1H, m), 7.37 (2H, d, J=7.92 Hz).

Compound (4-69)

¹H-NMR (CDCl₃)δ: 5.35 (2H, s), 6.37-6.38 (1H, m), 6.50 (1H, d, J=3.2 Hz), 7.06 (1H, s), 7.45 (1H, d, J=1.12 Hz).

Compound (4-70)

¹H-NMR (CDCl₃)δ: 5.28 (2H, s), 6.48 (1H, s), 7.05 (1H, s), 7.41 (1H, m), 7.53 (1H, s).

Compound (4-71)

¹H-NMR (CDCl₃)δ: 2.32 (3H, s), 5.21 (2H, s), 6.39 (1H, d, J=1.76 Hz), 7.05 (1H, s), 7.27 (1H, d, J=1.84 Hz).

Compound (4-72)

¹H-NMR (CDCl₃)δ: 2.26 (3H, s), 2.30 (3H, s), 5.42 (2H, s), 7.07 (1H, s), 7.12 (1H, t, J=7.52 Hz), 7.18 (1H, d, J=7.24 Hz), 7.22 (1H, s).

Compound (4-73)

¹H-NMR (CDCl₃)δ: 2.40 (6H, s), 5.48 (2H, s), 7.02-7.08 (3H, m), 7.15-7.19 (1H, m).

Compound (4-74)

¹H-NMR (CDCl₃)δ: 2.40 (3H, s), 5.42 (2H, s), 7.06 (1H, s), 7.15 (1H, t, J=7.8 Hz), 7.30 (1H, d, J=7.4 Hz), 7.38 (1H, d, J=7.88 Hz).

Compound (4-75)

¹H-NMR (CDCl₃)δ: 2.37 (3H, s), 5.36 (2H, s), 7.05 (1H, s), 7.16-7.20 (2H, m), 7.32 (1H, d, J=8.04 Hz).

Compound (4-76)

¹H-NMR (CDCl₃)δ: 2.43 (3H, s), 5.58 (2H, s), 7.09 (1H, s), 7.13 (1H, d, J=7.44 Hz), 7.22 (1H, t, J=7.6 Hz), 7.28 (1H, d, J=7.92 Hz).

Compound (4-77)

¹H-NMR (CDCl₃)δ: 2.32 (3H, s), 5.36 (2H, s), 7.06 (1H, s), 7.14 (1H, d, J=8.12 Hz), 7.21-7.24 (1H, m), 7.38 (1H, d, J=1.84 Hz).

Compound (4-78)

¹H-NMR (CDCl₃)δ: 2.22 (3H, s), 3.83 (3H, s), 5.41 (2H, s), 6.88 (1H, d, J=8.2 Hz), 7.01 (1H, d, J=7.6 Hz), 7.06 (1H, s), 7.20 (1H, t, J=7.92 Hz).

Compound (4-79)

¹H-NMR (CDCl₃)δ: 2.25 (3H, s), 3.73-3.84 (3H, m), 4.76 (2H, s), 6.32 (1H, s), 6.63-6.75 (2H, m), 7.11 (1H, d, J=8.12 Hz).

Compound (4-80)

¹H-NMR (CDCl₃)δ: 2.42 (3H, s), 5.44 (2H, s), 7.07 (1H, s), 7.33 (1H, d, J=7.92 Hz), 7.52 (1H, d, J=7.8 Hz), 7.65 (1H, s).

Compound (4-81)

¹H-NMR (CDCl₃)δ: 2.29 (3H, s), 3.78 (3H, s), 5.37 (2H, s), 6.82 (1H, d, J=8.16 Hz), 6.95 (1H, s), 7.06 (1H, s), 7.12 (1H, d, J=8.36 Hz).

Compound (4-82)

¹H-NMR (CDCl₃)δ: 1.66 (3H, d, J=6.48 Hz), 2.39 (3H, s), 6.14-6.19 (1H, m), 6.98 (1H, s), 7.13-7.17 (1H, m), 7.18-7.21 (2H, m), 7.42-7.44 (1H, m).

Compound (4-83)

¹H-NMR (CDCl₃)δ: 0.99 (3H, t, J=7.42 Hz), 1.84-1.94 (1H, m), 1.98-2.08 (1H, m), 2.41 (3H, s), 5.92-5.95 (1H, m), 6.95 (1H, s), 7.12-7.21 (3H, m), 7.36-7.39 (1H, m).

Compound (4-84)

¹H-NMR (CDCl₃)δ: 0.96 (3H, t, J=7.36 Hz), 1.35-1.42 (1H, m), 1.48-1.53 (1H, m), 1.73-1.80 (1H, m), 1.96-2.04 (1H, m), 2.41 (3H, s), 5.99-6.02 (1H, m), 6.94 (1H, s), 7.12-7.20 (3H, m), 7.36-7.38 (1H, m).

Compound (4-85)

¹H-NMR (CDCl₃)δ: 0.86 (3H, d, J=6.88 Hz), 1.10 (3H, d, J=6.56 Hz), 2.16-2.19 (1H, m), 2.43 (3H, s), 5.72 (1H, d, J=7.72 Hz), 6.92 (1H, s), 7.11-7.17 (3H, m), 7.31-7.34 (1H, m).

Compound (4-86)

¹H-NMR (CDCl₃)δ: 0.34-0.37 (1H, m), 0.69-0.76 (3H, m), 1.39-1.48 (1H, m), 2.19 (3H, s), 4.90 (1H, d, J=9.32 Hz), 6.41 (1H, s), 7.14-7.19 (2H, m), 7.26-7.28 (1H, m), 7.61-7.63 (1H, m).

Reference Production Example 2

A reaction was performed in the same manner as in Reference Production Example 1 except that 2-methylbenzyl alcohol was used instead of 2-methoxybenzyl alcohol and 2-bromothiazole was used instead of 2,5-dibromothiazole, whereby 2-(2-methylbenzyloxy)thiazole (compound (9-1)) was obtained.

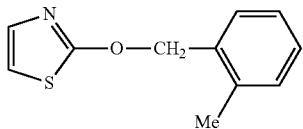 [SMILES: Cc1ccccc1COc1nccs1]

¹H-NMR (CDCl₃)δ: 2.39 (3H, s), 5.44 (2H, s), 6.66 (1H, d, J=3.6 Hz), 7.14 (1H, d, J=3.6 Hz), 7.23 (3H, m), 7.40 (1H, m).

Reference Production Example 3

A reaction was performed in the same manner as in Reference Production Example 2 except that 2-chlorothiazole was used instead of 2-bromothiazole, whereby 2-(2-methylbenzyloxy)thiazole (compound (9-1)) was obtained.

Reference Production Example 4

A reaction was performed in the same manner as in Reference Production Example 2 except that 2-ethylbenzyl alcohol was used instead of 2-methylbenzyl alcohol, whereby 2-(2-ethylbenzyloxy)thiazole (compound (9-2)) was obtained.

¹H-NMR (CDCl₃)δ: 1.27 (3H, t, J=7.2 Hz), 2.75 (2H, q, J=7.2 Hz), 5.42 (2H, s), 6.70 (1H, d, J=3.6 Hz), 7.16 (1H, d, J=3.6 Hz), 7.23 (3H, m), 7.40 (1H, m).

Reference Production Example 5

A reaction was performed in the same manner as in Reference Production Example 2 except that 1-(2-naphthyl)ethanol was used instead of 2-methylbenzyl alcohol, whereby 2-(1-(2-naphthyl)ethoxy)thiazole (compound (9-3)) was obtained. The compound (9-3) was subjected to the next reaction without performing ¹H-NMR measurement.

Specific examples of the compound of the present invention include compounds (1a-I) to (1a-XXI), (1b-I) to (1b-XXI), and (1c-I) to (1c-XXI) of the present invention below. Here, R¹ and Ar in the formula each represent any one of combinations shown below.

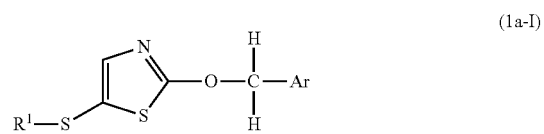
(1a-I)

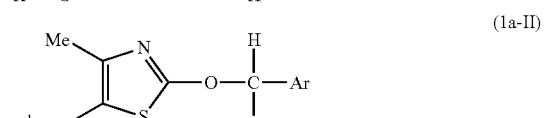
(1a-II)

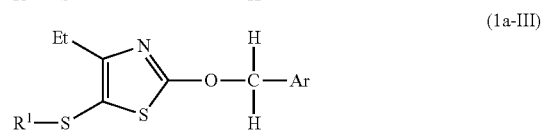
(1a-III)

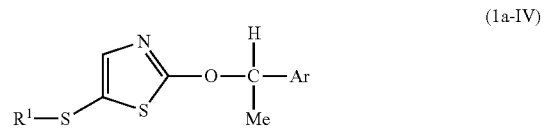
(1a-IV)

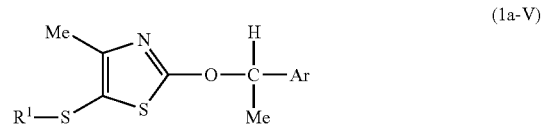
(1a-V)

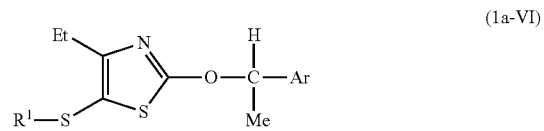
(1a-VI)

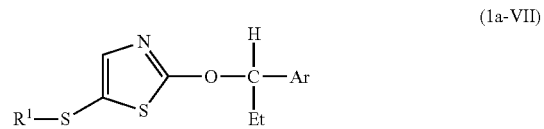
(1a-VII)

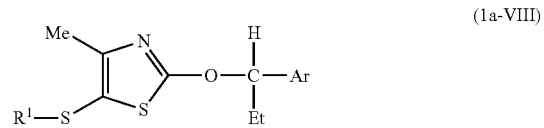
(1a-VIII)

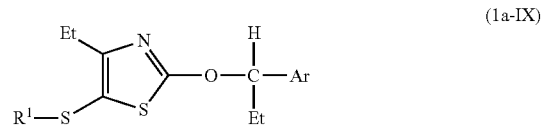
(1a-IX)

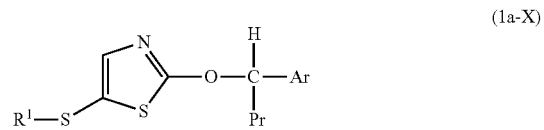
(1a-X)

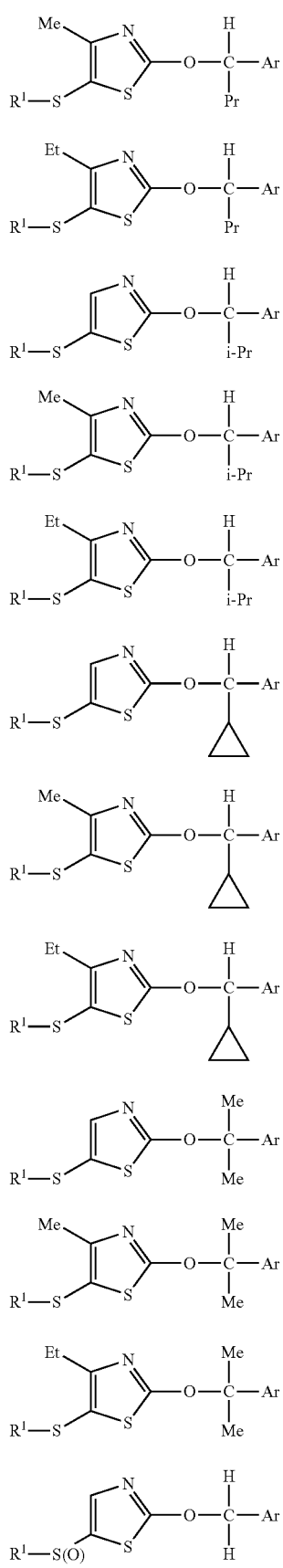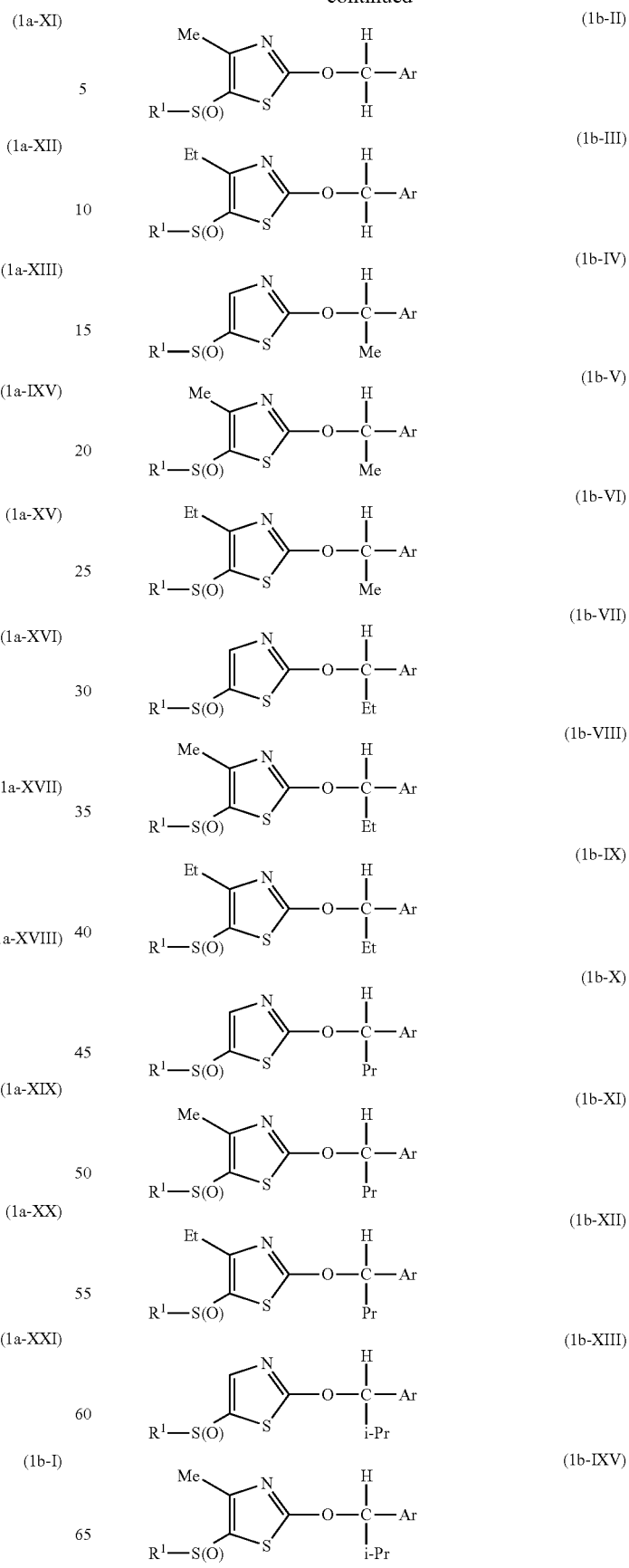

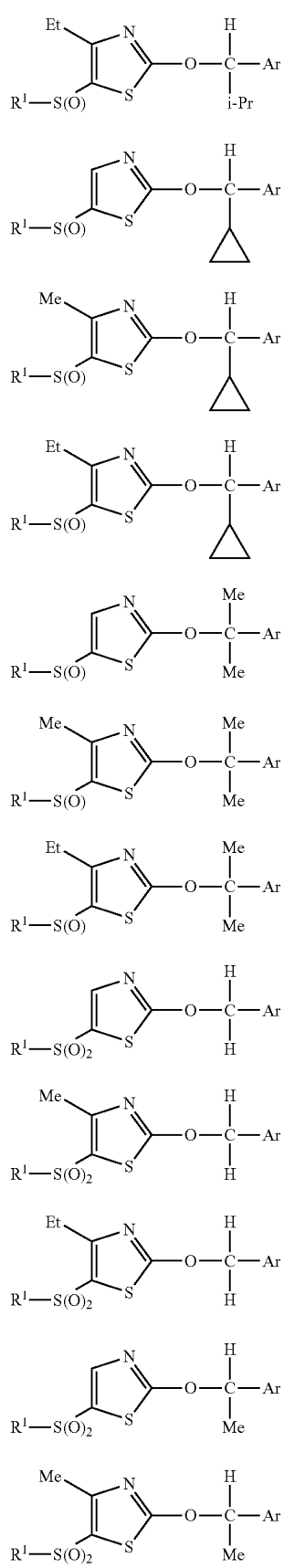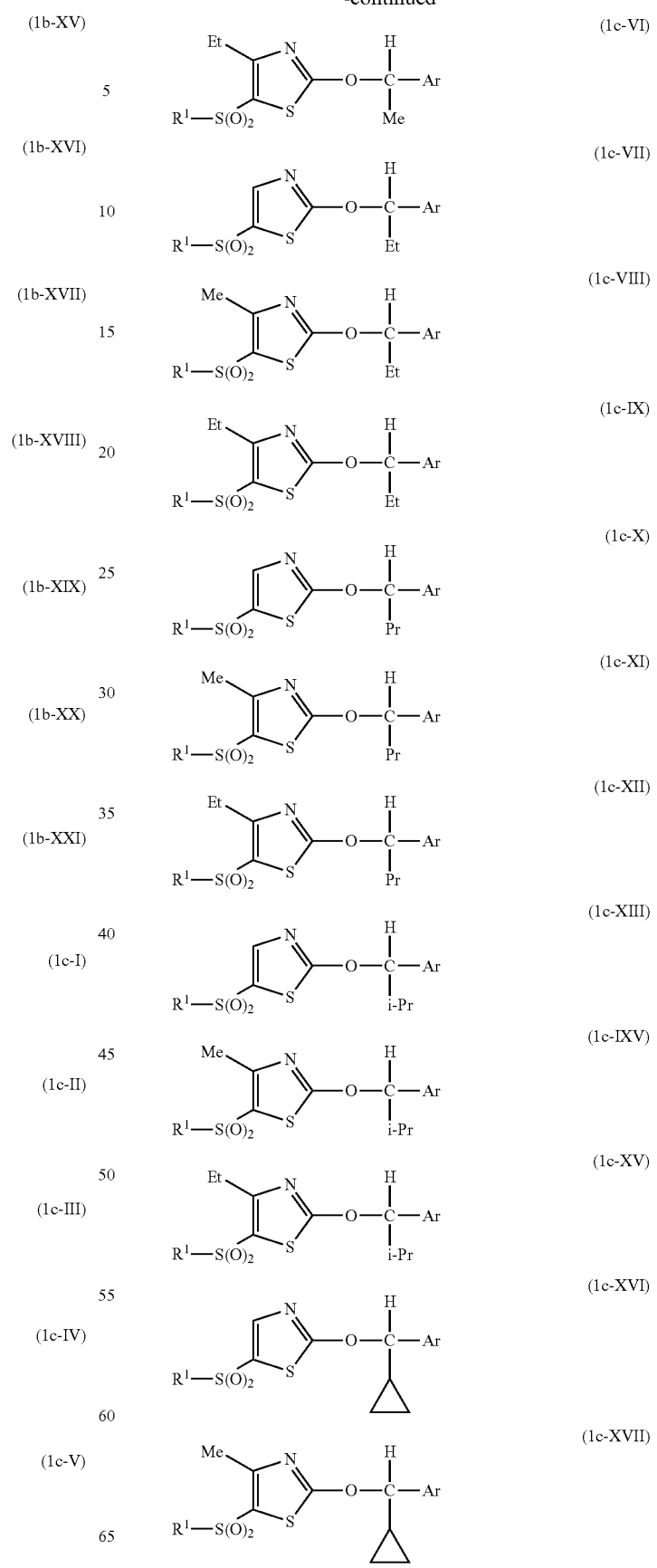

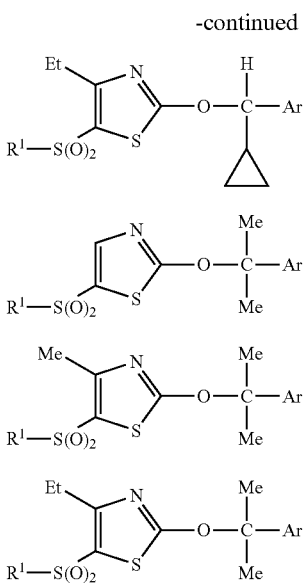

Combinations R¹ and Ar in the compounds (1a-I) to (1a-XXI), (1b-I) to (1b-XXI), and (1c-I) to (1c-XXI) of the present invention are shown below. Hereafter, in bracket [ ], a branch number, a group represented by R¹, a group represented by Ar are described in this order.

[Branch number, R¹, Ar]=[1, Me, Ph]; [2, Me, 2-F-Ph]; [3, Me, 3-F-Ph]; [4, Me, 4-F-Ph]; [5, Me, 2-Cl-Ph]; [6, Me, 3-Cl-Ph]; [7, Me, 4-Cl-Ph]; [8, Me, 2-Br-Ph]; [9, Me, 3-Br-Ph]; [10, Me, 4-Br-Ph]; [11, Me, 2,3-F$_2$-Ph]; [12, Me, 2,4-F$_2$-Ph]; [13, Me, 2,5-F$_2$-Ph]; [14, Me, 2,6-F$_2$-Ph]; [15, Me, 3,4-F$_2$-Ph]; [16, Me, 3,5-F$_2$-Ph]; [17, Me, 2,3,4-F$_3$-Ph]; [18, Me, 2,4,6-F$_3$-Ph]; [19, Me, 2,3,5,6-F$_4$-Ph]; [20, Me, 2,3,4,5,6-F$_5$-Ph]; [21, Me, 2,3-Cl$_2$-Ph]; [22, Me, 2,4-Cl$_2$-Ph]; [23, Me, 2,5-Cl$_2$-Ph]; [24, Me, 2,6-Cl$_2$-Ph]; [25, Me, 3,4-Cl$_2$-Ph]; [26, Me, 3,5-Cl$_2$-Ph]; [27, Me, 2-F-4-Cl-Ph]; [28, Me, 2-Me-Ph]; [29, Me, 3-Me-Ph]; [30, Me, 4-Me-Ph]; [31, Me, 2-Et-Ph]; [32, Me, 3-Et-Ph]; [33, Me, 4-Et-Ph]; [34, Me, 2-Pr-Ph]; [35, Me, 3-Pr-Ph]; [36, Me, 4-Pr-Ph]; [37, Me, 2-i-Pr-Ph]; [38, Me, 3-i-Pr-Ph]; [39, Me, 4-i-Pr-Ph]; [40, Me, 2-t-Bu-Ph]; [41, Me, 3-t-Bu-Ph]; [42, Me, 4-t-Bu-Ph]; [43, Me, 2,3-Me$_2$-Ph]; [44, Me, 2,4-Me$_2$-Ph]; [45, Me, 2,5-Me$_2$-Ph]; [46, Me, 2,6-Me$_2$-Ph]; [47, Me, 3,4-Me$_2$-Ph]; [48, Me, 3,5-Me$_2$-Ph]; [49, Me, 2,3,4-Me$_3$-Ph]; [50, Me, 2,4,6-Me$_3$-Ph]; [51, Me, 2,3-Et$_2$-Ph]; [52, Me, 2,4-Et$_2$-Ph]; [53, Me, 2,5-Et$_2$-Ph]; [54, Me, 2,6-Et$_2$-Ph]; [55, Me, 3,4-Et$_2$-Ph]; [56, Me, 3,5-Et$_2$-Ph]; [57, Me, 2,4,6-Et$_3$-Ph]; [58, Me, 2-F-3-Me-Ph]; [59, Me, 2-F-4-Me-Ph]; [60, Me, 2-F-5-Me-Ph]; [61, Me, 2-F-6-Me-Ph]; [62, Me, 3-F-2-Me-Ph]; [63, Me, 3-F-4-Me-Ph]; [64, Me, 3-F-5-Me-Ph]; [65, Me, 4-F-2-Me-Ph]; [66, Me, 4-F-3-Me-Ph]; [67, Me, 5-F-2-Me-Ph]; [68, Me, 2-Cl-3-Me-Ph]; [69, Me, 2-Cl-4-Me-Ph]; [70, Me, 2-Cl-5-Me-Ph]; [71, Me, 2-Cl-6-Me-Ph]; [72, Me, 3-Cl-2-Me-Ph]; [73, Me, 3-Cl-4-Me-Ph]; [74, Me, 3-Cl-5-Me-Ph]; [75, Me, 4-Cl-2-Me-Ph]; [76, Me, 4-Cl-3-Me-Ph]; [77, Me, 5-Cl-2-Me-Ph]; [78, Me, 2-F-3-Et-Ph]; [79, Me, 2-F-4-Et-Ph]; [80, Me, 2-F-5-Et-Ph]; [81, Me, 2-F-6-Et-Ph]; [82, Me, 3-F-2-Et-Ph]; [83, Me, 3-F-4-Et-Ph]; [84, Me, 3-F-5-Et-Ph]; [85, Me, 4-F-2-Et-Ph]; [86, Me, 4-F-3-Et-Ph]; [87, Me, 5-F-2-Et-Ph]; [88, Me, 2-Cl-3-Et-Ph]; [89, Me, 2-Cl-4-Et-Ph]; [90, Me, 2-Cl-5-Et-Ph]; [91, Me, 2-Cl-6-Et-Ph]; [92, Me, 3-Cl-2-Et-Ph]; [93, Me, 3-Cl-4-Et-Ph]; [94, Me, 3-Cl-5-Et-Ph]; [95, Me, 4-Cl-2-Et-Ph]; [96, Me, 4-Cl-3-Et-Ph]; [97, Me, 5-Cl-2-Et-Ph]; [98, Me, 2-Et-3-Me-Ph]; [99, Me, 2-Et-4-Me-Ph]; [100, Me, 2-Et-5-Me-Ph]; [101, Me, 2-Et-6-Me-Ph]; [102, Me, 3-Et-2-Me-Ph]; [103, Me, 3-Et-4-Me-Ph]; [104, Me, 3-Et-5-Me-Ph]; [105, Me, 4-Et-2-Me-Ph]; [106, Me, 4-Et-3-Me-Ph]; [107, Me, 5-Et-2-Me-Ph]; [108, Me, 2-OMe-Ph]; [109, Me, 3-OMe-Ph]; [110, Me, 4-OMe-Ph]; [111, Me, 2-OEt-Ph]; [112, Me, 3-OEt-Ph]; [113, Me, 4-OEt-Ph]; [114, Me, 2-OPr-Ph]; [115, Me, 3-OPr-Ph]; [116, Me, 4-OPr-Ph]; [117, Me, 2-Oi-Pr-Ph]; [118, Me, 3-Oi-Pr-Ph]; [119, Me, 4-Oi-Pr-Ph]; [120, Me, 2-Ot-Bu-Ph]; [121, Me, 3-Ot-Bu-Ph]; [122, Me, 4-Ot-Bu-Ph]; [123, Me, 2,3-(OMe)$_2$-Ph]; [124, Me, 2,4-(OMe)$_2$-Ph]; [125, Me, 2,5-(OMe)$_2$-Ph]; [126, Me, 2,6-(OMe)$_2$-Ph]; [127, Me, 3,4-(OMe)$_2$-Ph]; [128, Me, 3,5-(OMe)$_2$-Ph]; [129, Me, 2,3,4-(OMe)$_3$-Ph]; [130, Me, 2,4,6-(OMe)$_3$-Ph]; [131, Me, 2,3-(OEt)$_2$-Ph]; [132, Me, 2,4-(OEt)$_2$-Ph]; [133, Me, 2,5-(OEt)$_2$-Ph]; [134, Me, 2,6-(OEt)$_2$-Ph]; [135, Me, 3,4-(OEt)$_2$-Ph]; [136, Me, 3,5-(OEt)$_2$-Ph]; [137, Me, 2,4,6-(OEt)$_3$-Ph]; [138, Me, 2-F-3-OMe-Ph]; [139, Me, 2-F-4-OMe-Ph]; [140, Me, 2-F-5-OMe-Ph]; [141, Me, 2-F-6-OMe-Ph]; [142, Me, 3-F-2-OMe-Ph]; [143, Me, 3-F-4-OMe-Ph]; [144, Me, 3-F-5-OMe-Ph]; [145, Me, 4-F-2-OMe-Ph]; [146, Me, 4-F-3-OMe-Ph]; [147, Me, 5-F-2-OMe-Ph]; [148, Me, 2-Cl-3-OMe-Ph]; [149, Me, 2-Cl-4-OMe-Ph]; [150, Me, 2-Cl-5-OMe-Ph]; [151, Me, 2-Cl-6-OMe-Ph]; [152, Me, 3-Cl-2-OMe-Ph]; [153, Me, 3-Cl-4-OMe-Ph]; [154, Me, 3-Cl-5-OMe-Ph]; [155, Me, 4-Cl-2-OMe-Ph]; [156, Me, 4-Cl-3-OMe-Ph]; [157, Me, 5-Cl-2-OMe-Ph]; [158, Me, 2-F-3-OEt-Ph]; [159, Me, 2-F-4-OEt-Ph]; [160, Me, 2-F-5-OEt-Ph]; [161, Me, 2-F-6-OEt-Ph]; [162, Me, 3-F-2-OEt-Ph]; [163, Me, 3-F-4-OEt-Ph]; [164, Me, 3-F-5-OEt-Ph]; [165, Me, 4-F-2-OEt-Ph]; [166, Me, 4-F-3-OEt-Ph]; [167, Me, 5-F-2-OEt-Ph]; [168, Me, 2-Cl-3-OEt-Ph]; [169, Me, 2-Cl-4-OEt-Ph]; [170, Me, 2-Cl-5-OEt-Ph]; [171, Me, 2-Cl-6-OEt-Ph]; [172, Me, 3-Cl-2-OEt-Ph]; [173, Me, 3-Cl-4-OEt-Ph]; [174, Me, 3-Cl-5-OEt-Ph]; [175, Me, 4-Cl-2-OEt-Ph]; [176, Me, 4-Cl-3-OEt-Ph]; [177, Me, 5-Cl-2-OEt-Ph]; [178, Me, 2-Et-3-OMe-Ph]; [179, Me, 2-Et-4-OMe-Ph]; [180, Me, 2-Et-5-OMe-Ph]; [181, Me, 2-Et-6-OMe-Ph]; [182, Me, 3-Et-2-OMe-Ph]; [183, Me, 3-Et-4-OMe-Ph]; [184, Me, 3-Et-5-OMe-Ph]; [185, Me, 4-Et-2-OMe-Ph]; [186, Me, 4-Et-3-OMe-Ph]; [187, Me, 5-Et-2-OMe-Ph]; [188, Me, 2-OMe-3-Me-Ph]; [189, Me, 2-OMe-4-Me-Ph]; [190, Me, 2-OMe-5-Me-Ph]; [191, Me, 2-OMe-6-Me-Ph]; [192, Me, 3-OMe-2-Me-Ph]; [193, Me, 3-OMe-4-Me-Ph]; [194, Me, 3-OMe-5-Me-Ph]; [195, Me, 4-OMe-2-Me-Ph]; [196, Me, 4-OMe-3-Me-Ph]; [197, Me, 5-OMe-2-Me-Ph]; [198, Me, 2-CF$_3$-Ph]; [199, Me, 3-CF$_3$-Ph]; [200, Me, 4-CF$_3$-Ph]; [201, Me, 2,3-(CF$_3$)$_2$-Ph]; [202, Me, 2,4-(CF$_3$)$_2$-Ph]; [203, Me, 2,5-(CF$_3$)$_2$-Ph]; [204, Me, 2,6-(CF$_3$)$_2$-Ph]; [205, Me, 3,5-(CF$_3$)$_2$-Ph]; [206, Me, 2-CH$_2$CF$_3$-Ph]; [207, Me, 3-CH$_2$CF$_3$-Ph]; [208, Me, 4-CH$_2$CF$_3$-Ph]; [209, Me, 2-CF$_2$CF$_3$-Ph]; [210, Me, 3-CF$_2$CF$_3$-Ph]; [211, Me, 4-CF$_2$CF$_3$-Ph]; [212, Me, 2-CF$_2$CF$_2$CF$_3$-Ph]; [213, Me, 3-CF$_2$CF$_2$CF$_3$-Ph]; [214, Me, 4-CF$_2$CF$_2$CF$_3$-Ph]; [215, Me, 2-OCF$_3$-Ph]; [216, Me, 3-OCF$_3$-Ph]; [217, Me, 4-OCF$_3$-Ph]; [218, Me, 2-OCH$_2$CF$_3$-Ph]; [219, Me, 3-OCH$_2$CF$_3$-Ph]; [220, Me, 4-OCH$_2$CF$_3$-Ph]; [221, Me, 2-SMe-Ph]; [222, Me, 3-SMe-Ph]; [223, Me, 4-SMe-Ph]; [224, Me, 2-SCF$_3$-Ph]; [225, Me, 3-SCF$_3$-Ph]; [226, Me, 4-SCF$_3$-Ph]; [227, Me, 2-CH$_2$=CH-Ph]; [228, Me, 3-CH$_2$=CH-Ph]; [229, Me, 4-CH$_2$=CH-Ph]; [230, Me, 2-ethynyl-Ph]; [231, Me, 4-CH$_2$=CHCH$_2$-Ph]; [232, Me, 2-CH$_2$=CHCH$_2$O-Ph]; [233, Me, 2-propynyloxy-Ph]; [234, Me, 2-OH-Ph]; [235, Me, 3-OH-Ph]; [236, Me, 4-OH-Ph]; [237, Me, 2-CN-Ph]; [238, Me, 3-CN-Ph]; [239, Me, 4-CN-Ph]; [240, Me, 2-NO$_2$-Ph]; [241, Me, 3-NO$_2$-Ph]; [242, Me, 4-NO$_2$-Ph]; [243, Me, 2-Ph-Ph]; [244, Me, 3-Ph-Ph]; [245, Me, 4-Ph- Ph]; [246, Me, 2-(2-Cl-Ph)-Ph]; [247, Me, 3-(4-Cl-Ph)-Ph]; [248, Me, 4-(3-Cl-Ph)-Ph]; [249, Me, 2-OPh-Ph]; [250, Me, 3-OPh-Ph]; [251, Me, 4-OPh-Ph]; [252, Me, 2-CN-6-Me-Ph]; [253, Me, 3-CN-2-Me-Ph]; [254, Me, 4-CN-2-Me-Ph]; [255, Me, 2-NMe$_2$-Ph]; [256, Me, 3-NMe$_2$-Ph]; [257, Me, 4-NMe$_2$-Ph]; [258, Me, 2-Ac-Ph]; [259, Me, 3-Ac-Ph]; [260, Me, 4-Ac-Ph]; [261, Me, 2-CO$_2$Me-Ph]; [262, Me, 3-CO$_2$Et-Ph]; [263, Me, 4-CO$_2$t-Bu-Ph]; [264, Me, 2-MeOCH$_2$-Ph]; [265, Me, 3-MeOCH$_2$-Ph]; [266, Me, 4-MeOCH$_2$-Ph]; [267, Me, 2-Me-5-CF$_3$-Ph]; [268, Me, 2-Me-5-NO$_2$-Ph]; [269, Me, 5-CN-2-Me-Ph]; [270, Me, 1-Nap]; [271, Me, 2-Nap]; [272, Me, 1-Me-2-Nap]; [273, Me, 2-Me-1-Nap]; [274, Me, 1-OMe-2-Nap]; [275, Me, 2-OMe-1-Nap]; [276, Me, 2-Thie]; [277, Me, 3-Thie]; [278, Me, 3-Me-2-Thie]; [279, Me, 4-Me-2-Thie]; [280, Me, 5-Me-2-Thie]; [281, Me, 3-OMe-2-Thie]; [282, Me, 4-OMe-2-Thie]; [283, Me, 5-OMe-2-Thie]; [284, Me, 2-Me-3-Thie]; [285, Me, 4-Me-3-Thie]; [286, Me, 5-Me-3-Thie]; [287, Me, 2-OMe-3-Thie]; [288, Me, 4-OMe-3-Thie]; [289, Me, 5-OMe-3-Thie]; [290, Me, 2-Fur]; [291, Me, 3-Fur]; [292, Me, 3-Me-2-Fur]; [293, Me, 4-Me-2-Fur]; [294, Me, 5-Me-2-Fur]; [295, Me, 2-Me-3-Fur]; [296, Me, 4-Me-3-Fur]; [297, Me, 5-Me-3-Fur]; [298, Me, 2-Pyrr]; [299, Me, 3-Pyrr]; [300, Me, 1-Me-2-Pyrr]; [301, Me, 1-Me-3-Pyrr]; [302, Me, 3-Me-2-Pyrr]; [303, Me, 4-Me-2-Pyrr]; [304, Me, 5-Me-2-Pyrr]; [305, Me, 2-Me-3-Pyrr]; [306, Me, 4-Me-3-Pyrr]; [307, Me, 5-Me-3-Pyrr]; [308, Me, 1,3-Me2-2-Pyrr]; [309, Me, 1,4-Me$_2$-2-Pyrr]; [310, Me, 1,5-Me$_2$-2-Pyrr]; [311, Me, 1,2-Me$_2$-3-Pyrr]; [312, Me, 1,4-Me$_2$-3-Pyrr]; [313, Me, 1,5-Me$_2$-3-Pyrr]; [314, Me, 2-Py]; [315, Me, 3-Py]; [316, Me, 4-Py]; [317, Me, 3-Me-2-Py]; [318, Me, 4-Me-2-Py]; [319, Me, 5-Me-2-Py]; [320, Me, 6-Me-2-Py]; [321, Me, 2-Me-3-Py]; [322, Me, 4-Me-3-Py]; [323, Me, 5-Me-3-Py]; [324, Me, 6-Me-3-Py]; [325, Me, 2-Me-4-Py]; [326, Me, 3-Me-4-Py]; [327, Me, 3,5-Me2-2-Py]; [328, Me, 3-OMe-2-Py]; [329, Me, 4-OMe-2-Py]; [330, Me, 5-OMe-2-Py]; [331, Me, 6-OMe-2-Py]; [332, Me, 2-OMe-3-Py]; [333, Me, 4-OMe-3-Py]; [334, Me, 5-OMe-3-Py]; [335, Me, 6-OMe-3-Py]; [336, Me, 2-OMe-4-Py]; [337, Me, 3-OMe-4-Py]; [338, Me, 5-Cl-2-Py]; [339, Me, 6-Cl-3-Py]; [340, Me, 5-CF$_3$-2-Py]; [341, Me, 6-CF$_3$-3-Py]; [342, Me, 1,3-Me$_2$-5-pyrazolyl]; [343, Me, 1-Me-2-imidazolyl]; [344, Me, 2-Thia]; [345, Me, 4-Thia]; [346, Me, 5-Me-4-Thia]; [347, Me, 5-Thia]; [348, Me, 4-Me-5-Thia]; [349, Me, 2,5-Me$_2$-4-Thia]; [350, Me, 2-Cl-5-Thia]; [351, Me, 2-CF$_3$-5-Thia]; [352, Et, Ph]; [353, Et, 2-F-Ph]; [354, Et, 3-F-Ph]; [355, Et, 4-F-Ph]; [356, Et, 2-Cl-Ph]; [357, Et, 3-Cl-Ph]; [358, Et, 4-Cl-Ph]; [359, Et, 2-Br-Ph]; [360, Et, 3-Br-Ph]; [361, Et, 4-Br-Ph]; [362, Et, 2,3-F$_2$-Ph]; [363, Et, 2,4-F$_2$-Ph]; [364, Et, 2,5-F$_2$-Ph]; [365, Et, 2,6-F$_2$-Ph]; [366, Et, 3,4-F$_2$-Ph]; [367, Et, 3,5-F$_2$-Ph]; [368, Et, 2,3,4-F$_3$-Ph]; [369, Et, 2,4,6-F$_3$-Ph]; [370, Et, 2,3,5,6-F$_4$-Ph]; [371, Et, 2,3,4,5,6-F$_5$-Ph]; [372, Et, 2,3-Cl$_2$-Ph]; [373, Et, 2,4-Cl$_2$-Ph]; [374, Et, 2,5-Cl$_2$-Ph]; [375, Et, 2,6-Cl$_2$-Ph]; [376, Et, 3,4-Cl$_2$-Ph]; [377, Et, 3,5-Cl$_2$-Ph]; [378, Et, 2-F-4-Cl-Ph]; [379, Et, 2-Me-Ph]; [380, Et, 3-Me-Ph]; [381, Et, 4-Me-Ph]; [382, Et, 2-Et-Ph]; [383, Et, 3-Et-Ph]; [384, Et, 4-Et-Ph]; [385, Et, 2-Pr-Ph]; [386, Et, 3-Pr-Ph]; [387, Et, 4-Pr-Ph]; [388, Et, 2-i-Pr-Ph]; [389, Et, 3-i-Pr-Ph]; [390, Et, 4-i-Pr-Ph]; [391, Et, 2-t-Bu-Ph]; [392, Et, 3-t-Bu-Ph]; [393, Et, 4-t-Bu-Ph]; [394, Et, 2,3-Me$_2$-Ph]; [395, Et, 2,4-Me$_2$-Ph]; [396, Et, 2,5-Me$_2$-Ph]; [397, Et, 2,6-Me$_2$-Ph]; [398, Et, 3,4-Me$_2$-Ph]; [399, Et, 3,5-Me$_2$-Ph]; [400, Et, 2,3,4-Me$_3$-Ph]; [401, Et, 2,4,6-Me3-Ph]; [402, Et, 2,3-Et$_2$-Ph]; [403, Et, 2,4-Et$_2$-Ph]; [404, Et, 2,5-Et$_2$-Ph]; [405, Et, 2,6-Et$_2$-Ph]; [406, Et, 3,4-Et$_2$-Ph]; [407, Et, 3,5-Et$_2$-Ph]; [408, Et, 2,4,6-Et$_3$-Ph]; [409, Et, 2-F-3-Me-Ph]; [410, Et, 2-F-4-Me-Ph]; [411, Et, 2-F-5-Me-Ph]; [412, Et, 2-F-6-Me-Ph]; [413, Et, 3-F-2-Me-Ph]; [414, Et, 3-F-4-Me-Ph]; [415, Et, 3-F-5-Me-Ph]; [416, Et, 4-F-2-Me-Ph]; [417, Et, 4-F-3-Me-Ph]; [418, Et, 5-F-2-Me-Ph]; [419, Et, 2-Cl-3-Me-Ph]; [420, Et, 2-Cl-4-Me-Ph]; [421, Et, 2-Cl-5-Me-Ph]; [422, Et, 2-Cl-6-Me-Ph]; [423, Et, 3-Cl-2-Me-Ph]; [424, Et, 3-Cl-4-Me-Ph]; [425, Et, 3-Cl-5-Me-Ph]; [426, Et, 4-Cl-2-Me-Ph]; [427, Et, 4-Cl-3-Me-Ph]; [428, Et, 5-Cl-2-Me-Ph]; [429, Et, 2-F-3-Et-Ph]; [430, Et, 2-F-4-Et-Ph]; [431, Et, 2-F-5-Et-Ph]; [432, Et, 2-F-6-Et-Ph]; [433, Et, 3-F-2-Et-Ph]; [434, Et, 3-F-4-Et-Ph]; [435, Et, 3-F-5-Et-Ph]; [436, Et, 4-F-2-Et-Ph]; [437, Et, 4-F-3-Et-Ph]; [438, Et, 5-F-2-Et-Ph]; [439, Et, 2-Cl-3-Et-Ph]; [440, Et, 2-Cl-4-Et-Ph]; [441, Et, 2-Cl-5-Et-Ph]; [442, Et, 2-Cl-6-Et-Ph]; [443, Et, 3-Cl-2-Et-Ph]; [444, Et, 3-Cl-4-Et-Ph]; [445, Et, 3-Cl-5-Et-Ph]; [446, Et, 4-Cl-2-Et-Ph]; [447, Et, 4-Cl-3-Et-Ph]; [448, Et, 5-Cl-2-Et-Ph]; [449, Et, 2-Et-3-Me-Ph]; [450, Et, 2-Et-4-Me-Ph]; [451, Et, 2-Et-5-Me-Ph]; [452, Et, 2-Et-6-Me-Ph]; [453, Et, 3-Et-2-Me-Ph]; [454, Et, 3-Et-4-Me-Ph]; [455, Et, 3-Et-5-Me-Ph]; [456, Et, 4-Et-2-Me-Ph]; [457, Et, 4-Et-3-Me-Ph]; [458, Et, 5-Et-2-Me-Ph]; [459, Et, 2-OMe-Ph]; [460, Et, 3-OMe-Ph]; [461, Et, 4-OMe-Ph]; [462, Et, 2-OEt-Ph]; [463, Et, 3-OEt-Ph]; [464, Et, 4-OEt-Ph]; [465, Et, 2-OPr-Ph]; [466, Et, 3-OPr-Ph]; [467, Et, 4-OPr-Ph]; [468, Et, 2-Oi-Pr-Ph]; [469, Et, 3-Oi-Pr-Ph]; [470, Et, 4-Oi-Pr-Ph]; [471, Et, 2-Ot-Bu-Ph]; [472, Et, 3-Ot-Bu-Ph]; [473, Et, 4-Ot-Bu-Ph]; [474, Et, 2,3-(OMe)$_2$-Ph]; [475, Et, 2,4-(OMe)$_2$-Ph]; [476, Et, 2,5-(OMe)$_2$-Ph]; [477, Et, 2,6-(OMe)$_2$-Ph]; [478, Et, 3,4-(OMe)$_2$-Ph]; [479, Et, 3,5-(OMe)$_2$-Ph]; [480, Et, 2,3,4-(OMe)$_3$-Ph]; [481, Et, 2,4,6-(OMe)$_3$-Ph]; [482, Et, 2,3-(OEt)$_2$-Ph]; [483, Et, 2,4-(OEt)$_2$-Ph]; [484, Et, 2,5-(OEt)$_2$-Ph]; [485, Et, 2,6-(OEt)$_2$-Ph]; [486, Et, 3,4-(OEt)$_2$-Ph]; [487, Et, 3,5-(OEt)$_2$-Ph]; [488, Et, 2,4,6-(OEt)$_3$-Ph]; [489, Et, 2-F-3-OMe-Ph]; [490, Et, 2-F-4-OMe-Ph]; [491, Et, 2-F-5-OMe-Ph]; [492, Et, 2-F-6-OMe-Ph]; [493, Et, 3-F-2-OMe-Ph]; [494, Et, 3-F-4-OMe-Ph]; [495, Et, 3-F-5-OMe-Ph]; [496, Et, 4-F-2-OMe-Ph]; [497, Et, 4-F-3-OMe-Ph]; [498, Et, 5-F-2-OMe-Ph]; [499, Et, 2-Cl-3-OMe-Ph]; [500, Et, 2-Cl-4-OMe-Ph]; [501, Et, 2-Cl-5-OMe-Ph]; [502, Et, 2-Cl-6-OMe-Ph]; [503, Et, 3-Cl-2-OMe-Ph]; [504, Et, 3-Cl-4-OMe-Ph]; [505, Et, 3-Cl-5-OMe-Ph]; [506, Et, 4-Cl-2-OMe-Ph]; [507, Et, 4-Cl-3-OMe-Ph]; [508, Et, 5-Cl-2-OMe-Ph]; [509, Et, 2-F-3-OEt-Ph]; [510, Et, 2-F-4-OEt-Ph]; [511, Et, 2-F-5-OEt-Ph]; [512, Et, 2-F-6-OEt-Ph]; [513, Et, 3-F-2-OEt-Ph]; [514, Et, 3-F-4-OEt-Ph]; [515, Et, 3-F-5-OEt-Ph]; [516, Et, 4-F-2-OEt-Ph]; [517, Et, 4-F-3-OEt-Ph]; [518, Et, 5-F-2-OEt-Ph]; [519, Et, 2-Cl-3-OEt-Ph]; [520, Et, 2-Cl-4-OEt-Ph]; [521, Et, 2-Cl-5-OEt-Ph]; [522, Et, 2-Cl-6-OEt-Ph]; [523, Et, 3-Cl-2-OEt-Ph]; [524, Et, 3-Cl-4-OEt-Ph]; [525, Et, 3-Cl-5-OEt-Ph]; [526, Et, 4-Cl-2-OEt-Ph]; [527, Et, 4-Cl-3-OEt-Ph]; [528, Et, 5-Cl-2-OEt-Ph]; [529, Et, 2-Et-3-OMe-Ph]; [530, Et, 2-Et-4-OMe-Ph]; [531, Et, 2-Et-5-OMe-Ph]; [532, Et, 2-Et-6-OMe-Ph]; [533, Et, 3-Et-2-OMe-Ph]; [534, Et, 3-Et-4-OMe-Ph]; [535, Et, 3-Et-5-OMe-Ph]; [536, Et, 4-Et-2-OMe-Ph]; [537, Et, 4-Et-3-OMe-Ph]; [538, Et, 5-Et-2-OMe-Ph]; [539, Et, 2-OMe-3-Me-Ph]; [540, Et, 2-OMe-4-Me-Ph]; [541, Et, 2-OMe-5-Me-Ph]; [542, Et, 2-OMe-6-Me-Ph]; [543, Et, 3-OMe-2-Me-Ph]; [544, Et, 3-OMe-4-Me-Ph]; [545, Et, 3-OMe-5-Me-Ph]; [546, Et, 4-OMe-2-Me-Ph]; [547, Et, 4-OMe-3-Me-Ph]; [548, Et, 5-OMe-2-Me-Ph]; [549, Et, 2-CF$_3$-Ph]; [550, Et, 3-CF$_3$-Ph]; [551, Et, 4-CF$_3$-Ph]; [552, Et, 2,3-(CF$_3$)$_2$-Ph]; [553, Et, 2,4-(CF$_3$)$_2$-Ph]; [554, Et, 2,5-(CF$_3$)$_2$-Ph]; [555, Et, 2,6-(CF$_3$)$_2$-Ph]; [556, Et, 3,5-(CF$_3$)$_2$-Ph]; [557, Et, 2-CH$_2$CF$_3$-Ph]; [558, Et, 3-CH$_2$CF$_3$-Ph]; [559, Et, 4-CH$_2$CF$_3$-Ph]; [560, Et, 2-CF$_2$CF$_3$-Ph]; [561, Et, 3-CF$_2$CF$_3$-Ph]; [562, Et, 4-CF$_2$CF$_3$-Ph]; [563, Et, 2-CF$_2$CF$_2$CF$_3$-Ph]; [564, Et, 3-CF$_2$CF$_2$CF$_3$-Ph]; [565, Et, 4-CF$_2$CF$_3$CF$_3$-Ph]; [566, Et, 2-OCF$_3$-Ph]; [567, Et, 3-OCF$_3$-Ph]; [568, Et, 4-OCF$_3$-Ph]; [569, Et, 2-OCH$_2$CF$_3$-Ph]; [570, Et, 3-OCH$_2$CF$_3$-Ph]; [571, Et, 4-OCH$_2$CF$_3$-Ph]; [572, Et, 2-SMe-Ph]; [573, Et, 3-SMe-Ph]; [574, Et, 4-SMe-Ph]; [575, Et, 2-SCF$_3$-Ph]; [576, Et, 3-SCF$_3$-Ph]; [577, Et, 4-SCF$_3$-Ph]; [578, Et, 2-CH$_2$=CH-Ph]; [579, Et, 3-CH$_2$=CH-Ph]; [580, Et, 4-CH$_2$=CH-Ph]; [581, Et, 2-ehtynyl-Ph]; [582, Et, 4-CH$_2$=CHCH$_2$-Ph]; [583, Et, 2-CH$_2$=CHCH$_2$O-Ph]; [584, Et, 2-propynyloxy-Ph]; [585, Et, 2-OH-Ph]; [586, Et, 3-OH-Ph]; [587, Et, 4-OH-Ph]; [588, Et, 2-CN-Ph]; [589, Et, 3-CN-Ph]; [590, Et, 4-CN-Ph]; [591, Et, 2-NO$_2$-Ph]; [592, Et, 3-NO$_2$-Ph]; [593, Et, 4-NO$_2$-Ph]; [594, Et, 2-Ph-Ph]; [595, Et, 3-Ph-Ph]; [596, Et, 4-Ph-Ph]; [597, Et, 2-(2-Cl-Ph)-Ph]; [598, Et, 3-(4-Cl-Ph)-Ph]; [599, Et, 4-(3-Cl-Ph)-Ph]; [600, Et, 2-OPh-Ph]; [601, Et, 3-OPh-Ph]; [602, Et, 4-OPh-Ph]; [603, Et, 2-CN-6-Me-Ph]; [604, Et, 3-CN-2-Me-Ph]; [605, Et, 4-CN-2-Me-Ph]; [606, Et, 2-NMe$_2$-Ph]; [607, Et, 3-NMe$_2$-Ph]; [608, Et, 4-NMe$_2$-Ph]; [609, Et, 2-Ac-Ph]; [610, Et, 3-Ac-Ph]; [611, Et, 4-Ac-Ph]; [612, Et, 2-CO$_2$Me-Ph]; [613, Et, 3-CO$_2$Et-Ph]; [614, Et, 4-CO$_2$t-Bu-Ph]; [615, Et, 2-MeOCH$_2$-Ph]; [616, Et, 3-MeOCH$_2$-Ph]; [617, Et, 4-MeOCH$_2$-Ph]; [618, Et, 2-Me-5-CF$_3$-Ph]; [619, Et, 2-Me-5-NO$_2$-Ph]; [620, Et, 5-CN-2-Me-Ph]; [621, Et, 1-Nap]; [622, Et, 2-Nap]; [623, Et, 1-Me-2-Nap]; [624, Et, 2-Me-1-Nap]; [625, Et, 1-OMe-2-Nap]; [626, Et, 2-OMe-1-Nap]; [627, Et, 2-Thie]; [628, Et, 3-Thie]; [629, Et, 3-Me-2-Thie]; [630, Et, 4-Me-2-Thie]; [631, Et, 5-Me-2-Thie]; [632, Et, 3-OMe-2-Thie]; [633, Et, 4-OMe-2-Thie]; [634, Et, 5-OMe-2-Thie]; [635, Et, 2-Me-3-Thie]; [636, Et, 4-Me-3-Thie]; [637, Et, 5-Me-3-Thie]; [638, Et, 2-OMe-3-Thie]; [639, Et, 4-OMe-3-Thie]; [640, Et, 5-OMe-3-Thie]; [641, Et, 2-Fur]; [642, Et, 3-Fur]; [643, Et, 3-Me-2-Fur]; [644, Et, 4-Me-2-Fur]; [645, Et, 5-Me-2-Fur]; [646, Et, 2-Me-3-Fur]; [647, Et, 4-Me-3-Fur]; [648, Et, 5-Me-3-Fur]; [649, Et, 2-Pyrr]; [650, Et, 3-Pyrr]; [651, Et, 1-Me-2-Pyrr]; [652, Et, 1-Me-3-Pyrr]; [653, Et, 3-Me-2-Pyrr]; [654, Et, 4-Me-2-Pyrr]; [655, Et, 5-Me-2-Pyrr]; [656, Et, 2-Me-3-Pyrr]; [657, Et, 4-Me-3-Pyrr]; [658, Et, 5-Me-3-Pyrr]; [659, Et, 1,3-Me$_2$-2-Pyrr]; [660, Et, 1,4-Me$_2$-2-Pyrr]; [661, Et, 1,5-Me$_2$-2-Pyrr]; [662, Et, 1,2-Me$_2$-3-Pyrr]; [663, Et, 1,4-Me$_2$-3-Pyrr]; [664, Et, 1,5-Me$_2$-3-Pyrr]; [665, Et, 2-Py]; [666, Et, 3-Py]; [667, Et, 4-Py]; [668, Et, 3-Me-2-Py]; [669, Et, 4-Me-2-Py]; [670, Et, 5-Me-2-Py]; [671, Et, 6-Me-2-Py]; [672, Et, 2-Me-3-Py]; [673, Et, 4-Me-3-Py]; [674, Et, 5-Me-3-Py]; [675, Et, 6-Me-3-Py]; [676, Et, 2-Me-4-Py]; [677, Et, 3-Me-4-Py]; [678, Et, 3,5-Me$_2$-2-Py]; [679, Et, 3-OMe-2-Py]; [680, Et, 4-OMe-2-Py]; [681, Et, 5-OMe-2-Py]; [682, Et, 6-OMe-2-Py]; [683, Et, 2-OMe-3-Py]; [684, Et, 4-OMe-3-Py]; [685, Et, 5-OMe-3-Py]; [686, Et, 6-OMe-3-Py]; [687, Et, 2-OMe-4-Py]; [688, Et, 3-OMe-4-Py]; [689, Et, 5-Cl-2-Py]; [690, Et, 6-Cl-3-Py]; [691, Et, 5-CF$_3$-2-Py]; [692, Et, 6-CF$_3$-3-Py]; [693, Et, 1,3-Me$_2$-5-pyrazolyl]; [694, Et, 1-Me-2-imidazolyl]; [695, Et, 2-Thia]; [696, Et, 4-Thia]; [697, Et, 5-Me-4-Thia]; [698, Et, 5-Thia]; [699, Et, 4-Me-5-Thia]; [700, Et, 2,5-Me$_2$-4-Thia]; [701, Et, 2-Cl-5-Thia]; [702, Et, 2-CF$_3$-5-Thia]; [703, Pr, Ph]; [704, Pr, 2-F-Ph]; [705, Pr, 3-F-Ph]; [706, Pr, 4-F-Ph]; [707, Pr, 2-Cl-Ph]; [708, Pr, 3-Cl-Ph]; [709, Pr, 4-Cl-Ph]; [710, Pr, 2-Me-Ph]; [711, Pr, 3-Me-Ph]; [712, Pr, 4-Me-Ph]; [713, Pr, 2-Et-Ph]; [714, Pr, 3-Et-Ph]; [715, Pr, 4-Et-Ph]; [716, Pr, 2-OMe-Ph]; [717, Pr, 3-OMe-Ph]; [718, Pr, 4-OMe-Ph]; [719, Pr, 2-OEt-Ph]; [720, Pr, 3-OEt-Ph]; [721, Pr, 4-OEt-Ph]; [722, Pr, 2-CF$_3$-Ph]; [723, Pr, 3-CF$_3$-Ph]; [724, Pr, 4-CF$_3$-Ph]; [725, Pr, 2-SMe-Ph]; [726, Pr, 3-SMe-Ph]; [727, Pr, 4-SMe-Ph]; [728, Pr, 2-SCF$_3$-Ph]; [729, Pr, 3-SCF$_3$-Ph]; [730, Pr, 4-SCF$_3$-Ph]; [731, Pr, 2-Thie]; [732, Pr, 3-Thie]; [733, Pr, 3-Me-2-Thie]; [734, Pr, 4-Me-2-Thie]; [735, Pr, 5-Me-2-Thie]; [736, Pr, 3-OMe-2-Thie]; [737, Pr, 4-OMe-2-Thie]; [738, Pr, 5-OMe-2-Thie]; [739, Pr, 2-Me-3-Thie]; [740, Pr, 4-Me-3-Thie]; [741, Pr, 5-Me-3-Thie]; [742, Pr, 2-OMe-3-Thie]; [743, Pr, 4-OMe-3-Thie]; [744, Pr, 5-OMe-3-Thie]; [745, Pr, 2-Py]; [746, Pr, 3-Py]; [747, Pr, 4-Py]; [748, Pr, 3-Me-2-Py]; [749, Pr, 4-Me-2-Py]; [750, Pr, 5-Me-2-Py]; [751, Pr, 6-Me-2-Py]; [752, Pr, 2-Me-3-Py]; [753, Pr, 4-Me-3-Py]; [754, Pr, 5-Me-3-Py]; [755, Pr, 6-Me-3-Py]; [756, Pr, 2-Me-4-Py]; [757, Pr, 3-Me-4-Py]; [758, Pr, 3,5-Me$_2$-2-Py]; [759, i-Pr, 2-F-Ph]; [760, i-Pr, 3-Me-Ph]; [761, i-Pr, 4-OMe-Ph]; [762, Bu, 5-Me-3-Py]; [763, t-Bu, 4-OMe-2-Thie]; [764, CF$_3$CH$_2$, 2-Me-Ph]; [765, Me, 5-Cl-3-F-2-Me-Ph]; [766, Me, 3-F-5-OMe-2-Me-Ph]; [767, Me, 2-pyrimidinyl]; [768, Me, 4-pyrimidinyl]; [769, Me, 5-pyrimidinyl]; [770, Me, 2-I-Ph]; [771, Me, 3-I-Ph]; [772, Me, 4-I-Ph]; [773, Me, 3-Cl-2-Py]; [774, Me, 4-Cl-3-Py]; [775, Me, 5-Cl-3-Py]; [776, Me, 3,5-Cl$_2$-4-Py]; [777, Et, 5-Cl-3-F-2-Me-Ph]; [778, Et, 3-F-5-OMe-2-Me-Ph]; [779, Et, 2-pyrimidinyl]; [780, Et, 4-pyrimidinyl]; [781, Et, 5-pyrimidinyl]; [782, Et, 2-I-Ph]; [783, Et, 3-I-Ph]; [784, Et, 4-I-Ph]; [785, Et, 3-Cl-2-Py]; [786, Et, 4-Cl-3-Py]; [787, Et, 5-Cl-3-Py]; [788, Et, 3,5-Cl$_2$-4-Py].

Hereinafter, formulation examples are shown. Part(s) represents part(s) by weight.

Formulation Example 1

9 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention is dissolved in a mixture of 37.5 parts of xylene and 37.5 parts of dimethylformamide, 10 parts of polyoxyethylene styryl phenyl ether and 6 parts of calcium dodecylbenzene sulfonate are added thereto, and the mixture is thoroughly mixed by stirring to obtain each emulsion.

Formulation Example 2

5 parts of SORPOL 5060 (registered trade name of TOHO CHEMICAL INDUSTRY CO., LTD.) is added to 40 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention, the mixture is thoroughly mixed, 32 parts of CARPLEX #80 (registered trade name of Shionogi & Co., Ltd., synthetic hydrated silicon oxide fine powder) and 23 parts of 300-mesh diatomaceous earth are added thereto, and the mixture is mixed using a juice mixer to obtain each a water-dispersible agent.

Formulation Example 3

5 parts of synthetic hydrated silicon oxide fine powder, 5 parts of sodium dodecylbenzenesulfonate, 30 parts of bentonite, and 57 parts of clay are added to 3 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention, and the mixture is thoroughly mixed by stirring. Then, a suitable amount of water is added to the mixture, and the resulting product is further stirred, granulated using a granulator, and air dried to obtain each granule.

Formulation Example 4

After 4.5 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention, 1 part of synthetic hydrated silicon oxide fine powder, 1 part of Doriresu B (manufactured by Sankyosha Co., Ltd.) as a coagulant, and 7 parts of clay are thoroughly mixed using a mortar, the mixture is mixed by stirring using a juice mixer. 86.5 parts of cut clay is added to the obtained mixture, and the resulting product is sufficiently mixed by stirring to obtain each powder.

Formulation Example 5

10 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention, 35 parts of a mixture (weight ratio of 1:1) of polyoxyethylene alkyl ether sulfate ammonium salt and white carbon, and 55 parts of water are mixed and pulverized by a wet pulverization method to obtain each formulation.

Formulation Example 6

0.5 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention is dissolved in 10 parts of dichloromethane, and this is mixed with 89.5 parts of Isopar M (isoparaffin: registered trade name of Exxon Mobil Corporation) to obtain each oil solution.

Formulation Example 7

0.1 parts of any one of the compounds (1a-1) to (1a-61), (1a-63) to (1a-91), (1a-201) to (1a-61), (1a-63) to (1a-204), (1b-1), (1c-1), (1b-2), (1c-2), (1b-12), and (1c-12) of the present invention and 49.9 parts of Neo-chioZol (Chuo Kasei Co., Ltd.) are put into an aerosol can which is then installed with an aerosol valve. Thereafter, the aerosol can is filled with 25 parts of dimethyl ether and 25 parts of LPG, vibration is applied to the aerosol can, and an actuator is installed to obtain an oil-based aerosol.

Formulation Example 8

An aerosol container is filled with a mixture in which 0.6 parts of any one of the compounds (1a-1) to (1a-61), (1a-63) to (1a-91), (1a-201) to (1a-204), (1b-1), (1c-1), (1b-2), (1c-2), (1b-12), and (1c-12) of the present invention, 0.01 parts of BHT, 5 parts of xylene, 3.39 parts of deodorized kerosine, and 1 part of emulsifier {ATMOS 300 (registered trade name of ATMOS Chemical Ltd.)} are mixed together and dissolved and 50 parts of distilled water, and is provided with a valve portion. Then, the container is filled with 40 parts of propellant (LPG) under pressure through the valve to obtain an aqueous aerosol of each compound described above.

Next, it will be shown that the compounds of the present invention are effective as active ingredients of a pest control agent, with reference to test examples. The compounds of the present invention are represented by the compound numbers described above.

Test Example 1

Test solutions were prepared by diluting a formulation of the compound (1a-9) of the present invention, which was obtained from Formulation Example 5, with water so that the concentration of the active ingredients becomes 500 ppm.

20 ml of the above-described test solution was scattered on cabbages (*Brassicae oleracea*) in a third- or fourth-leaf stage. After air-drying the test solution, the overground portion was cut, collected, and accommodated in a polyethylene cup (capacity of 100 ml) together with 5 second-instar larvae of diamondback moths (*Plutella xylostella*), followed by storing at 25° C. The number of dead insects was checked after 5 days and the mortality was obtained using the following equation.

Mortality (%)=(the number of dead insects/the number of insects provided for a test)×100

As a result, in the treatment of the compound (1a-9) of the present invention, the mortality was equal to or greater than 80%.

Test Example 2

Test solutions were prepared by diluting each formulation of the compounds (1a-2), (1a-23), (1a-26), (1a-29), (1a-30), (1a-31), (1a-33), (1a-35), (1a-36), and (1a-38) of the present invention, which were obtained from Formulation Example 5, with water so that the concentration of the active ingredients becomes 500 ppm.

A filter paper having a diameter of 5.5 cm was spread on the bottom of a polyethylene cup having the same size as that of the filter paper, artificial feed Silk Mate 2S (Nosan Corporation) sliced in a thickness of 2 mm were placed thereon, and 1 ml of any one (500 ppm) of the above-described test solutions was irrigated thereto.

After air-drying the test solution, a filter paper having a diameter of 5.5 cm was placed on the artificial feed, 30 first-instar larvae of summer fruit *tortrix* moths (*Adoxophyes orana*) were released thereon, which was then covered with a lid. The number of dead insects was checked after 7 days and the mortality was obtained using the following equation.

Mortality (%)=(the number of dead insects/the number of insects provided for a test)×100

As a result, in the treatment of the compounds (1a-2), (1a-23), (1a-26), (1a-29), (1a-30), (1a-31), (1a-33), (1a-35), (1a-36), and (1a-38) of the present invention, the mortality was equal to or greater than 90%.

Test Example 3

Test solutions were prepared by diluting each formulation of the compounds (1a-1), (1a-2), (1a-3), (1a-5), (1a-6), (1a-7), (1a-8), (1a-14), (1a-15), (1a-16), (1a-18), (1a-19), (1a-20), (1a-21), (1a-22), (1a-23), (1a-28), (1a-31), (1a-32), (1a-33), (1a-35), (1a-37), (1a-38), (1a-39), (1a-42), (1a-50), (1a-77), (1a-78), (1a-81), (1a-86), (1a-87), (1a-201), (1a-202), (1a-203), and (1b-2) of the present invention, which were obtained from Formulation Example 5, with water so that the concentration of the active ingredients becomes 500 ppm.

10 ml of any one of the above-described test solutions was scattered on rice seedlings in a second-leaf development stage which were planted in polyethylene cups. After air-drying the test solution, 20 third- or fourth-instar larvae of brown planthoppers (*Nilaparvata lugens*) were released and stored at a room temperature of 25° C. The number of surviving parasitic brown planthoppers on the rice was checked after 6 days and the controlling value was obtained using the following equation.

Controlling value (%)={1−(Cb×Tai)/(Cai×Tb)}×100

The characters in the formula represent the following meanings.

Cb: the number of insects in a non-treatment section before treatment

Cai: the number of insects in a non-treatment section at observation

Tb: the number of insects in a treatment section before treatment

Tai: the number of insects in a treatment section at observation

As a result, each treatment section of the test solution of the compounds (1a-1), (1a-2), (1a-3), (1a-5), (1a-6), (1a-7), (1a-8), (1a-14), (1a-15), (1a-16), (1a-18), (1a-19), (1a-20), (1a-21), (1a-22), (1a-23), (1a-28), (1a-31), (1a-32), (1a-33), (1a-35), (1a-37), (1a-38), (1a-39), (1a-42), (1a-50), (1a-77), (1a-78), (1a-81), (1a-86), (1a-87), (1a-201), (1a-202), (1a-203), and (1b-2) of the present invention showed a controlling value equal to or greater than 90%.

Test Example 4

Test solutions were prepared by diluting each formulation of the compounds (1a-2), (1a-5), (1a-9), (1a-14), (1a-20), (1a-23), (1a-30), (1a-37), (1a-38), (1a-48), (1a-51), (1a-52), (1a-54), (1a-57), (1a-72), (1a-75), and (1b-2) of the present invention, which were obtained from Formulation Example 5, with water so that the concentration of the active ingredients becomes 500 ppm.

On the other hand, cucumber seedlings (first-leaf development stage) planted in plastic cups were inoculated with about 30 cotton aphids (*Aphis gossypii*) and were allowed to stand for 1 day. 20 ml of any one of the above-described test solutions was respectively scattered on the seedlings.

6 days after the scattering, the number of surviving parasitic cotton aphids on the leaves of the cucumber was checked and the controlling value was obtained using the following equation.

Controlling value (%)={1−(Cb×Tai)/(Cai×Tb)}×100

The characters in the formula represent the following meanings.

Cb: the number of insects in a non-treatment section before treatment

Cai: the number of insects in a non-treatment section at observation

Tb: the number of insects in a treatment section before treatment

Tai: the number of insects in a treatment section at observation

As a result, each treatment section of the test solution of the compounds (1a-2), (1a-5), (1a-9), (1a-14), (1a-20), (1a-23), (1a-30), (1a-37), (1a-38), (1a-48), (1a-51), (1a-52), (1a-54), (1a-57), (1a-72), (1a-75), and (1b-2) of the present invention showed a controlling value equal to or greater than 90%.

Test Example 5

Test solutions were prepared by diluting each formulation of the compounds (1a-2), (1a-4), (1a-9), and (1a-30) which were obtained from Formulation Example 5, with water so that the concentration of the active ingredients becomes 500 ppm.

The roots of cucumber seedlings (first-leaf development stage) from which the soil was washed off were immersed to 5 ml of any one of the above-described test solutions, and 1 day after the treatment, cucumber leaf surfaces were inoculated with about 30 cotton aphids (all stages). After 7 days, the number of surviving parasitic cotton aphids on the leaves of the cucumber was checked and the controlling value was obtained using the following equation.

Controlling value (%)={1−(Cb×Tai)/(Cai×Tb)}×100

The characters in the formula represent the following meanings.

Cb: the number of insects in a non-treatment section before treatment

Cai: the number of insects in a non-treatment section at observation

Tb: the number of insects in a treatment section before treatment

Tai: the number of insects in a treatment section at observation

As a result, each treatment section of the test solution of the compounds (1a-2), (1a-4), (1a-9), and (1a-30) of the present invention showed a controlling value equal to or greater than 90%.

Test Example 6

Test solutions were prepared by diluting a formulation of the compound (1a-6) of the present invention, which was obtained from Formulation Example 5, with water so that the concentration of the active ingredients becomes 500 ppm.

10 female imagoes of two-spotted spider mite (*Tetranychus urticae*) were released on kidney beans immediately after the primary leaf development. The next day, the test solution was sprayed at an amount in which the test solution dripped, using a spray gun. The treated kidney beans were placed in a constant temperature breeding room (25° C.), the number of surviving larvae was checked 7 days after the treatment, and the mortality was obtained using the following equation.

Controlling value (%)=(1−the number of surviving female imagoes in a treatment section/the number of surviving female imagoes in a non-treatment section)×100

As a result, in the treatment of the compound (1a-6) of the present invention, the controlling value was equal to or greater than 90%.

Test Example 7

Test solutions were prepared by diluting each formulation of the compounds (1a-23), (1a-24), and (1a-75) of the present invention, which were obtained from Formulation Example 5, with water so that the concentration of the active ingredients becomes 500 ppm.

A filter paper having a diameter of 5.5 cm was spread on the bottom of a polyethylene cup having the same size as that of the filter paper, 0.7 ml of any one of the above-described test solutions was added dropwise onto the filter paper, and 30 mg of sucrose was uniformly put therein as bait. 10 female imagoes of common houseflies (*Musca domestica*) were released in the polyethylene cup, which was then covered with a lid. The number of live and dead common houseflies was checked after 24 hours and the mortality was obtained using the following equation.

Mortality (%)=(the number of dead insects/the number of insects provided for a test)×100

As a result, in the treatment of the compounds (1a-23), (1a-24), and (1a-75) of the present invention, the mortality was 100%.

Test Example 8

Test solutions were prepared by diluting each formulation of the compounds (1a-2), (1a-16), and (1a-20) of the present invention, which were obtained from Formulation Example 5, with water so that the concentration of the active ingredients becomes 500 ppm.

A filter paper having a diameter of 5.5 cm was spread on the bottom of a polyethylene cup having the same size as that of the filter paper, 0.7 ml of any one of the above-described test solutions was added dropwise onto the filter paper, and 30 mg of sucrose was uniformly put therein as bait. 2 male imagoes of German cockroaches (*Blattella germanica*) were released in the polyethylene cup, which was then covered with a lid. The number of dead insects was counted after 24 hours and the mortality was obtained using the following equation.

Mortality (%)=(the number of dead insects/the number of insects provided for a test)×100

As a result, in the treatment of the compounds (1a-2), (1a-16), and (1a-20) of the present invention, the mortality was 100%.

Test Example 9

Test solutions were prepared by diluting each formulation of the compounds (1a-1) and (1a-19) of the present invention, which were obtained from Formulation Example 5, with water so that the concentration of the active ingredients becomes 500 ppm.

A filter paper having a diameter of 5.5 cm was spread on the bottom of a polyethylene cup having the same size as that of the filter paper, 0.7 ml of any one of the above-described test solutions was added dropwise onto the filter paper, and 30 mg of sucrose was uniformly put therein as bait. 2 male imagoes of German cockroaches (*Blattella germanica*) were released in the polyethylene cup, which was then covered with a lid. The number of dead insects was counted after 6 days and the mortality was obtained using the following equation.

Mortality (%)=(the number of dead insects/the number of insects provided for a test)×100

As a result, in the treatment of the compounds (1a-1) and (1a-19) of the present invention, the mortality was 100%.

Test Example 10

Test solutions were prepared by diluting each formulation of the compounds (1a-1), (1a-2), (1a-5), (1a-6), (1a-8), (1a-14), (1a-15), (1a-19), (1a-20), (1a-22), (1a-23), (1a-38), (1a-39), (1a-42), (1a-77), (1a-87), (1a-201), (1a-203), and (1b-2) of the present invention, which were obtained from Formulation Example 5, with water so that the concentration of the active ingredients becomes 500 ppm.

0.7 ml of any one of the above-described test solutions was added to 100 ml of ion exchange water (concentration of active ingredients of 3.5 ppm). 20 final-instar larvae of common house mosquito (*Culex pipiens pallens*) were released in the solution, the number of live and dead common house mosquitoes was checked after 24 hours, and the mortality was obtained using the following equation.

Mortality (%)=(the number of dead insects/the number of insects provided for a test)×100

As a result, in the treatment of the compounds (1a-1), (1a-2), (1a-5), (1a-6), (1a-8), (1a-14), (1a-15), (1a-19), (1a-20), (1a-22), (1a-23), (1a-38), (1a-39), (1a-42), (1a-77), (1a-87), (1a-201), (1a-203), and (1b-2) of the present invention, the mortality was equal to or greater than 90%.

Test Example 11

Test solutions were prepared by diluting each formulation of the compounds (1a-3), (1a-7), (1a-13), (1a-21), (1a-64), (1a-74), (1a-75), and (1a-78) of the present invention, which were obtained from Formulation Example 5, with water so that the concentration of the active ingredients becomes 500 ppm.

0.7 ml of any one of the above-described test solutions was added to 100 ml of ion exchange water (concentration of active ingredients of 3.5 ppm). 20 final-instar larvae of common house mosquitoes (*Culex pipiens pallens*) were released in the solution, the number of live and dead common house mosquitoes was checked after 6 days, and the mortality was obtained using the following equation.

Mortality (%)=(the number of dead insects/the number of insects provided for a test)×100

As a result, in the treatment of the compounds (1a-3), (1a-7), (1a-13), (1a-21), (1a-64), (1a-74), (1a-75), and (1a-78) of the present invention, the mortality was equal to or greater than 90%.

Test Example 12

10 mg of each of the compounds (1a-1), (1a-2), (1a-4), (1a-5), (1a-6), (1a-7), (1a-19), (1a-20), (1a-22), (1a-23), (1a-32), (1a-38), (1a-39), (1a-77), (1b-1), and (1b-2) of the present invention was dissolved in 3 ml of acetone. Test solutions were prepared by diluting each of the above solutions 20-fold with acetone (concentration of active ingredients of 167 ppm). Imagos of *gambiae* sensu stricto (*Anopheles gambiae*) were anesthetized with carbon dioxide gas, and any one of the above-described test solutions was topically applied to the chest back plate of the females by 0.3 µl thereof. The test was performed on 10 imagos per group, after the topical application, the imagos were transferred to a cup, and 5 percent sugar water was given. The number of live and dead imagos were checked 2 days after the topical application, and the mortality was obtained using the following equation.

Mortality (%)=(the number of dead insects/the number of insects provided for a test)×100

As a result, in the treatment of the compounds (1a-1), (1a-2), (1a-4), (1a-5), (1a-6), (1a-7), (1a-19), (1a-20), (1a-22), (1a-23), (1a-32), (1a-38), (1a-39), (1a-77), (1b-1), and (1b-2) of the present invention, the mortality was equal to or greater than 90%.

INDUSTRIAL APPLICABILITY

The compound of the present invention has a control activity against pests and is effective as active ingredients of a pest control agent.

The invention claimed is:

1. A thiazole compound represented by Formula (1):

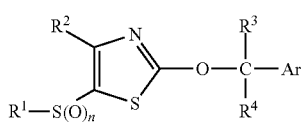

wherein $R^1$ represents a C1-C4 alkyl group optionally having one or more fluorine atoms, $R^2$ represents a C1-C4 alkyl group optionally having one or more fluorine atoms or a hydrogen atom, $R^3$ and $R^4$ are the same or different and each represents a C1-C4 alkyl group optionally having one or more fluorine atoms, a C3-C6 cycloalkyl group, or a hydrogen atom, Ar represents a phenyl group optionally having one or more atoms or groups selected from the group A, a naphthyl group optionally having one or more atoms or groups selected from the group A, or a 5- or 6-membered heteroaryl group optionally having one or more atoms or groups selected from the group A, and n represents 0, 1, or 2, Group A is a group consisting of a C1-C4 alkyl group optionally having one or more fluorine atoms, a C2-C4 alkenyl group, a C2-C4 alkynyl group, a C1-C4 alkoxy group optionally having one or more fluorine atoms, a C2-C4 alkenyloxy group, a C2-C4 alkynyloxy group, a C1-C4 alkylthio group optionally having one or more fluorine atoms, a C1-C4 alkylsulfinyl group optionally having one or more fluorine atoms, a C1-C4 alkylsulfonyl group optionally having one or more fluorine atoms, a phenyl group optionally having one or more atoms or groups selected from the group B, a phenoxy group optionally having one or more atoms or groups selected from the group B, a formyl group, a (C1-C3 alkyl) carbonyl group, a benzoyl group, a (C1-C3 alkoxy) C1-C3 alkyl group, a (C1-C3 alkoxy) carbonyl group, a hydroxy group, a cyano group, a nitro group, a di(C1-C3 alkyl) amino group, and a halogen atom, Group B is a group consisting of a halogen atom, a methyl group, a trifluoromethyl group, a methoxy group, and a trifluoromethoxy group.

2. The thiazole compound according to claim 1, wherein, in Formula (1), $R^1$ is a C1-C3 alkyl group, $R^2$ is a hydrogen atom or a C1-C3 alkyl group, $R^3$ and $R^4$ are the same or different and each represents a hydrogen atom or a C1-C3 alkyl group, and Ar is a phenyl group optionally having one or more atoms or groups selected from the group A, a naphthyl group optionally having one or more atoms or groups selected from the group A, a pyridyl group optionally having one or more atoms or groups selected from the group A, a thienyl group optionally having one or more atoms or groups selected from the group A, a furyl group optionally having one or more atoms or groups selected from the group A, or a pyrrolyl group optionally having one or more atoms or groups selected from the group A.

3. The thiazole compound according to claim 1, wherein, in Formula (1), $R^1$ represents a methyl group or an ethyl group, $R^2$ represents a hydrogen atom, $R^3$ represents a hydrogen atom, $R^4$ represents a hydrogen atom or a methyl group, Ar is a phenyl group optionally having one or more atoms or groups selected from the group C, a naphthyl group optionally having one or more atoms or groups selected from the group C, a pyridyl group optionally having one or more atoms or groups selected from the group C, a thienyl group optionally having one or more atoms or groups selected from the group C, or a furyl group optionally having one or more atoms or groups selected from the group C, n is 0 or 1, and the group C is the group consisting of a halogen atom, a methyl group, an ethyl group, a methoxy group, and an ethoxy group.

4. A pest control agent comprising the thiazole compound according to claim 1 and an inert carrier.

5. A method for controlling pests comprising applying an effective amount of the thiazole compound according to claim 1 to pests or a habitat of the pests.

6. A pest control agent comprising the thiazole compound according to claim 2 and an inert carrier.

7. A method for controlling pests comprising applying an effective amount of the thiazole compound according to claim 2 to pests or a habitat of the pests.

8. A pest control agent comprising the thiazole compound according to claim 3 and an inert carrier.

9. A method for controlling pests comprising applying an effective amount of the thiazole compound according to claim 3 to pests or a habitat of the pests.

* * * * *